(12) United States Patent
Freeman et al.

(10) Patent No.: US 10,729,913 B2
(45) Date of Patent: Aug. 4, 2020

(54) PATIENT-WORN ENERGY DELIVERY APPARATUS

(71) Applicant: ZOLL Medical Corporation, Chelmsford, MA (US)

(72) Inventors: Gary A Freeman, Waltham, MA (US); James G Radzelovage, Londonderry, NH (US)

(73) Assignee: Zoll Medical Corporation, Chelmsford, MA (US)

( * ) Notice: Subject to any disclaimer, the term of this patent is extended or adjusted under 35 U.S.C. 154(b) by 156 days.

(21) Appl. No.: 15/924,626

(22) Filed: Mar. 19, 2018

(65) Prior Publication Data

US 2019/0282822 A1    Sep. 19, 2019

(51) Int. Cl.
*A61B 5/0408*    (2006.01)
*A61N 1/39*    (2006.01)
*A61N 1/04*    (2006.01)
*A61N 1/365*    (2006.01)

(52) U.S. Cl.
CPC ......... *A61N 1/3987* (2013.01); *A61N 1/0484* (2013.01); *A61N 1/3904* (2017.08); *A61B 5/04087* (2013.01); *A61N 1/36507* (2013.01); *A61N 1/3975* (2013.01)

(58) Field of Classification Search
CPC .. A61B 5/04087; A61N 1/046; A61N 1/0476; A61N 1/0484; A61N 1/0496; A61N 1/05; A61N 1/3625; A61N 1/36507; A61N 1/36521; A61N 1/3904; A61N 1/3937; A61N 1/3956; A61N 1/3975; A61N 1/3981; A61N 1/3987; A61N 2001/083
See application file for complete search history.

(56) References Cited

U.S. PATENT DOCUMENTS

| 4,928,690 A | 5/1990 | Heilman et al. |
| 6,301,502 B1 | 10/2001 | Owen et al. |
| 9,289,617 B2 | 3/2016 | Radzelovage |

(Continued)

OTHER PUBLICATIONS

Kroll, Mark W., A Minimal Model of the Single Capacitor Biphasic Defibrillation Waveform, PACE, vol. 17, Nov. 1994, Part I, pp. 1782-1792.

(Continued)

*Primary Examiner* — George Manuel
(74) *Attorney, Agent, or Firm* — Finch & Maloney PLLC

(57) ABSTRACT

A patient-worn arrhythmia monitoring and treatment device includes a pair of therapy electrodes and at least one pair of sensing electrodes disposed proximate to the skin and configured to continually sense at least one ECG signal of the patient over an extended period of time. The device includes a therapy delivery circuit coupled to the pair of therapy electrodes and configured to deliver one or more therapeutic pulses. A controller coupled to therapy delivery circuit is configured to analyze the at least one ECG signal and detect one or more treatable arrhythmias and cause the therapy delivery circuit to deliver the one or more therapeutic pulses to the patient. At least one of the one or more therapeutic pulses is formed as a biphasic waveform delivering within 15 percent of 360 J of energy to a patient body having a transthoracic impedance from about 20 to about 200 ohms.

41 Claims, 25 Drawing Sheets

(56) References Cited

U.S. PATENT DOCUMENTS

| | | | |
|---|---|---|---|
| 2002/0029068 A1* | 3/2002 | Lyster | A61N 1/39 |
| | | | 607/5 |
| 2008/0177341 A1* | 7/2008 | Bowers | A61N 1/3943 |
| | | | 607/5 |
| 2014/0046393 A1 | 2/2014 | Sullivan | |
| 2014/0243918 A1 | 8/2014 | Sullivan et al. | |
| 2017/0225001 A1* | 8/2017 | Zaidi | A61N 1/3987 |
| 2017/0266078 A1 | 9/2017 | Jayne et al. | |

OTHER PUBLICATIONS

Irnich, Werner, From Defibrillation Theory to Clinical Implications, PACE, 2009, pp. 1-12.

Tang, Wanchun et al., The Effects of Biphasic Waveform Design on Post-Resuscitation Myocardial Function, Journal of the American College of Cardiology, vol. 43, No. 7, Apr. 7, 2004, pp. 1228-1235.

Shorofsky, Stephen R. et al., Effect of Second-Phase Duration on the Strength-Duration Relation for Human Transvenous Defibrillation, Circulation, Oct. 31, 2000, pp. 2239-2242.

Understanding Defibrillation Waveforms, http://www/resuscitationcentral.com/defibrillation/defibrillation-waveforms, Oct. 30, 2017, 6 pages.

* cited by examiner

| N Caps | C (uF) | V (volts) | E(s) (J) | R (ohms) | E(d) (J) | T (mS) | I Peak (A) | I Min (A) | I Avg (A) |
|---|---|---|---|---|---|---|---|---|---|
| 1 | 500 | 1800 | 810 | 25 | 400 | 4.3 | 72.0 | 51.2 | 61.6 |
| 1 | 500 | 1800 | 810 | 50 | 360 | 7.3 | 36.0 | 26.8 | 31.4 |
| 1 | 500 | 1800 | 810 | 75 | 360 | 11.0 | 24.0 | 17.9 | 20.9 |
| 1 | 500 | 1800 | 810 | 100 | 360 | 14.7 | 18.0 | 13.4 | 15.7 |
| 1 | 500 | 1800 | 810 | 125 | 360 | 18.4 | 14.4 | 10.7 | 12.6 |
| 1 | 500 | 1900 | 903 | 150 | 360 | 19.1 | 12.7 | 9.8 | 11.2 |
| 1 | 500 | 2000 | 1000 | 175 | 360 | 19.5 | 11.4 | 9.1 | 10.3 |
| 1 | 500 | 2100 | 1103 | 200 | 360 | 19.8 | 10.5 | 8.6 | 9.6 |

FIG. 4A

| N Caps | C (uF) | V (volts) | E(s) (J) | R (ohms) | E(d) (J) | T (mS) | I Peak (A) | I Min (A) | I Avg (A) |
|---|---|---|---|---|---|---|---|---|---|
| 2 | 500 | 1050 | 551 | 25 | 400 | 4.0 | 84.0 | 60.8 | 72.4 |
| 2 | 500 | 1050 | 551 | 50 | 360 | 6.6 | 42.0 | 32.2 | 37.1 |
| 2 | 500 | 1050 | 551 | 75 | 360 | 9.9 | 28.0 | 21.5 | 24.7 |
| 2 | 500 | 1050 | 551 | 100 | 360 | 13.2 | 21.0 | 16.1 | 18.6 |
| 2 | 500 | 1050 | 551 | 125 | 360 | 16.5 | 16.8 | 12.9 | 14.8 |
| 2 | 500 | 1050 | 551 | 150 | 360 | 19.8 | 14.0 | 10.7 | 12.4 |
| 2 | 500 | 1100 | 605 | 175 | 360 | 19.8 | 12.6 | 10.0 | 11.3 |
| 2 | 500 | 1150 | 661 | 200 | 360 | 19.7 | 11.5 | 9.4 | 10.5 |

FIG. 4B

| N Caps | C (uF) | V (volts) | E(s) (J) | R (ohms) | E(d) (J) | T (mS) | I Peak (A) | I Min (A) | I Avg (A) |
|---|---|---|---|---|---|---|---|---|---|
| 3 | 500 | 700 | 368 | 25 | 350 | 6.3 | 84.0 | 50.6 | 67.3 |
| 3 | 500 | 900 | 608 | 50 | 375 | 4.0 | 54.0 | 46.0 | 50.0 |
| 3 | 500 | 900 | 608 | 75 | 375 | 6.0 | 36.0 | 30.7 | 33.3 |
| 3 | 500 | 900 | 608 | 100 | 375 | 8.0 | 27.0 | 23.0 | 25.0 |
| 3 | 500 | 900 | 608 | 125 | 375 | 10.0 | 21.6 | 18.4 | 20.0 |
| 3 | 500 | 900 | 608 | 150 | 375 | 12.0 | 18.0 | 15.3 | 16.7 |
| 3 | 500 | 900 | 608 | 175 | 375 | 14.0 | 15.4 | 13.1 | 14.3 |
| 3 | 500 | 900 | 608 | 200 | 375 | 16.0 | 13.5 | 11.5 | 12.5 |

FIG. 4C

| N Caps | C (uF) | V (volts) | E(s) (J) | R (ohms) | E(d) (J) | T (mS) | I Peak (A) | I Min (A) | I Avg (A) |
|---|---|---|---|---|---|---|---|---|---|
| 4 | 500 | 625 | 391 | 25 | 365 | 4.3 | 100.0 | 71.1 | 85.6 |
| 4 | 500 | 650 | 423 | 50 | 414 | 12.2 | 52.0 | 31.9 | 42.0 |
| 4 | 500 | 650 | 423 | 75 | 414 | 18.3 | 34.7 | 21.3 | 28.0 |
| 4 | 500 | 700 | 490 | 100 | 414 | 11.6 | 28.0 | 22.2 | 25.1 |
| 4 | 500 | 700 | 490 | 125 | 414 | 14.6 | 22.4 | 17.7 | 20.1 |
| 4 | 500 | 700 | 490 | 150 | 414 | 17.5 | 18.7 | 14.8 | 16.7 |
| 4 | 500 | 800 | 640 | 175 | 414 | 11.4 | 18.3 | 16.1 | 17.2 |
| 4 | 500 | 800 | 640 | 200 | 414 | 13.0 | 16.0 | 14.0 | 15.0 |

FIG. 4D

| N Caps | C (uF) | V (volts) | E(s) (J) | R (ohms) | E(d) (J) | T (mS) | I Peak (A) | I Min (A) | I Avg (A) |
|---|---|---|---|---|---|---|---|---|---|
| 3 | 250 | 1100 | 454 | 25 | 450 | 5.0 | 132.0 | 59.4 | 95.7 |
| 3 | 250 | 1150 | 496 | 50 | 450 | 5.0 | 69.0 | 46.4 | 57.7 |
| 3 | 250 | 1150 | 496 | 75 | 450 | 7.4 | 46.0 | 30.9 | 38.5 |
| 3 | 250 | 1150 | 496 | 100 | 450 | 9.9 | 34.5 | 23.2 | 28.9 |
| 3 | 250 | 1150 | 496 | 125 | 450 | 12.4 | 27.6 | 18.6 | 23.1 |
| 3 | 250 | 1150 | 496 | 150 | 450 | 14.9 | 23.0 | 15.5 | 19.2 |
| 3 | 250 | 1150 | 496 | 175 | 450 | 17.3 | 19.7 | 13.3 | 16.5 |
| 3 | 250 | 1150 | 496 | 200 | 450 | 19.8 | 17.3 | 11.6 | 14.4 |

FIG. 11A

| N Caps | C (uF) | V (volts) | E(s) (J) | R (ohms) | E(d) (J) | T (mS) | I Peak (A) | I Min (A) | I Avg (A) |
|---|---|---|---|---|---|---|---|---|---|
| 4 | 250 | 900 | 405 | 25 | 403 | 4.1 | 144.0 | 74.1 | 109.1 |
| 4 | 250 | 1000 | 500 | 50 | 475 | 4.7 | 80.0 | 55.0 | 67.5 |
| 4 | 250 | 1000 | 500 | 75 | 475 | 7.0 | 53.3 | 36.7 | 45.0 |
| 4 | 250 | 1000 | 500 | 100 | 475 | 9.4 | 40.0 | 27.5 | 33.8 |
| 4 | 250 | 1000 | 500 | 125 | 475 | 11.7 | 32.0 | 22.0 | 27.0 |
| 4 | 250 | 1000 | 500 | 150 | 475 | 14.0 | 26.7 | 18.3 | 22.5 |
| 4 | 250 | 1000 | 500 | 175 | 475 | 16.4 | 22.9 | 15.7 | 19.3 |
| 4 | 250 | 1000 | 500 | 200 | 475 | 18.7 | 20.0 | 13.8 | 16.9 |

FIG. 11B

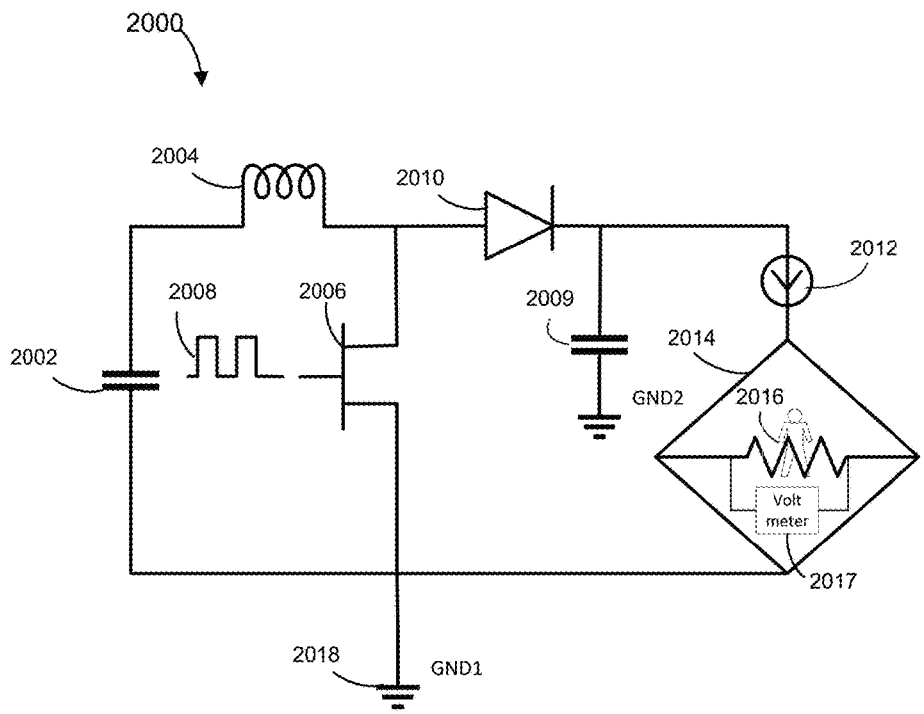
FIG. 20A
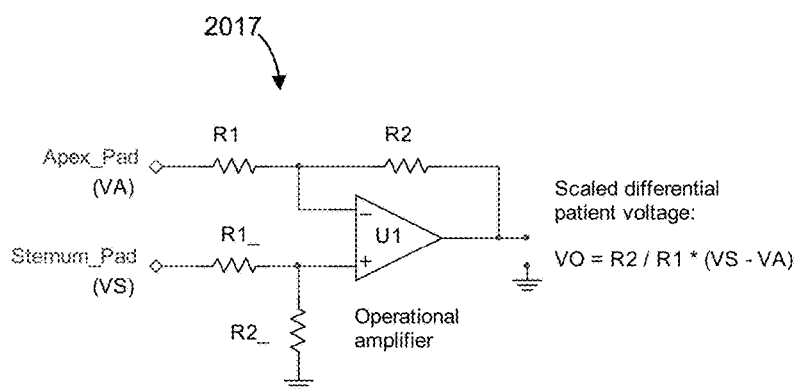
FIG. 20B
| C (uF) | E(s) (J) | V (volts) |
|--------|----------|-----------|
| 150    | 450      | 2449      |
| 400    | 450      | 1500      |
| 450    | 450      | 1414      |
| 500    | 450      | 1342      |
| 550    | 450      | 1279      |
| 600    | 450      | 1225      |
| 650    | 450      | 1177      |
FIG. 20C

| 302g | 305g | 310g | 315g | 320g | 325g | 330g | 333g | 335g | 337g |
|---|---|---|---|---|---|---|---|---|---|
| N Caps | C (uF) | V (volts) | E(s) (J) | R (ohms) | E(d) (J) | T (mS) | I Peak (A) | I Min (A) | I Avg (A) |
| 1 | 200 | 2100 | 441 | 25 | 360 | 4.2 | 84.0 | 36.0 | 60.0 |
| 1 | 200 | 2100 | 441 | 50 | 360 | 8.5 | 42.0 | 18.0 | 30.0 |
| 1 | 200 | 2100 | 441 | 75 | 360 | 12.7 | 28.0 | 12.0 | 20.0 |
| 1 | 200 | 2100 | 441 | 100 | 360 | 16.9 | 21.0 | 9.0 | 15.0 |
| 1 | 200 | 2100 | 441 | 125 | 360 | 21.2 | 16.8 | 7.2 | 12.0 |
| 1 | 200 | 2100 | 441 | 150 | 360 | 25.4 | 14.0 | 6.0 | 10.0 |
| 1 | 200 | 2100 | 441 | 175 | 250 to 360 | 25.0 | 12.0 | 5.1 | 8.6 |
| 1 | 200 | 2100 | 441 | 200 | 175 to 360 | 25.0 | 10.5 | 4.5 | 7.5 |

FIG. 21A

| 302h | 305h | 310h | 315h | 320h | 325h | 330h | 333h | 335h | 337h |
|---|---|---|---|---|---|---|---|---|---|
| N Caps | C (uF) | V (volts) | E(s) (J) | R (ohms) | E(d) (J) | T (mS) | I Peak (A) | I Min (A) | I Avg (A) |
| 2 | 138 | 1620 | 362 | 25 | 360 | 4.4 | 129.6 | 36.0 | 82.8 |
| 2 | 138 | 1620 | 362 | 50 | 360 | 8.8 | 64.8 | 18.0 | 41.4 |
| 2 | 138 | 1620 | 362 | 75 | 360 | 13.2 | 43.2 | 12.0 | 27.6 |
| 2 | 138 | 1620 | 362 | 100 | 360 | 17.7 | 32.4 | 9.0 | 20.7 |
| 2 | 138 | 1620 | 362 | 125 | 360 | 22.1 | 25.9 | 7.2 | 16.6 |
| 2 | 138 | 1620 | 362 | 150 | 250 to 360 | 25.0 | 21.6 | 6.0 | 13.8 |
| 2 | 138 | 1620 | 362 | 175 | 175 to 360 | 25.0 | 18.5 | 5.1 | 11.8 |
| 2 | 138 | 1620 | 362 | 200 | 175 to 360 | 25.0 | 16.2 | 4.5 | 10.4 |

FIG. 21B

PATIENT-WORN ENERGY DELIVERY APPARATUS

BACKGROUND

The present disclosure is directed to monitoring and treating heart arrhythmias with the administration of electrical therapy and to an energy delivery apparatus for imparting the electrical therapy.

A wide variety of electronic and mechanical devices monitor and treat medical conditions. In some examples, depending on the underlying medical condition being monitored or treated, medical devices such as cardiac monitors or defibrillators may be surgically implanted or externally connected to a patient. In some cases, physicians may use medical devices alone or in combination with drug therapies to treat conditions such as cardiac arrhythmias.

One of the most deadly cardiac arrhythmias is ventricular fibrillation, which occurs when normal, regular electrical impulses are replaced by irregular and rapid impulses, causing the heart muscle to stop normal contractions. Normal blood flow ceases, and organ damage or death can result in minutes if normal heart contractions are not restored. Because the victim has no perceptible warning of the impending fibrillation, death often occurs before medical assistance can arrive. Other cardiac arrhythmias can include excessively slow heart rates known as bradycardia or excessively fast heart rates known as tachycardia. Cardiac arrest can occur when the heart experiences various arrhythmias that result in the heart providing insufficient levels of blood flow to the brain and other vital organs for the support of life. Such arrhythmias include, for example, ventricular fibrillation, ventricular tachycardia, pulseless electrical activity (PEA), and asystole (heart stops all electrical activity).

Cardiac arrest and other cardiac health ailments are a major cause of death worldwide. Various resuscitation efforts aim to maintain the body's circulatory and respiratory systems during cardiac arrest in an attempt to save the life of the patient. The sooner these resuscitation efforts begin, the better the patient's chances of survival. Implantable cardioverter/defibrillators (ICDs) or external defibrillators (such as manual defibrillators or automated external defibrillators (AEDs)) have significantly improved the ability to treat these otherwise life-threatening conditions. Such devices operate by applying corrective electrical pulses directly to the patient's heart. Ventricular fibrillation or ventricular tachycardia can be treated by an implanted or external defibrillator, for example, by providing a therapeutic shock to the heart in an attempt to restore normal rhythm. To treat conditions such as bradycardia, an implanted or external pacing device can provide pacing stimuli to the patient's heart until intrinsic cardiac electrical activity returns.

Example external cardiac monitoring and/or treatment devices include cardiac monitors, the ZOLL LifeVest® wearable cardioverter defibrillator available from ZOLL Medical Corporation, and the AED Plus also available from ZOLL Medical Corporation.

External pacemakers, defibrillators and other medical monitors designed for ambulatory and/or long-term use have further improved the ability to timely detect and treat life-threatening conditions. For example, certain medical devices operate by continuously or substantially continuously monitoring the patient's heart through one or more sensing electrodes for treatable arrhythmias and, when such is detected, the device applies corrective electrical pulses directly to the heart through one or more therapy electrodes.

SUMMARY

In one example, a patient-worn arrhythmia monitoring and treatment device includes a pair of therapy electrodes configured to be worn continuously by the patient for an extended period of time and at least one pair of sensing electrodes disposed proximate to skin of the patient. The at least one pair of sensing electrodes is configured to continually sense at least one ECG signal of the patient over the extended period of time. The device includes a therapy delivery circuit coupled to the pair of therapy electrodes and configured to deliver one or more therapeutic pulses to the patient through the pair of therapy electrodes. A controller coupled to therapy delivery circuit is configured to analyze the at least one ECG signal of the patient and detect one or more treatable arrhythmias based on the at least one ECG signal. The controller is configured to cause the therapy delivery circuit to deliver the one or more therapeutic pulses to the patient on detecting the one or more treatable arrhythmias. In examples, at least one of the one or more therapeutic pulses are formed as a biphasic waveform delivering within 15 percent of 360 J of energy to a body of the patient for a patient body having a transthoracic impedance in a range from about 20 to about 200 ohms. In examples, the one or more treatable arrhythmias comprise at least one of a ventricular fibrillation and a ventricular tachycardia.

In some examples, the patient-worn arrhythmia monitoring and treatment device further includes selectable energy levels, and the delivered one or more therapeutic pulses do not vary from 360 J of energy by more than 15 percent at any selected energy level. In other examples, the patient-worn arrhythmia monitoring and treatment device further includes selectable energy levels, and the delivered one or more therapeutic pulses is no less than 85 percent of 360 J at any selected energy level. In still other examples, the patient-worn arrhythmia monitoring and treatment device further comprises selectable energy levels, and the delivered energy ranges from about 360 J to 414 J at any selected energy level.

In examples of the device, the controller is further configured to detect the transthoracic impedance of the body of the patient and determine a charge voltage for delivering the one or more therapeutic pulses within 15 percent of 360 J. In some examples, the controller is further configured to determine the charge voltage based on a look up table associating the charge voltage with the detected transthoracic impedance. In other examples, the controller is further configured to determine the charge voltage based on one or more hard coded instructions associating the charge voltage with the detected transthoracic impedance.

In some examples, the device further includes a boost converter circuit configured to deliver the one or more therapeutic pulses within 15 percent of 360 J regardless of transthoracic impedance of the body of the patient.

In examples, the device further includes a source of electrical energy storing and providing at least 360 J of energy to the therapy delivery circuit, and the biphasic waveform can be a biphasic truncated exponential pulse. The biphasic truncated exponential pulse has a first pulse segment and a second pulse segment, and a selected amount of the provided energy is applied to the patient during the first pulse segment and a remaining amount of the provided energy is applied to the patient during the second pulse segment. In some examples, the therapy delivery circuit further includes an H-bridge to produce the first pulse segment and the second pulse segment of the biphasic truncated exponential pulse. In examples, the therapy delivery circuit is configured to truncate the provided energy being delivered to the body of a patient when the provided energy delivered to the body of the patient is substantially equal to 360 J. In other examples, the biphasic waveform can be a rectilinear biphasic waveform.

In examples, the device further includes a pulse voltage monitor, a pulse current monitor, and a timer for measuring a pulse voltage and a pulse current over a predetermined time period.

In implementations, the device further includes a garment configured to be worn about a torso of the patient, and at least one of the pair of therapy electrodes and the at least one pair of sensing electrodes are supported by the garment. In some examples, the at least one of the pair of therapy electrodes and the at least one pair of sensing electrodes are integrated with the garment. In some examples of the device including a garment, a source of electrical energy stores and provides at least 360 J of energy to the therapy delivery circuit, and the source of electrical energy and the therapy delivery circuit are supported by the garment. In some examples, the source of electrical energy can be a plurality of capacitors, and the plurality of capacitors can be distributed about and integrated into the garment.

In some examples of the device, the at least one of the pair of therapy electrodes and at least one sensing electrode of the at least one pair of sensing electrodes are disposed on a patch configured to be adhesively coupled to a torso of the patient for a term of not more than 14 days.

In some examples of the device, the pair of therapy electrodes and the at least one pair of sensing electrodes are disposed on a pair of patches configured to be adhesively coupled to a torso of the patient. In implementations, each of the pair of patches includes one therapy electrode of the pair of therapy electrodes and at least one sensing electrode of the at least one pair of sensing electrodes.

In examples, the device further includes gel deployment circuitry for reducing an impedance between each therapy electrode of the pair of therapy electrodes and the patient's skin.

In other examples, a patient-worn arrhythmia monitoring and treatment device includes a garment configured to be worn about a torso of a patient, a pair of therapy electrodes, and at least one pair of sensing electrodes configured to monitor at least one ECG signal of the patient. The device also includes a therapy delivery circuit coupled to the pair of therapy electrodes and configured to deliver one or more therapeutic pulses to the patient through the therapy electrodes. A plurality of capacitors are operably connected to the therapy delivery circuit and integrated into the garment. The plurality of capacitors are configured to store energy for at least one therapeutic pulse. The device further includes a controller coupled to the therapy delivery circuit and configured to analyze the at least one ECG signal of the patient and detect one or more treatable arrhythmias based on the at least one ECG signal. The controller is configured to cause the therapy delivery circuit to deliver the one or more therapeutic pulses to the patient on detecting the one or more treatable arrhythmia. The at least one of the one or more therapeutic pulses are formed as a biphasic waveform delivering within 15 percent of 360 J of energy to a body of the patient for a patient body having a transthoracic impedance in a range from about 20 to about 200 ohms.

In examples, the plurality of integrated capacitors are distributed about the garment.

In some examples of the device, the pair of therapy electrodes and the at least one pair of sensing electrodes are supported by the garment, and the garment is configured to be worn continuously by the patient for an extended period of time. In other examples, the pair of therapy electrodes or the at least one pair of sensing electrodes are supported by the garment, and the garment is configured to be worn continuously by the patient for an extended period of time.

In examples, the plurality of capacitors are integrated into separate regions of the garment.

In examples, the plurality of capacitors are nested in a stacked configuration.

In examples, the device further includes a rechargeable battery configured to be removably coupled to the plurality of capacitors.

In examples, the device further includes a rechargeable battery for powering the plurality of capacitors, and the garment removably couples to the rechargeable battery.

In some examples, at least one of the plurality of capacitors is contoured to conform to a silhouette of the patient. In some implementations, at least one of the plurality of capacitors has a thickness of between 1 mm and 40 mm.

In examples, the biphasic waveform comprises a biphasic truncated exponential pulse, and the biphasic truncated exponential pulse has a first pulse segment and a second pulse segment. In some examples, the device further includes an H-bridge to produce the first pulse segment and the second pulse segment of the biphasic truncated exponential pulse. A first portion of electrical energy stored in the plurality of capacitors is applied to the patient in the first pulse segment, and a second amount of electrical energy stored in the plurality of capacitors is applied to the patient during the second pulse segment.

In some examples, the device further includes a patient notification signal, and, in response to detecting the one or more treatable arrhythmias, the controller is configured to prompt the patient to respond to indicate that the patient is conscious. In examples, in an absence of a response from the patient indicating that the patient is conscious, the controller is configured to cause the therapy delivery circuit to deliver the one or more therapeutic pulses to the patient.

In examples, the plurality of capacitors includes at least 2 capacitors, and the controller is further configured to select a subset of the plurality of capacitors and deliver the one or more therapeutic pulses to the patient using the subset.

In other examples of the device, the plurality of capacitors includes 4 capacitors.

In still yet another example, a patient-worn arrhythmia monitoring and treatment device includes a garment configured to be worn about a torso of a patient, a pair of therapy electrodes, and at least one pair of sensing electrodes configured to monitor at least one ECG signal of the patient. The device includes a therapy delivery circuit coupled to the pair of therapy electrodes and configured to deliver one or more therapeutic pulses to the patient through the therapy electrodes. The device also includes a plurality of capacitors operably connected to the therapy delivery circuit and distributed about and integrated into the garment, the plurality of capacitors being configured to store energy for at least one therapeutic pulse. The device includes a controller coupled to therapy delivery circuit and configured to analyze the at least one ECG signal of the patient and detect one or more treatable arrhythmias based on the at least one ECG signal. The controller is configure to cause the therapy delivery circuit to deliver the one or more therapeutic pulses to the patient on detecting the one or more treatable arrhythmias. In examples, at least one of the one or more therapeutic pulses is formed as a biphasic waveform delivering 360 J to 575 J of energy to a body of the patient for a patient body having a transthoracic impedance in a range from about 20 to about 200 ohms.

BRIEF DESCRIPTION OF THE DRAWINGS

Various aspects of at least one example are described below with reference to the accompanying figures, which are not intended to be drawn to scale. The figures are included to provide an illustration and a further understanding of the various aspects and examples, and are incorporated in and constitute a part of this specification, but are not intended to limit the scope of the disclosure. The drawings, together with the remainder of the specification, serve to explain principles and operations of the described and claimed aspects and examples. In the figures, each identical or nearly identical component that is illustrated in various figures is represented by a like numeral. For purposes of clarity, not every component may be labeled in every figure.

FIGS. 4A-D are data tables of values in accordance with embodiments of the present disclosure.

FIGS. 11A-B are data tables of values in accordance with embodiments of the present disclosure.

FIG. 20A depicts an embodiment of a schematic diagram of electrical components of a patient-worn medical device.

FIG. 20B depicts an embodiment of a portion of the schematic diagram of FIG. 20A.

FIG. 20C is a data table of values in accordance with the embodiments of FIG. 20A.

FIGS. 21A-B are data tables of values in accordance with embodiments of the present disclosure.

DETAILED DESCRIPTION

Overview

Figure 1:
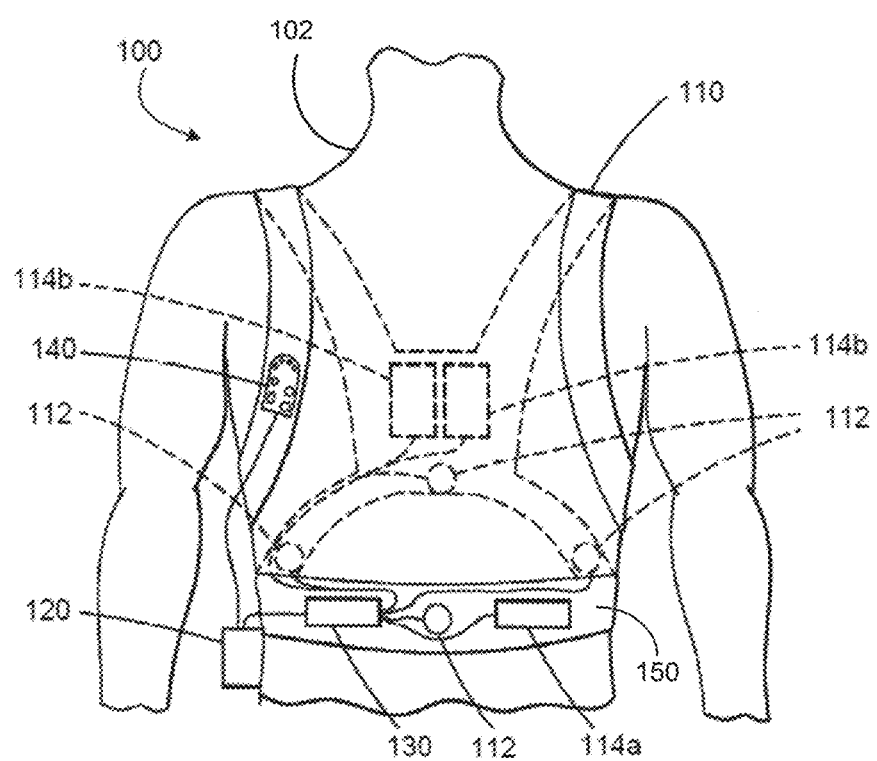
FIG. 1 depicts an example of a patient-worn medical device.

Normally, electrochemical activity within a human heart causes the organ's muscle fibers to contract and relax in a synchronized manner. This synchronized action of the heart's musculature results in the effective pumping of blood from the ventricles to the body's vital organs. In the case of ventricular fibrillation (VF), however, abnormal electrical activity within the heart causes the individual muscle fibers to contract in an unsynchronized and chaotic way. As a result of this loss of synchronization, the heart loses its ability to effectively pump blood. Defibrillators produce a large current pulse that disrupts the chaotic electrical activity of the heart associated with ventricular fibrillation and provides the heart's electrochemical system with the opportunity to re-synchronize itself. Once organized electrical activity is restored, synchronized muscle contractions usually follow, leading to the restoration of effective cardiac pumping.

Transthoracic defibrillation has become the primary therapy for cardiac arrest, ventricular tachycardia (VT), and ventricular fibrillation (VF). Monophasic waveforms dominated until around 1996, when the first biphasic waveform became available for clinical use. While biphasic waveforms have shown improved efficacy relative to monophasic defibrillation, there is still significant room for improvement: shock success rate for ventricular fibrillation (VF) remains less than 70-80 percent even with the most recent biphasic technology.

Various theories exist as to the causes of defibrillation success: e.g., energy delivered; average first phase current; peak current; pulse duration; and maintenance of the current level throughout the duration of the shock. Variability in the transthoracic impedance of a patient, however, can significantly impact all these aspects of the therapeutic defibrillation waveform resulting in a degradation of shock efficacy.

One approach taken is if a shock fails to defibrillate, for instance at a 200 joule energy setting, then the rescuer may manually increase the energy setting of the defibrillator to, for instance, 360 joules. Alternatively, the defibrillator itself may automatically increment the energy setting in a predetermined protocol for each successive shock up to a predetermined maximum energy setting available on the device, for instance 360 joules.

The problem of transthoracic impedance variability is particularly acute in the setting of wearable cardioverter defibrillators (WCD), such as the ZOLL LifeVest® wearable cardioverter defibrillator available from ZOLL Medical Corporation (Chelmsford, Mass.). In the WCD setting, a patient typically wears the device continuously, including defibrillation electrodes, for extended periods of time ranging from, for example, 24 hours, a week, two weeks, a month, three months, or more, as compared to a typical emergency cardiac resuscitation by emergency medical personnel which might only last for 15-20 minutes. Studies have shown that delivering a shock within a minute of a ventricular fibrillation results in higher rates of treatment success. Thus, if a WCD is unable to maintain a delivered maximum energy across the wide range of impedances encountered with varying patients and conditions, it may result in either delayed or ineffective defibrillation. Even if the defibrillation pulse is eventually successful with repeated shocks, if the defibrillation shocks are less effective and more shocks are required, the delay of not treating a patient immediately can result in lasting neurological impact or other long-term complications.

The present disclosure addresses the challenges and heretofore unaddressed problem of effectively treating patients by delivering high energy pulses, e.g., pulses that are each within 15 percent of 360 joules to 480 joules (e.g., a range of around 300 joules to around 575 joules), regardless of transthoracic impedance. In some implementations, the high energy pulses are each within 10 percent of 360 joules to 480 joules (e.g., a range of around 324 joules to around 528 joules), regardless of transthoracic impedance. In some implementations, the high energy pulses are each within 5 percent of 360 joules to 480 joules (e.g., a range of around 342 joules to around 456 joules), regardless of transthoracic impedance. By consistently delivering high energy pulses within 15 percent of 360 J of energy (or any joule level setting greater than 300 J and up to and including 575 joules) to any patient regardless of impedance, a medical treatment device can effectively treat a detected cardiac arrhythmia with fewer energy pulse deliveries. This more efficient treatment may avoid physical trauma associated with repeated energy shocks and delayed restoration of a normal sinus rhythm.

This disclosure relates to a patient-worn arrhythmia monitoring and treatment device that detects one or more treatable arrhythmias based on an ECG signal. In embodiments, the patient-worn arrhythmia monitoring device delivers one or more therapeutic pulses each formed as a biphasic waveform delivering within 15 percent of 360 J of energy to the body of the patient, regardless of transthoracic impedance. This disclosure relates to embodiments of a treatment device that deliver 360 J of energy to the body of a patient having a transthoracic impedance ranging from about 20 to about 200 ohms. In some implementations, embodiments of the present disclosure deliver treatment by first measuring (e.g., calculating) transthoracic patient impedance and in other implementations, embodiments of the present disclosure deliver treatment without first measuring (e.g., calculating) transthoracic patient impedance.

This disclosure also relates to embodiments of a garment for an arrhythmia monitoring and treatment device. The garment is configured to be worn about a torso of a patient, and integrated into the garment are a plurality of energy storage units operably connected to a therapy delivery circuit. The plurality of energy storage units may be located in one housing and/or compartment of the garment, or distributed about the garment so as to create an ergonomic distribution of the storage units. The energy storage units are configured to store energy for at least one therapeutic pulse delivered to the patient by a pair of therapy electrodes coupled to the therapy delivery circuit. The at least one therapeutic pulse is formed as a biphasic waveform delivering within 15 percent of 360 J of energy to the body of the patient for a patient body having a transthoracic impedance in a predetermined range, e.g., from about 20 to about 200 ohms.

In some implementations, embodiments of the present disclosure deliver treatment by first measuring (e.g., calculating) transthoracic patient impedance and in other implementations, embodiments of the present disclosure deliver treatment without first measuring (e.g., calculating) transthoracic patient impedance.

Example Medical Devices

The teachings of the present disclosure can be generally applied to external medical monitoring and treatment devices (e.g., devices that are not completely implanted within the patient's body). External medical devices can include, for example, ambulatory medical devices that are capable of and designed for moving with the patient as the patient goes about his or her daily routine. An example ambulatory medical device can be a wearable medical device such as a wearable cardioverter defibrillator (WCD), a wearable cardiac monitoring device, an in-hospital device such as an in-hospital wearable defibrillator, a short-term wearable cardiac monitoring and/or therapeutic device, mobile telemetry devices, and other similar wearable medical devices.

The wearable medical device can be capable of continuous use by the patient. In some implementations, the continuous use can be substantially or nearly continuous in nature. That is, the wearable medical device may be continuously used, except for sporadic periods during which the use temporarily ceases (e.g., while the patient bathes, while the patient is refit with a new and/or a different garment, while the battery is charged/changed, while the garment is laundered, etc.). Such substantially or nearly continuous use as described herein may nonetheless qualify as continuous use. In some implementations, the patient may remove the wearable medical device for a short portion of the day (e.g., for half an hour to bathe).

Further, the wearable medical device can be configured as a long term or extended use medical device. Such devices can be configured to be used by the patient for an extended period of 24 hours or more, several days, weeks, months, or even years. Accordingly, the extended use can be uninterrupted until a physician or other caregiver provides specific prescription to the patient to stop use of the wearable medical device. For example, the wearable medical device can be prescribed for use by a patient for an extended period of at least one week. In an example, the wearable medical device can be prescribed for use by a patient for an extended period of at least 30 days. In an example, the wearable medical device can be prescribed for use by a patient for an extended period of at least one month. In an example, the wearable medical device can be prescribed for use by a patient for an extended period of at least two months. In an example, the wearable medical device can be prescribed for use by a patient for an extended period of at least three months. In an example, the wearable medical device can be prescribed for use by a patient for an extended period of at least six months. In an example, the wearable medical device can be prescribed for use by a patient for an extended period of at least one year.

Regardless of the extended period of wear, the use of the wearable medical device can include continuous or nearly continuous wear by the patient as described above. For example, the continuous use can include continuous wear or attachment of the wearable medical device to the patient. In implementations, the continuous attachment is through one or more of the electrodes as described herein during both periods of monitoring and periods when the device may not be monitoring the patient but is otherwise still worn by or otherwise attached to the patient. Continuous use can include continuously monitoring the patient while the patient is wearing the device for cardiac-related information (e.g., electrocardiogram (ECG) information, including arrhythmia information, heart vibrations, etc.) and/or non-cardiac information (e.g., blood oxygen, the patient's temperature, glucose levels, tissue fluid levels, and/or lung vibrations). For example, the wearable medical device can carry out its continuous monitoring and/or recording in periodic or aperiodic time intervals or times (e.g., every few minutes, hours, once a day, once a week, or other interval set by a technician or prescribed by a caregiver). Alternatively or additionally, the monitoring and/or recording during intervals or times can be triggered by a user action or another event.

As noted above, the wearable medical device can be configured to monitor other physiologic parameters of the patient in addition to cardiac related parameters. For example, the wearable medical device can be configured to monitor, for example, lung vibrations (e.g., using microphones and/or accelerometers), breath vibrations, sleep related parameters (e.g., snoring, sleep apnea), and tissue fluids (e.g., using radio-frequency transmitters and sensors), among others.

Other example wearable medical devices include automated cardiac monitors and/or defibrillators for use in certain specialized conditions and/or environments such as in combat zones or within emergency vehicles. Such devices can be configured so that they can be used immediately (or substantially immediately) in a life-saving emergency. In some examples, the wearable medical devices described herein can be pacing-enabled, and, therefore, capable of providing therapeutic pacing pulses to the patient.

In implementations, an example therapeutic medical device can include an in-hospital continuous monitoring defibrillator and/or pacing device such as, for example, an in-hospital wearable defibrillator. In such an example, the electrodes can be adhesively attached to the patient's skin. For example, the electrodes can include disposable adhesive electrodes. For example, the electrodes can include sensing and therapy components disposed on separate sensing and therapy electrode adhesive patches. In some implementations, both sensing and therapy components can be integrated and disposed on a same electrode adhesive patch that is then attached to the patient. In an example implementation, the electrodes can include a front adhesively attachable therapy electrode, a back adhesively attachable therapy electrode, and a plurality of adhesively attachable sensing electrodes. For example, the front adhesively attachable therapy electrode attaches to the front of the patient's torso to deliver pacing or defibrillating therapy. Similarly, the back adhesively attachable therapy electrode attaches to the back of the patient's torso. In an example scenario, at least three ECG adhesively attachable sensing electrodes can be attached to at least above the patient's chest near the right arm, above the patient's chest near the left arm, and towards the bottom of the patient's chest in a manner prescribed by a trained professional.

A patient being monitored by an in-hospital defibrillator and/or pacing device may be confined to a hospital bed or room for a significant amount of time (e.g., 90 percent or more of the patient's stay in the hospital). As a result, a user interface can be configured to interact with a user other than the patient (e.g., a nurse, a technician, a home caretaker, a patient care representative, etc.) for device-related functions such as initial device baselining, setting and adjusting patient parameters, and changing the device batteries.

In implementations, an example of a therapeutic medical device can include a short-term continuous monitoring defibrillator and/or pacing device, for example, a short-term outpatient wearable defibrillator. For example, such a short-term outpatient wearable defibrillator can be prescribed by a physician for patients presenting with syncope. A wearable defibrillator can be configured to monitor patients presenting with syncope by, for example, analyzing the patient's cardiac activity for aberrant patterns that can indicate abnormal physiological function. For example, such aberrant patterns can occur prior to, during, or after the onset of symptoms. In such an example implementation of the short-term wearable defibrillator, the electrode assembly can be adhesively attached to the patient's skin and have a similar configuration as the in-hospital defibrillator previously described.

FIG. 1 illustrates an example medical device 100 that is external, ambulatory, and wearable by a patient, and configured to implement one or more configurations described herein. For example, the medical device 100 can be a non-invasive medical device configured to be located substantially external to the patient. Such a medical device 100 can be, for example, an ambulatory medical device that is capable of and designed for moving with the patient as the patient goes about his or her daily routine. For example, the medical device 100 as described herein can be bodily-attached to the patient such as the LifeVest® wearable cardioverter defibrillator available from ZOLL® Medical Corporation. In one example scenario, such wearable defibrillators can be worn nearly continuously or substantially continuously for two to three months at a time. During the period of time for which the patient wears the wearable defibrillator, the wearable defibrillator can be configured to continuously or substantially continuously monitor the vital signs of the patient and, upon determination that treatment is required, can be configured to deliver one or more therapeutic electrical pulses to the patient. For example, such therapeutic shocks can be pacing, defibrillation, or transcutaneous electrical nerve stimulation (TENS) pulses.

The medical device 100 can include one or more of the following: a garment 110, one or more sensing electrodes 112 (e.g., ECG electrodes), one or more therapy electrodes 114a and 114b (collectively referred to as therapy electrodes 114), a medical device controller 120, a connection pod 130, a patient interface pod 140, a belt 150, or any combination of these. In some examples, at least some of the components of the medical device 100 can be configured to be affixed to the garment 110 (or in some examples, permanently integrated into the garment 110), which can be worn about the patient's torso. Additional implementations of sensing electrode arrangements and therapy electrode arrangements on a patient-worn medical device are provided herein in subsequent sections.

The medical device controller 120 can be operatively coupled to the sensing electrodes 112, which can be affixed to the garment 110, e.g., assembled into the garment 110 or removably attached to the garment, e.g., using hook and loop fasteners. In some implementations, the sensing electrodes 112 can be permanently integrated into the garment 110. The medical device controller 120 can be operatively coupled to the therapy electrodes 114. For example, the therapy electrodes 114 can also be assembled into the garment 110, or, in some implementations, the therapy electrodes 114 can be permanently integrated into the garment 110.

Component configurations other than those shown in FIG. 1 are possible. For example, the sensing electrodes 112 can be configured to be attached at various positions about the body 102 of the patient. The sensing electrodes 112 can be operatively coupled to the medical device controller 120 through the connection pod 130. In some implementations, the sensing electrodes 112 can be adhesively attached to the patient's body 102. In some implementations, the sensing electrodes 112 and at least one of the therapy electrodes 114 can be included on a single integrated patch and adhesively applied to the patient's body. Additional implementations of sensing electrode arrangements and therapy electrode arrangements on a patient-worn medical device are provided herein in subsequent sections.

The sensing electrodes 112 can be configured to detect one or more cardiac signals. Examples of such signals include ECG signals and/or other sensed cardiac physiological signals from the patient. In certain implementations, the sensing electrodes 112 can include additional components such as accelerometers, acoustic signal detecting devices, and other measuring devices for recording additional parameters. For example, the sensing electrodes 112 can also be configured to detect other types of patient physiological parameters and acoustic signals, such as tissue fluid levels, heart vibrations, lung vibrations, respiration vibrations, patient movement, etc. Example sensing electrodes 112 include a metal electrode with an oxide coating such as tantalum pentoxide electrodes.

In some examples, the therapy electrodes 114 can also be configured to include sensors configured to detect ECG signals as well as other physiological signals of the patient. The connection pod 130 can, in some examples, include a signal processor configured to amplify, filter, and digitize these cardiac signals prior to transmitting the cardiac signals to the medical device controller 120. One or more of the therapy electrodes 114 can be configured to deliver one or more therapeutic defibrillating shocks to the body 102 of the patient when the medical device 100 determines that such treatment is warranted based on the signals detected by the sensing electrodes 112 and processed by the medical device controller 120. Example therapy electrodes 114 can include conductive metal electrodes such as stainless steel electrodes that include, in certain implementations, one or more conductive gel deployment devices configured to deliver conductive gel to the metal electrode prior to delivery of a therapeutic shock.

Example Medical Device Controller

Figure 2:
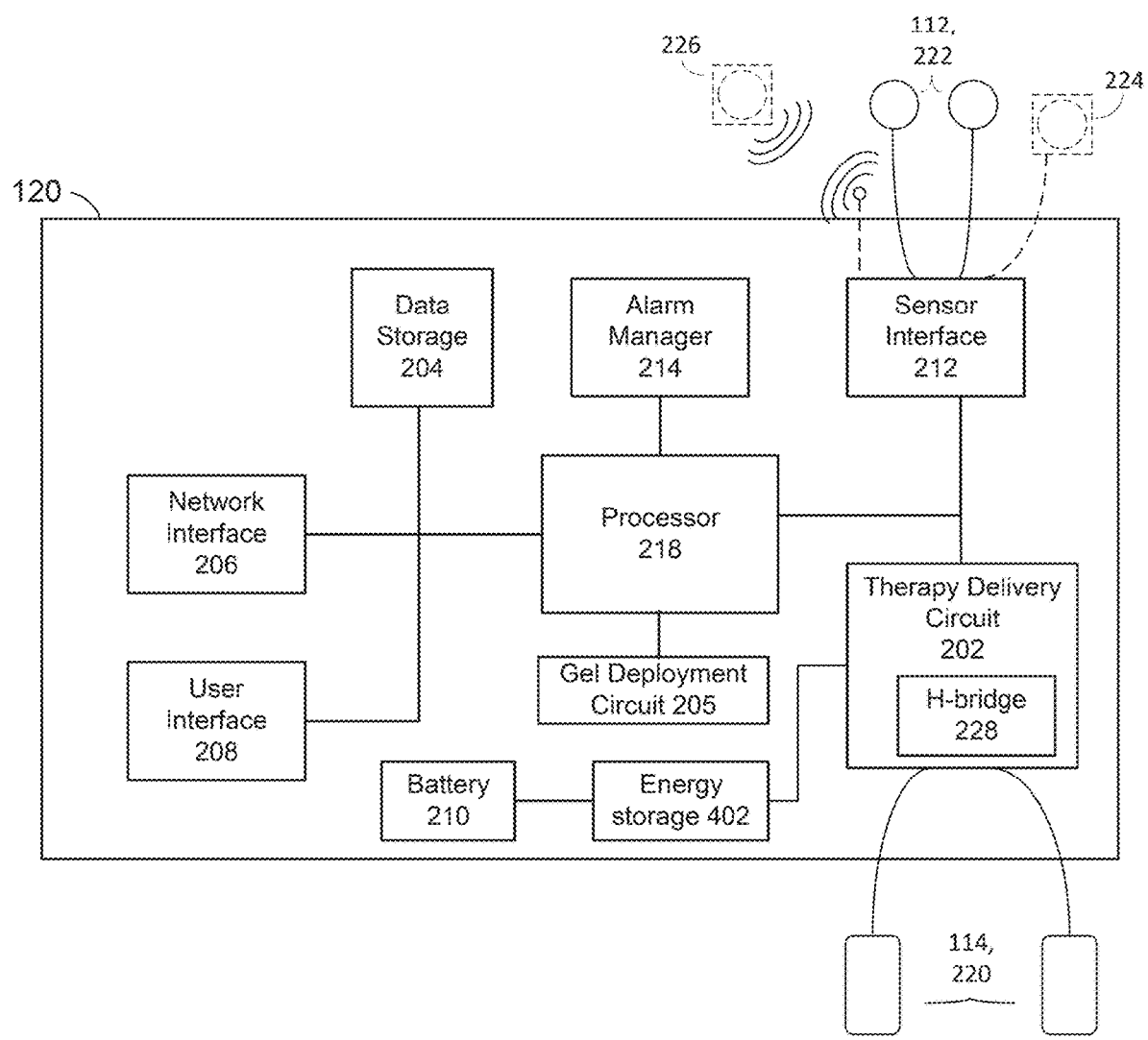
FIG. 2 depicts a schematic diagram of an embodiment of a medical device controller of a patient-worn medical device.

FIG. 2 illustrates a sample component-level view of the medical device controller 120. As shown in FIG. 2, the medical device controller 120 can include a therapy delivery circuit 202 including a polarity switching component such as an H-bridge 228, a data storage 204, a gel deployment circuit 205, a network interface 206, a user interface 208, at least one battery 210, a sensor interface 212, an alarm manager 214, and least one processor 218. A patient monitoring medical device can include a medical device controller 120 that includes like components as those described above, but does not include the therapy delivery circuit 202.

The therapy delivery circuit 202 can be coupled to one or more electrodes 220 configured to provide therapy to the patient (e.g., therapy electrodes 114 as described above in connection with FIG. 1). For example, the therapy delivery circuit 202 can include, or be operably connected to, circuitry components that are configured to generate and provide the therapeutic shock. The circuitry components can include, for example, resistors, one or more capacitors, relays and/or switches, an electrical bridge such as an H-bridge 228 (e.g., including a plurality of insulated gate bipolar transistors or IGBTs that deliver and truncate a therapy pulse, as described in further detail below), voltage and/or current measuring components, and other similar circuitry arranged and connected such that the circuitry work in concert with the therapy delivery circuit and under control of one or more processors (e.g., processor 218) to provide, for example, one or more pacing or defibrillation therapeutic pulses.

Pacing pulses can be used to treat cardiac arrhythmias such as bradycardia (e.g., in some implementations, less than 30 beats per minute) and tachycardia (e.g., in some implementations, more than 150 beats per minute) using, for example, fixed rate pacing, demand pacing, anti-tachycardia pacing, and the like. Defibrillation pulses can be used to treat ventricular tachycardia and/or ventricular fibrillation.

In implementations, the one or more capacitors include a parallel-connected capacitor bank consisting of one capacitor or a plurality of capacitors (e.g., two, three, four or more capacitors). These capacitors can be switched into a series connection during discharge for a defibrillation pulse. For example, four capacitors of approximately 500 uF can be used. In one implementation, the capacitors can have between 500 to 2500 volt surge rating and can be charged in approximately 5 to 30 seconds from a battery pack depending on the amount of energy to be delivered to the patient. Additional implementations of capacitor properties and arrangements on a patient-worn medical device are provided herein in subsequent sections.

For example, each defibrillation pulse can deliver between 300 to 575 joules (J) of energy. In some implementations, the defibrillating pulse can be a biphasic truncated exponential pulse, whereby the signal can switch between a positive and a negative portion (e.g., charge directions). This type of waveform can be effective at defibrillating patients at lower energy levels when compared to other types of defibrillation pulses (e.g., such as monophasic pulses). For example, an amplitude and a width of the two phases of the energy waveform can be automatically adjusted to deliver a predetermined energy amount (e.g., 306 J, 310 J, 320 J, 340 J, 350 J, 360 J, 370 J, 380 J, 390 J, 400 J, 410 J, 414 J, 452 J, 471 J, 480 J, 499 J, 503 J, 521 J, 535 J, 540 J, 547 J, 555 J, 560 J, 569 J, and 575 J) regardless of the patient's body impedance. The therapy delivery circuit 202 can be configured to perform the switching and pulse delivery operations, for example, under control of the processor 218. In some implementations, as the energy is delivered to the patient, the amount of energy being delivered can be tracked. For example, while the pulse is being delivered the amount of energy can be kept to a predetermined constant value even as the pulse waveform is dynamically controlled based on factors such as the patient's body impedance. Additional detailed implementations of energy delivery components of a patient-worn medical device are provided herein in subsequent sections.

In implementations, the gel deployment circuit 205 is coupled to the processor 218 and configured to cause the delivery of conductive gel immediately before delivery of the therapeutic shocks to the treatment site, or within a short time interval, for example, within about 1 second, 5 seconds, 10 seconds, 30 seconds, or one minute before delivery of the therapeutic shocks to the treatment site. The gel deployment circuit 205 may be coupled to or integrated within a therapy electrode 114 or other therapy delivery device as a single unit. When a treatable cardiac condition is detected and no patient response is received after device prompting, the gel deployment circuit 205 can be signaled to deploy the conductive gel.

The data storage 204 can include one or more of non-transitory computer readable media, such as flash memory, solid state memory, magnetic memory, optical memory, cache memory, combinations thereof, and others. The data storage 204 can be configured to store executable instructions and data used for operation of the medical device controller 120. In certain implementations, the data storage 204 can include executable instructions that, when executed, are configured to cause the processor 218 to perform one or more functions.

In some examples, the network interface 206 can facilitate the communication of information between the medical device controller 120 and one or more other devices or entities over a communications network. For example, where the medical device controller 120 is included in an ambulatory medical device (such as medical device 100), the network interface 206 can be configured to communicate with a remote computing device such as a remote server or other similar computing device. The network interface 206 can include communications circuitry for transmitting data in accordance with a Bluetooth® wireless standard for exchanging such data over short distances to an intermediary device(s), e.g., a base station, a "hotspot" device, a smartphone, tablet, a portable computing device, and/or other devices in proximity of the wearable medical device. The intermediary device(s) may in turn communicate the data to a remote server over a broadband cellular network communications link, The communications link may implement broadband cellular technology (e.g., 2.5G, 2.75G, 3G, 4G, 5G cellular standards) and/or Long-Term Evolution (LTE) technology or GSM/EDGE and UMTS/HSPA technologies for high-speed wireless communication. In some implementations, the intermediary device(s) may communicate with a remote server over a Wi-Fi™ communications link based on the IEEE 802.11 standard.

In certain implementations, the user interface 208 can include one or more physical interface devices such as input devices, output devices, and combination input/output devices and a software stack configured to drive operation of the devices. These user interface elements may render visual, audio, and/or tactile content. Thus the user interface 208 may receive input or provide output, thereby enabling a user to interact with the medical device controller 120.

The medical device controller 120 can also include at least one battery 210 configured to provide power to one or more components integrated in the medical device controller 120. The battery 210 can include a rechargeable multi-cell battery pack. In one example implementation, the battery 210 can include three or more 2200 mAh lithium ion cells that provide electrical power to the other device components within the medical device controller 120. For example, the battery 210 can provide its power output in a range of between 20 mA to 1000 mA (e.g., 40 mA) output and can support 24 hours, 48 hours, 72 hours, or more, of runtime between charges. In certain implementations, the battery capacity, runtime, and type (e.g., lithium ion, nickel-cadmium, or nickel-metal hydride) can be changed to best fit the specific application of the medical device controller 120.

The sensor interface 212 can be coupled to one or more sensors configured to monitor one or more physiological parameters of the patient. As shown, the sensors may be coupled to the medical device controller 120 via a wired or wireless connection. The sensors can include one or more electrocardiogram (ECG) electrodes 222 (e.g., similar to sensing electrodes 112 as described above in connection with FIG. 1), heart vibrations sensors 224, and tissue fluid monitors 226 (e.g., based on ultra-wide band radiofrequency devices).

The ECG electrodes 222 can monitor a patient's ECG information. For example, the ECG electrodes 222 can include conventional stick-on adhesive electrodes, conductive electrodes with stored gel deployment, e.g., metallic electrodes with stored conductive gel configured to be dispersed in the electrode-skin interface when needed, or dry electrodes, e.g., a metallic substrate with an oxide layer in direct contact with the patient's skin. The ECG electrodes 222 can be configured to measure the patient's ECG signals. The ECG electrodes 222 can transmit information descriptive of the ECG signals to the sensor interface 212 for subsequent analysis.

The vibration sensors 224 can include heart vibration sensors to detect a patient's heart vibration information. For example, the vibrations sensors 224 can be configured to detect heart vibration values including any one or all of S1, S2, S3, and S4. From these heart vibration values, certain electromechanical metrics may be calculated, including any one or more of electromechanical activation time (EMAT), percentage of EMAT (% EMAT), systolic dysfunction index (SDI), and left ventricular systolic time (LVST). The vibrations sensors 224 can include an acoustic sensor configured to detect vibrations from a subject's cardiac system and provide an output signal responsive to the detected heart vibrations. The vibrations sensors 224 can also include a multi-channel accelerometer, for example, a three channel accelerometer configured to sense movement in each of three orthogonal axes such that patient movement/body position can be detected. The vibrations sensors 224 can transmit information descriptive of the heart vibrations information or patient position/movement to the sensor interface 212 for subsequent analysis.

The tissue fluid monitors 226 can use radio frequency (RF) based techniques to assess fluid levels and accumulation in a patient's body tissue. For example, the tissue fluid monitors 226 can be configured to measure fluid content in the lungs, typically for diagnosis and follow-up of pulmonary edema or lung congestion in heart failure patients. The tissue fluid monitors 226 can include one or more antennas configured to direct RF waves through a patient's tissue and measure output RF signals in response to the waves that have passed through the tissue. In certain implementations, the output RF signals include parameters indicative of a fluid level in the patient's tissue. The tissue fluid monitors 226 can transmit information descriptive of the tissue fluid levels to the sensor interface 212 for subsequent analysis.

The sensor interface 212 can be coupled to any one or combination of sensing electrodes/other sensors to receive other patient data indicative of patient parameters. Once data from the sensors has been received by the sensor interface 212, the data can be directed by the processor 218 to an appropriate component within the medical device controller 120. For example, if heart data is collected by heart vibrations sensor 224 and transmitted to the sensor interface 212, the sensor interface 212 can transmit the data to the processor 218 which, in turn, relays the data to a cardiac event detector. The cardiac event data can also be stored on the data storage 204.

In certain implementations, the alarm manager 214 can be configured to manage alarm profiles and notify one or more intended recipients of events specified within the alarm profiles as being of interest to the intended recipients. These intended recipients can include external entities such as users (patients, physicians, and monitoring personnel) as well as computer systems (monitoring systems or emergency response systems). The alarm manager 214 can be implemented using hardware or a combination of hardware and software. For instance, in some examples, the alarm manager 214 can be implemented as a software component that is stored within the data storage 204 and executed by the processor 218. In this example, the instructions included in the alarm manager 214 can cause the processor 218 to configure alarm profiles and notify intended recipients using the alarm profiles. In other examples, alarm manager 214 can be an application-specific integrated circuit (ASIC) that is coupled to the processor 218 and configured to manage alarm profiles and notify intended recipients using alarms specified within the alarm profiles. Thus, examples of alarm manager 214 are not limited to a particular hardware or software implementation.

In some implementations, the processor 218 includes one or more processors (or one or more processor cores) that each are configured to perform a series of instructions that result in manipulated data and/or control the operation of the other components of the medical device controller 120. In some implementations, when executing a specific process (e.g., cardiac monitoring), the processor 218 can be configured to make specific logic-based determinations based on input data received, and be further configured to provide one or more outputs that can be used to control or otherwise inform subsequent processing to be carried out by the processor 218 and/or other processors or circuitry with which processor 218 is communicatively coupled. Thus, the processor 218 reacts to a specific input stimulus in a specific way and generates a corresponding output based on that input stimulus. In some example cases, the processor 218 can proceed through a sequence of logical transitions in which various internal register states and/or other bit cell states internal or external to the processor 218 may be set to logic high or logic low. The processor 218 can be configured to execute a function stored in software. For example, such software may be stored in a data store coupled to the processor 218 and configured to cause the processor 218 to proceed through a sequence of various logic decisions that result in the function being executed. The various components that are described herein as being executable by the processor 218 can be implemented in various forms of specialized hardware, software, or a combination thereof. For example, the processor can be a digital signal processor (DSP) such as a 24-bit DSP processor. The processor can be a multi-core processor, e.g., having two or more processing cores. The processor can be an Advanced RISC Machine (ARM) processor such as a 32-bit ARM processor. The processor can execute an embedded operating system, and include services provided by the operating system that can be used for file system manipulation, display & audio generation, basic networking, firewalling, data encryption and communications.

Patient-Worn Medical Device for Delivering High Energy Pulses

Embodiments of the patient-worn medical device of the present disclosure effectively treat patients by delivering into the patient one or more therapeutic pulses of high energy such as within 15 percent of 360 J regardless of the patient's transthoracic impedance. As described above, studies have shown that delivering a shock within a minute of a ventricular fibrillation results in higher rates of treatment success. Thus, if a WCD is unable to maintain a delivered maximum energy across the wide range of impedances encountered with varying patients and conditions, delayed or entirely ineffective defibrillation may result. Even if the defibrillation is eventually successful with repeated shocks, if the defibrillation shocks are less effective and more shocks are required, the delay of not treating a patient immediately can result in lasting neurological impact or other long-term complications.

This disclosure relates to a patient-worn arrhythmia monitoring and treatment device that detects one or more treatable arrhythmias based on an ECG signal. The patient-worn arrhythmia monitoring device delivers one or more therapeutic pulses each formed as a high energy biphasic waveform delivering, e.g., within 15 percent of 360 J to 480 J of energy to the body of the patient, regardless of transthoracic impedance. This disclosure relates to embodiments of a treatment device that deliver high energy pulses to the body of a patient having a transthoracic impedance ranging from about 20 to about 200 ohms.

This disclosure also relates to embodiments of a garment for an arrhythmia monitoring and treatment device. The garment is configured to be worn about a torso of a patient, and distributed about and integrated into the garment are a plurality of energy storage units operably connected to a therapy delivery circuit. The energy storage units are configured to store energy for at least one therapeutic pulse delivered to the patient by a pair of therapy electrodes coupled to the therapy delivery circuit. The at least one therapeutic pulse is formed as a high energy biphasic waveform delivering, for example, within 15 percent of 360 J to 480 J of energy to the body of the patient for a patient body having a transthoracic impedance in a range from about 20 to about 200 ohms.

As described above with reference to FIG. 1, a patient-worn arrhythmia monitoring and treatment device 100 is configured to be worn by a patient for an extended period of time. In implementations, the patient-worn therapy device 100 includes a pair of therapy electrodes 114a, 114b and at least one pair of sensing electrodes 112a, 112b disposed proximate to the skin of the patient and configured to continually sense at least one ECG signal of the patient over the extended period of time. In implementations, continual sensing is uninterrupted, continuous sensing. In implementations, continual sensing is substantially continuous sensing, with infrequent and/or ephemeral interruptions attributable to one or more of the at least one pair of sensing electrodes losing contact momentarily with the skin. In implementations, continual sensing is continuous or substantially continuous sensing occurring while the patient is wearing the therapy device 100 and not while the patient removes the therapy device 100 for short duration activities such as maintenance or bathing, for example.

The patient-worn arrhythmia monitoring and treatment device 100 further includes a therapy delivery circuit 202 coupled to the pair of therapy electrodes 114a, 114b, 220 and is configured to deliver one or more therapeutic pulses to the patient through the therapy electrodes 114a, 114b, 220. As described above with reference to FIG. 2, in implementations, the therapy delivery circuit 202 is included in a medical device controller 120. FIG. 2 illustrates a sample component-level view of an implementation of the medical device controller 120. As shown in the embodiment of FIG. 2, the medical device controller 120 includes a therapy delivery circuit 202 including a polarity switching component such as an H-bridge 228, a data storage 204, a network interface 206, a user interface 208, at least one battery 210, a sensor interface 212, an alarm manager 214, and least one processor 218.

The processor 218 is coupled to the therapy delivery circuit 202 and configured to analyze the at least one ECG signal of the patient and detect one or more treatable arrhythmias based on the at least one ECG signal. On detecting a treatable arrhythmia, such as for example ventricular fibrillation or ventricular tachycardia, the controller 120 causes the therapy delivery circuit 202 to deliver one or more therapeutic pulses of energy to the patient. In implementations, the one or more therapeutic pulses are formed as biphasic waveforms delivering within 15 percent of 360 Joules (J) of energy to the body 102 of the patient having a transthoracic impedance (TTI) in a range of about 20 ohms to 200 ohms.

The range of energy delivered into the patient body 102 is in accordance with IEC standard 60601-2-4 IEC which requires the following limits: The measured DELIVERED ENERGY into these load resistances shall not vary from the DELIVERED ENERGY for that impedance by more than ±3 J or ±15 percent, whichever is greater, at any energy level. In implementations, the patient-worn arrhythmia monitoring and treatment device includes selectable energy levels. In implementations, a patient or care provider may select the energy level through a user interface 208 of the medical device controller 120 which may include buttons, dials, voice command interface, or touch screen selection menus. In implementations, a patient or care provider may select the energy level through a remote user interface in wired or wireless communication with the medical device controller 120, such as a smart phone app or a computer portal. In implementations, the medical device controller 120 relies on sensor information to detect transthoracic impedance (TTI) of the patient body and automatically selects the energy level to a value capable of delivering into the patient body within 15 percent of 360 J of energy. In implementations, the delivered energy does not vary from, for example, 360 J of energy, by more than 15 percent at any selected energy level. In implementations, the delivered energy is no less than 85 percent of 360 J at any selected energy level. In implementations, the delivered energy level ranges from about 360 J to 414 J at any selected energy level. In implementations, the delivered energy level ranges from about 306 J to 414 J at any selected energy level. In implementations in which the device is configured to deliver high energy pulses within 15 percent of 480 joules, the selected energy level can range from about 300 J to 575 J.

In implementations, each therapy electrode of the at least one pair of therapy electrodes 114, 114a, 114b, 220 has a conductive surface adapted for placement adjacent the patient's skin and has an impedance reducing means, e.g. an impedance reducing conductive gel, contained therein for reducing the impedance between a therapy electrode and the patient's skin. In implementations, the patient-worn arrhythmia monitoring and treatment device 100 may include gel deployment circuitry (e.g., the gel deployment circuit 205 of FIG. 2) configured to cause the delivery of conductive gel substantially proximate to a treatment site (e.g., a surface of the patient's skin in contact with the therapy electrode 114) prior to delivering therapeutic shocks to the treatment site. As described in U.S. Pat. No. 9,008,801, titled "WEARABLE THERAPEUTIC DEVICE," issued on Apr. 14, 2015 (hereinafter the "'801 Patent"), which is hereby incorporated herein by reference in its entirety, the gel deployment circuitry may be configured to cause the delivery of conductive gel immediately before delivery of the therapeutic shocks to the treatment site, or within a short time interval, for example, within about 1 second, 5 seconds, 10 seconds, 30 seconds, or one minute before delivery of the therapeutic shocks to the treatment site. Such gel deployment circuitry, for example the gel deployment circuit 205 of FIG. 2, may be coupled to or integrated within a therapy electrode or other therapy delivery device as a single unit. When a treatable cardiac condition is detected and no patient response is received after device prompting, the gel deployment circuitry can be signaled to deploy the conductive gel. In some examples, the gel deployment circuitry may be constructed as one or more separate and independent gel deployment modules. Such modules may be configured to receive removable and/or replaceable gel cartridges (e.g., cartridges that contain one or more conductive gel reservoirs). As such, the gel deployment circuitry may be permanently disposed in the garment as part of the therapy delivery systems, while the cartridges may be removable and/or replaceable.

In some implementations, the gel deployment modules may be implemented as gel deployment packs and include at least a portion of the gel deployment circuitry along with one or more gel reservoirs within the gel deployment pack. In such implementations, the gel deployment pack, including the one or more gel reservoirs and associated gel deployment circuitry may be removable and/or replaceable. In other examples, the gel deployment pack, including the one or more gel reservoirs and associated gel deployment circuitry, and the therapy electrode can be integrated into a therapy electrode assembly that can be removed and replaced as a single unit either after use, or if damaged or broken.

Example Patient-Worn Medical Device Circuitry

In implementations, the therapy delivery circuit 202 can include, or be operably connected to, circuitry components that are configured to generate and provide the therapeutic shock. The circuitry components can include, for example, resistors, one or more capacitors, relays and/or switches, an electrical bridge such as an H-bridge 228 (e.g., including a plurality of switches, such as for example, insulated gate bipolar transistors or IGBTs, silicon carbide field effect transistors (SiC FETs), metal-oxide semiconductor field effect transistors (MOSFETS), silicon-controlled rectifiers (SCRs), or other high current switching devices), voltage and/or current measuring components, and other similar circuitry components arranged and connected such that the circuitry components work in concert with the therapy delivery circuit and under control of one or more processors (e.g., processor 218) to provide, for example, one or more pacing or defibrillation therapeutic pulses.

Figure 3:
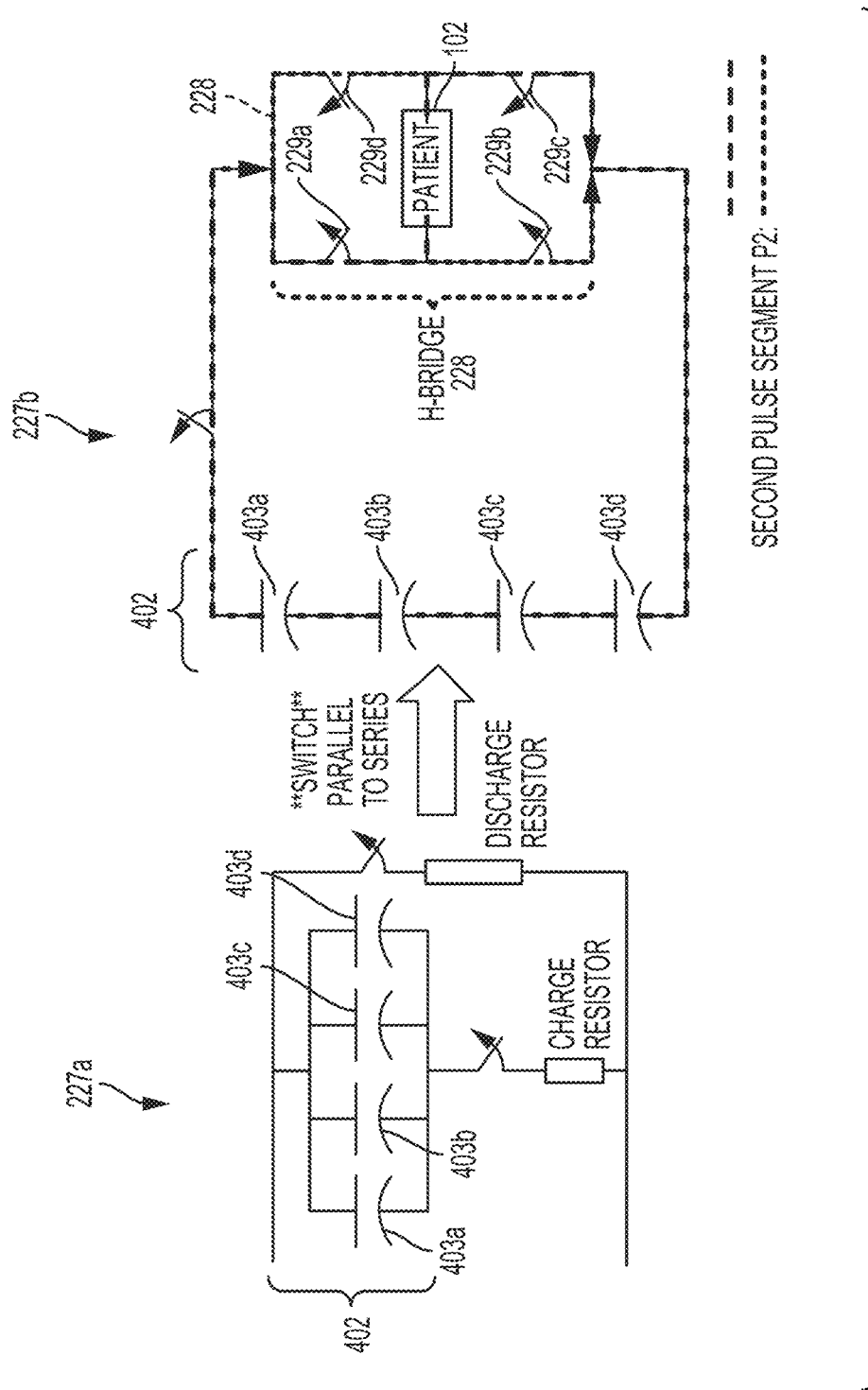
FIG. 3 depicts a schematic diagram of an embodiment of electrical components of a medical device controller of a patient-worn medical device.

In implementations, the patient-worn arrhythmia monitoring and treatment device 100 further includes a source of electrical energy that stores and provides at least 360 J to 480 J of energy to the therapy delivery circuit 202. The one or more therapeutic pulses are defibrillation pulses of electrical energy, and the one or more treatable arrhythmias include ventricular fibrillation and ventricular tachycardia. In implementations, the one or more therapeutic pulses are biphasic exponential pulses. Such therapeutic pulses may be generated by charging one or more capacitors and discharging the energy stored in the one or more capacitors into the patient. For example, the therapy delivery circuit 202 can include one or more power converters for controlling the charging and discharging of the capacitors. In some implementations, the discharge of energy from the capacitors may be controlled by, for example, an H-bridge 228 depicted in FIG. 3. The H-bridge 228 of FIG. 3 is a circuit that controls the discharge of energy into the patient body 102 like the H-bridge circuit described in U.S. Pat. No. 6,280,461, titled "PATIENT-WORN ENERGY DELIVERY APPARATUS," issued on Aug. 28, 2001 (hereinafter the "'461 patent"), and U.S. Pat. No. 8,909,335, titled "METHOD AND APPARATUS FOR APPLYING A RECTILINEAR BIPHASIC POWER WAVEFORM TO A LOAD," issued on Dec. 9, 2014 (hereinafter the "'335 patent"), each of which is hereby incorporated herein by reference in its entirety.

As shown in the embodiment to FIG. 3, the H-bridge 228 is electrically coupled to an energy storage module 402 including four capacitors 403a, 403b, 403c, 403d charged in parallel at a preparation phase 227a and discharged in series at a treatment phase 227b. In some implementations, the energy storage module 402 can include more or fewer than four capacitors. During the treatment phase 227b, the H-bridge applies a therapeutic pulse that causes current to flow through the body 102 of the patient in desired directions for desired durations. The H-bridge 228 includes H-bridge switches 229a, 229b, 229c, 229d opened and closed selectively by a switching transistor such as insulated gate bipolar transistors (IGBTs), silicon carbide field effect transistors (SiC FETs), metal-oxide semiconductor field effect transistors (MOSFETS), silicon-controlled rectifiers (SCRs), or other high current switching devices. Switching a pair of transistors to a closed position, for example switches 229a and 229c, enables current to flow in a first direction for first pulse segment P1. Opening switches 229a and 229c and closing switches 229b and 229d enables current to flow through the body 102 of the patient in a second pulse segment P2 directionally opposite the flow of the first pulse segment P1.

FIGS. 4A through 4D provide values for the energy storage module 402 having one or more capacitors 403a-403d that deliver within 15 percent of 360 J of energy into the body 102 of a patient, and FIGS. 5-10 depict example biphasic exponential waveforms 300a-300f delivering within 15 percent of 360 J of high energy pulses across a range of transthoracic impedances. Unlike devices having a 360 J energy "setting" but delivering less than 360 J of energy into the body of a patient, using the techniques and circuits described herein, the device 100 can be designed and programmed to actually deliver, for example, within 15 percent of 360 J of energy into the body 102 of the patient regardless of impedance. For example, within 15 percent of 360 J of energy is delivered to any patient having any TTI value 320a-320d (also referenced throughout and in the figures collectively as R and TTI 320) ranging from 20 ohms up to and including 200 ohms. In one embodiment, the source of electrical energy is an energy storage module 402 that includes one or more capacitors 403a-403d (also referenced throughout and in the figures collectively as 403 and a number of capacitors N) rated for energy settings of about 300 J to 575 J and configured to deliver at least within 15 percent of 360 J into the body of the patient. In implementations, the capacitors 403 deliver a pulse of delivered energy 325a-325d (also referenced throughout and in the figures collectively as E(d) and 325) into the body of a patient accordance with the following relationships:

$$T = \frac{-\ln\left(1 - \frac{E(d)}{E(s)}\right)RC}{2}$$

$$E(s) = \frac{1}{2} * CV^2 * N$$

$$Ipeak = N * (V/R)$$

$$Imin = Ipeak * e^{-\left(\frac{T}{RC}\right)}$$

$$Iavg = (Ipeak + Imin)/2$$

As indicated in the implementations of FIGS. 4A through 4D, C is the capacitance 305a-305d (collectively and interchangeably referred to as 305) of each capacitor 403 of the energy storage module 402 in microfarads. V is the voltage 310a-310d (also referenced throughout and in the figures collectively as 310) of each capacitor 403a-403d of the energy storage module 402 necessary for delivering 360 J of energy 325. E(s) is the stored energy value 315a-315d (also referenced throughout and in the figures collectively as 315) of the energy storage module 402 in Joules. R is the value of transthoracic impedance (TTI) 320 of the patient in ohms. E(d) is the energy delivered 325a-325d into the body of the patient. T is the duration 330a-330d (also referenced throughout and in the figures collectively as 330) in milliseconds of the biphasic pulse required to deliver within 15 percent of 360 J of energy. Ipeak is the peak current value 333a-333d (also referenced throughout and in the figures collectively as 333) of the biphasic pulse in amps. Imin is the minimum absolute current value 335a-335d (also referenced throughout and in the figures collectively as 335) in amps, and Iavg is the average current value 337a-337d (also referenced throughout and in the figures collectively as 337) in amps over the duration T of the treatment pulse delivering within 15 percent of 360 J of energy into the body of the patient. N is the number of capacitors 302a-302d (also referenced throughout and in the figures collectively as quantity of capacitors 302 and number of capacitors 302) in the energy storage module 402.

As indicated in the tabulated data of FIGS. 4A through 4D and example biphasic exponential waveforms 300a-f of FIGS. 5-10, the pulse width Pw, or duration 330, of each waveform and the peak current value 333, minimum current value 335 and average current value 337 adjust to accommodate varying and various patient impedance values 320. In implementations, the patient-worn arrhythmia monitoring and treatment device 100 further includes a pulse voltage monitor, a pulse current monitor and a timer for measuring the pulse voltage and the pulse current over the duration 330 of the pulse. As transthoracic impedance 320 increases, the overall pulse width Pw, or duration 330, increases, and the current values (e.g., Ipeak 333, Imin 335, and Iavg 337) all decrease. As transthoracic impedance 320 increases, the patient-worn arrhythmia monitoring and treatment device 100 applies energy into the body 102 of the patent for a longer duration T with lower current values (e.g., Ipeak 333, Imin 335, and Iavg 337). In implementations, the ratio of the duration of the second pulse segment P2 to the first pulse segment decreases as patient impedance values 320 increase. In implementations, the stored energy value E(s) 315 of the energy storage module 402 is the amount of energy the therapy delivery circuit 202 requires to produce a delivered energy E(d) 325 of within 15 percent of 360 J into the body of the patient for the pulse width duration 330. In some implementations, the minimum current Imin 335 is maintained above a rheobase current, e.g., a predetermined minimum current value 335, of 4 A, and the pulse width duration 330 is preferably maintained above a predetermined minimum value of 4 ms.

As indicated in the example tabulated values of FIGS. 4A through 4D, the patient-worn arrhythmia monitoring and treatment device 100 includes one or more capacitors 403, such as the capacitors 403a-403d of FIG. 3. Each of the one or more capacitors 403, has a same microfarad value of capacitance 305. In some implementations, the capacitors 403 may have different capacitance values 305a-305d.

In FIG. 4A, the patient-worn arrhythmia monitoring and treatment device 100 has a capacitor quantity 302e, or number of capacitors N, of one. In FIG. 4B, the patient-worn arrhythmia monitoring and treatment device 100 has a capacitor quantity 302f, or number of capacitors N, of two. In FIG. 4C, patient-worn arrhythmia monitoring and treatment device 100 has a capacitor quantity 302g, or number of capacitors N, of three, and in FIG. 4D, the patient-worn arrhythmia monitoring and treatment device 100 has a capacitor quantity 302h, or number of capacitors N, of four. In the examples of FIGS. 4A-4D, each capacitor 403a-403d has a capacitance 305 of 500 microfarads.

By varying the voltage 310 across the one or more capacitors 403 the processor 218 of the patient-worn arrhythmia monitoring and treatment device 100 varies the stored energy E(s) 315 in relation to transthoracic patient impedance values 320 so that the energy delivered 325, into a body of any impedance value ranging from 25 ohms to 200 ohms is within 15 percent of 360 J.

Additionally, in implementations, such as those of FIGS. 4A-4D, predetermined design considerations include completing the therapeutic pulse within a predetermined time period, or duration 330, ranging from about 4 milliseconds to 22 milliseconds while keeping the minimum current Imin 335 above 4 A across all impedance values 320. Advantages relating to applying a defibrillation pulse within a predetermined time interval 330 of about 4 ms to 22 ms and above a rheobase current, or minimum current value 335, of about 4 A are detailed in numerous clinical studies. For example, the following publications support these design considerations for successful defibrillation, each of which is incorporated herein in their entireties: Kroll MW. A minimal model of the single capacitor biphasic defibrillation waveform. PACE 1994; 17(Pt. I):1782-1792; Irnich W. Optimal Truncation of Defibrillation Pulses. PACE 1995; 18[Pt. I]:673-688; Shorofsky et al. Effect of Second-Phase Duration on the Strength-Duration Relation for Human Transvenous Defibrillation. Circulation. 2000; 102:2239-2242.

As depicted in the implementations of FIGS. 5 through 10, the therapeutic pulses formed as biphasic exponential waveforms 300a-300f include a first pulse segment P1 and a second pulse segment P2. The controller applies a first selected amount of electrical energy to the body 102 of the patient during the first pulse segment P1, and the remaining, second amount of the selected amount of electrical energy is applied to the body 102 of the patient during the second pulse segment P2. In implementations, the H-bridge 228 produces the first pulse segment P1 and the second pulse segment P2 by initiating the delivery of energy into the body 102 of the patient at the start of the first pulse segment P1, reversing polarity of current flow at the start of the second pulse segment P2, and truncating the energy delivery at the completion of the second pulse segment P2 when the energy delivered to the body 102 of the patient is substantially equal to 360 J. For example, the energy pulse is truncated when the energy delivered into the body 102 of the patient is within 15 percent of 360 J.

Figure 5:
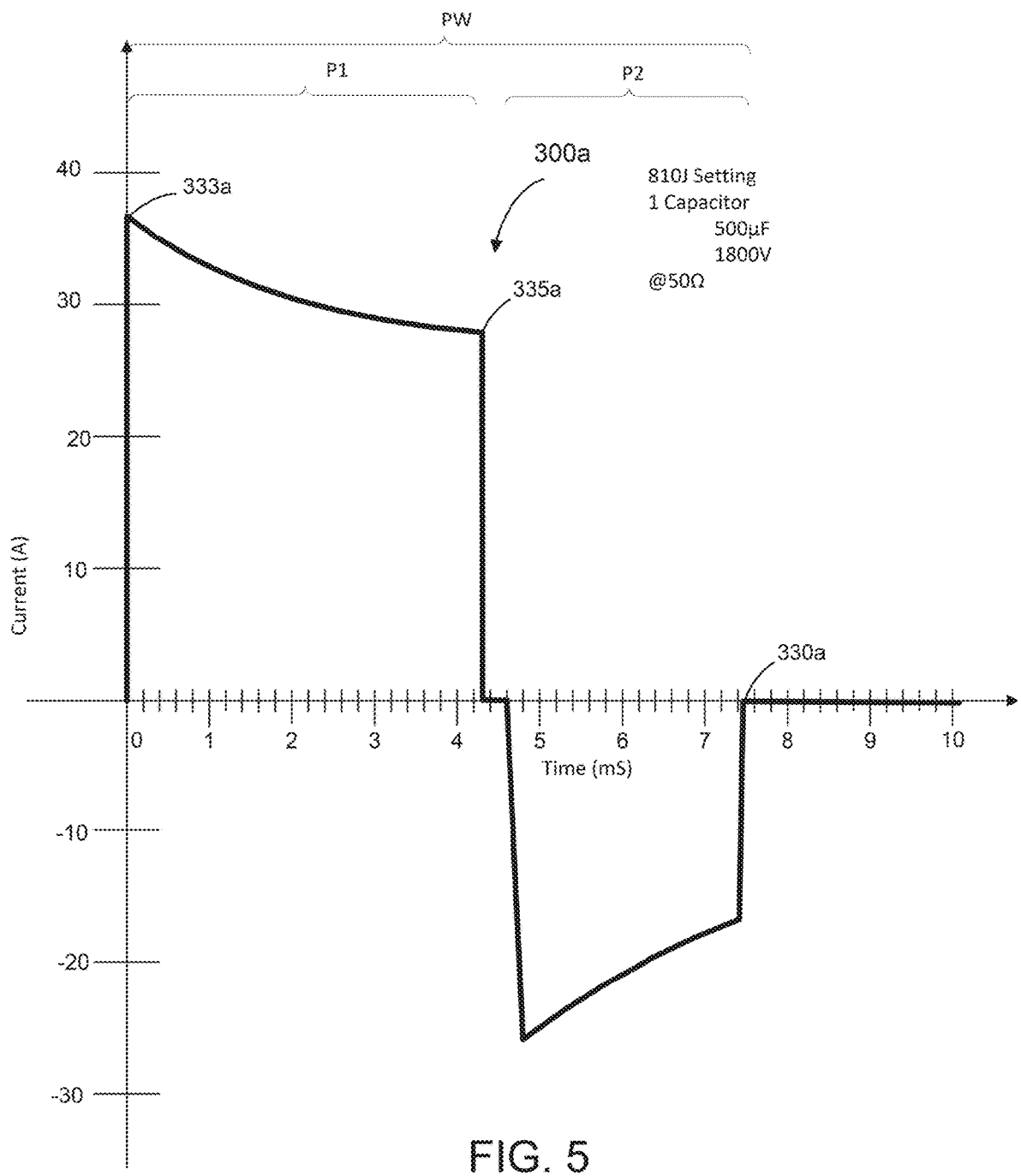
FIG. 5 is a schematic diagram of an embodiment of a waveform for a patient-worn medical device treating a patient having a transthoracic impedance of 50 ohms.

The biphasic exponential waveform 300a of FIG. 5 corresponds to values in FIG. 4A for a patient-worn arrhythmia monitoring and treatment device 100 having a single capacitor (e.g. a number of capacitors N 302a of one) and a delivered energy E(d) 325a of 360 J for a patient having an impedance 320a of 50 Ohms. The capacitor has a voltage 310a of 1800V. The capacitors are charged to a stored energy 315a of 810 J, and the patient-worn arrhythmia monitoring and treatment device 100 delivers a therapeutic pulse over a total pulse width Pw, or duration 330a, of 7.3 ms. The biphasic exponential waveform 300a is split across a first pulse segment P1 that starts at a peak current 333a of 36 A and truncates at a minimum current 335a of 26.8 A and a second pulse segment P2 that truncates at 7.3 ms with the delivery of 360 J. The first pulse segment P1 and second pulse segment P2 of the biphasic exponential waveform 300a have an average current 337a of 31.4 A.

Figure 6:
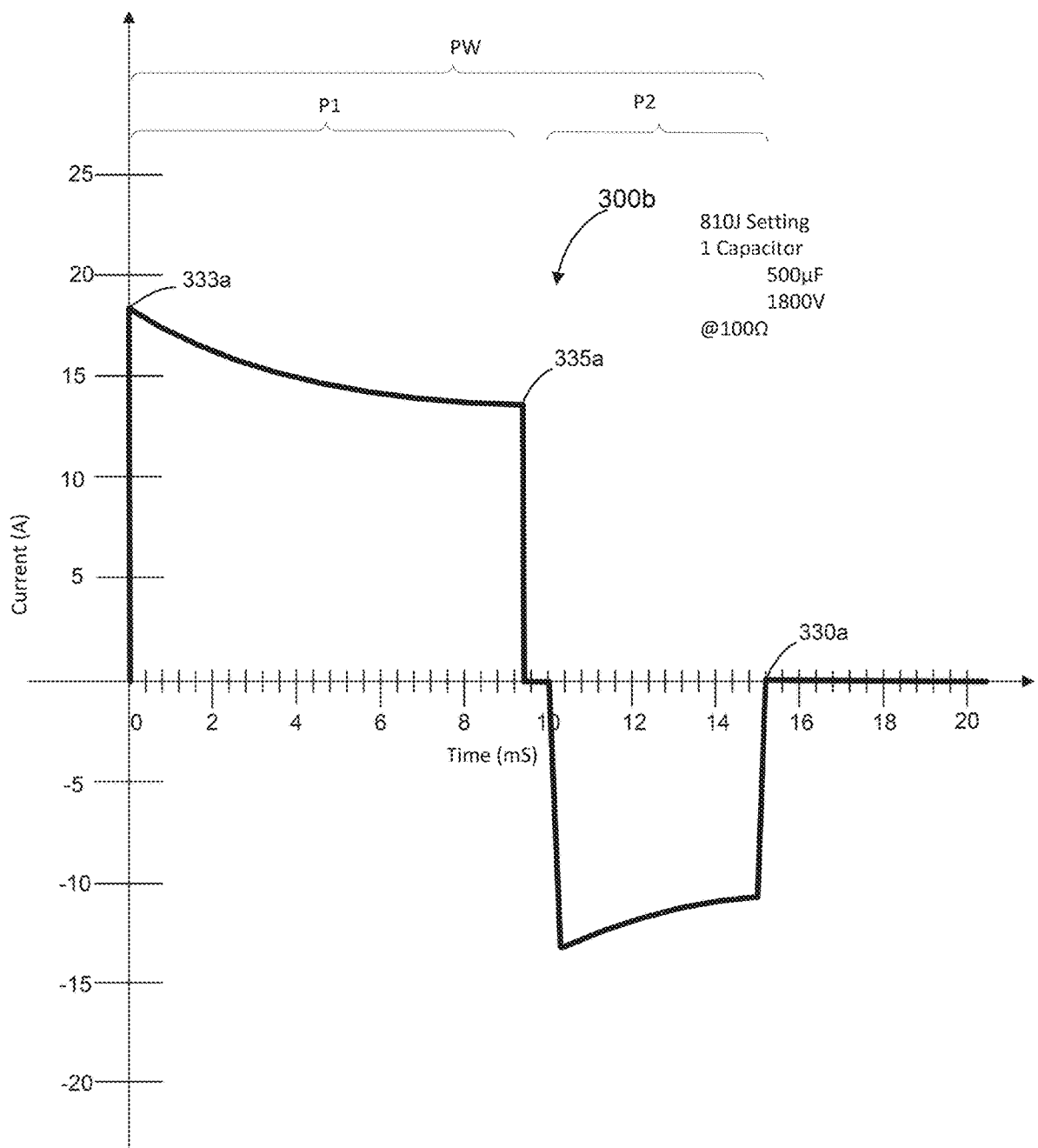
FIG. 6 is a schematic diagram of an embodiment of a waveform for a patient-worn medical device treating a patient having a transthoracic impedance of 100 ohms.

The biphasic exponential waveform 300b of FIG. 6 corresponds to values in FIG. 4A for a patient-worn arrhythmia monitoring and treatment device 100 having a single capacitor (e.g. a number of capacitors 302a of one) and an delivered energy 325a of 360 J for a patient having an impedance 320a of 100 Ohms. The capacitors have a voltage 310a of 1800V. The capacitors are charged to a stored energy 310a of 810 J, and the patient-worn arrhythmia monitoring and treatment device 100 delivers a therapeutic pulse over a total pulse width Pw, or duration 330a, of 14.7 ms. The biphasic exponential waveform 300b is split across a first pulse segment P1 that starts at a peak current 333a of 18 A and truncates at a minimum current 335a of 13.4 A and a second pulse segment P2 that truncates at 14.7 ms with the delivery of 360 J. The first pulse segment P1 and second pulse segment P2 of the biphasic exponential waveform 300b have an average current 337a of 15.7 A.

Figure 7:
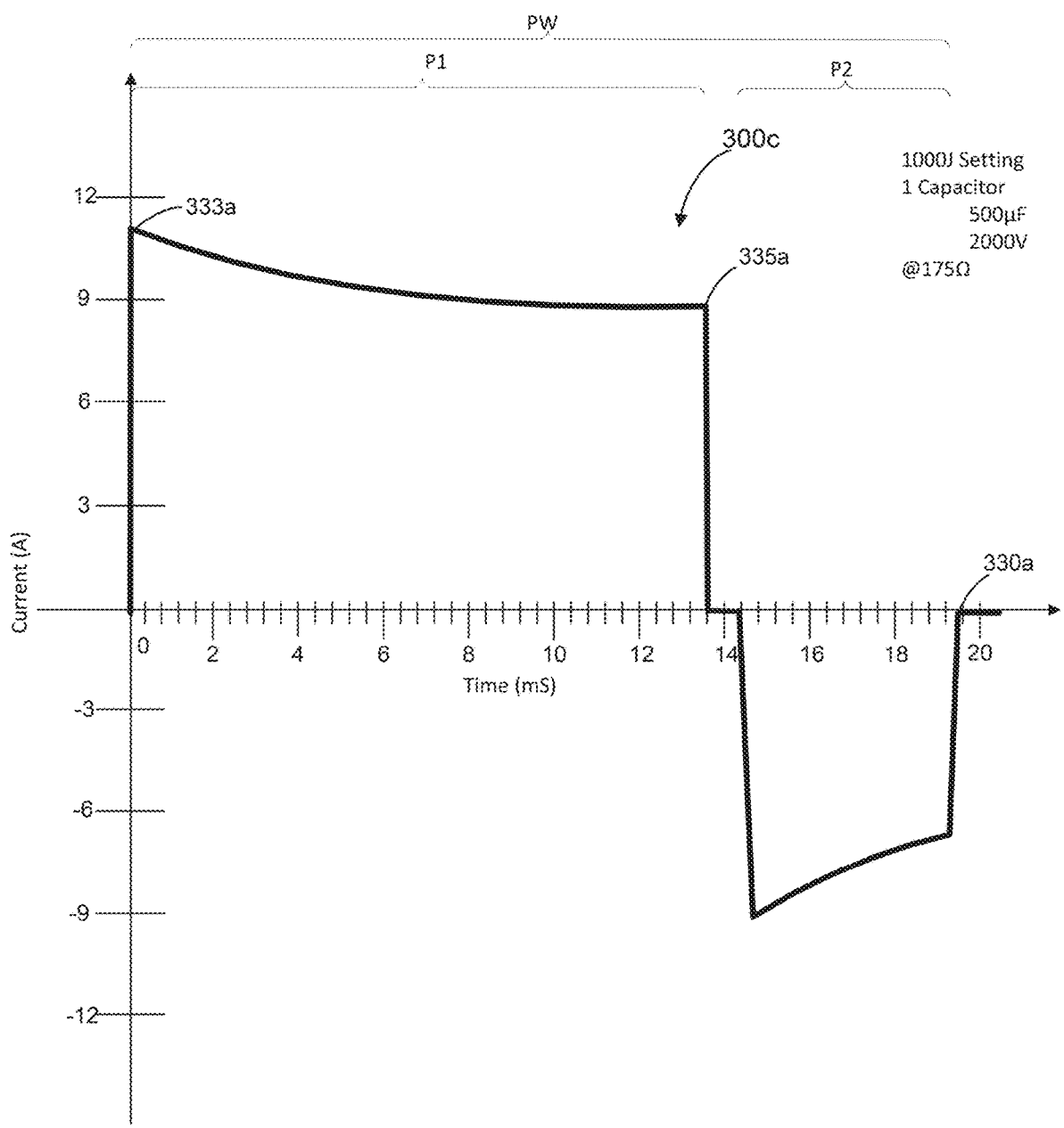
FIG. 7 is a schematic diagram of an embodiment of a waveform for a patient-worn medical device treating a patient having a transthoracic impedance of 175 ohms.

The biphasic exponential waveform 300c of FIG. 7 corresponds to values in FIG. 4A for a patient-worn arrhythmia monitoring and treatment device 100 having a single capacitor (e.g. a number of capacitors 302a of one) and an delivered energy 325a of 360 J for a patient having an impedance 320a of 175 Ohms. The capacitors have a voltage 310a of 2000V. The capacitors are charged to a stored energy 310a of 1000 J, and the patient-worn arrhythmia monitoring and treatment device 100 delivers a therapeutic pulse over a total pulse width Pw, or duration 330a, of 19.5 ms. The biphasic exponential waveform 300c is split across a first pulse segment P1 that starts at a peak current 333a of 11.4 A and truncates at a minimum current 335a of 9.1 A and a second pulse segment P2 that truncates at 19.5 ms with the delivery of 360 J. The first pulse segment P1 and second pulse segment P2 of the biphasic exponential waveform 300c have an average current 337a of 10.3 A.

Figure 8:
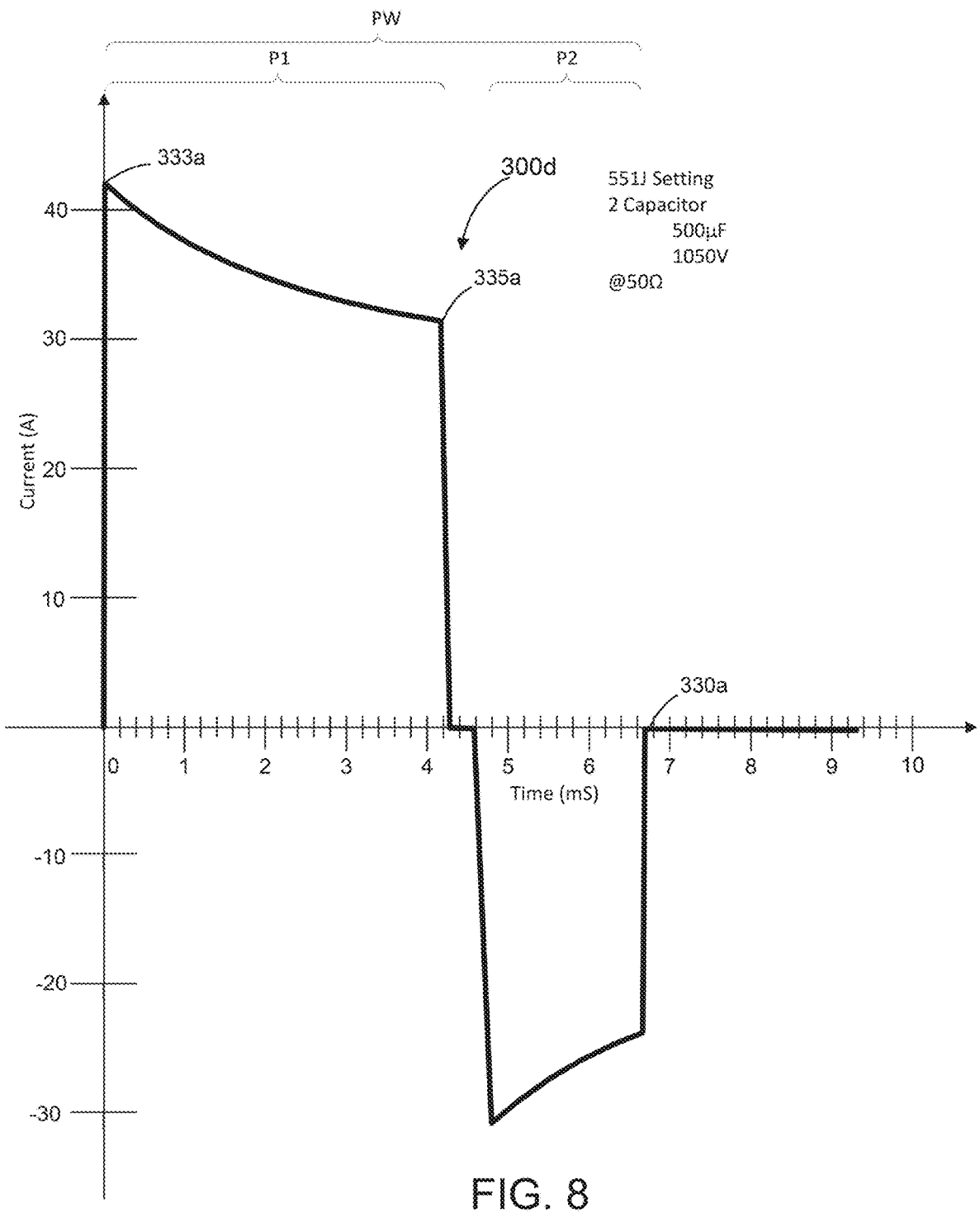
FIG. 8 is a schematic diagram of an embodiment of a waveform for a patient-worn medical device treating a patient having a transthoracic impedance of 50 ohms.

The biphasic exponential waveform 300d of FIG. 8 corresponds to values in FIG. 4B for a patient-worn arrhythmia monitoring and treatment device 100 having two capacitors (e.g. a number of capacitors 302b of two) and an delivered energy 325b of 360 J for a patient having an impedance 320b of 50 Ohms. The capacitors have a voltage 310b of 1050V. The capacitors are charged to a stored energy 315b of 551 J, and the patient-worn arrhythmia monitoring and treatment device 100 delivers a therapeutic pulse over a total pulse width Pw, or duration 330b, of 6.6 ms. The biphasic exponential waveform 300d is split across a first pulse segment P1 that starts at a peak current 333b of 42 A and truncates at a minimum current 335b of 32.2 A and a second pulse segment P2 that truncates at 6.6 ms with the delivery of 360 J. The first pulse segment P1 and second pulse segment P2 of the biphasic exponential waveform 300d have an average current 337b of 37.1 A.

Figure 9:
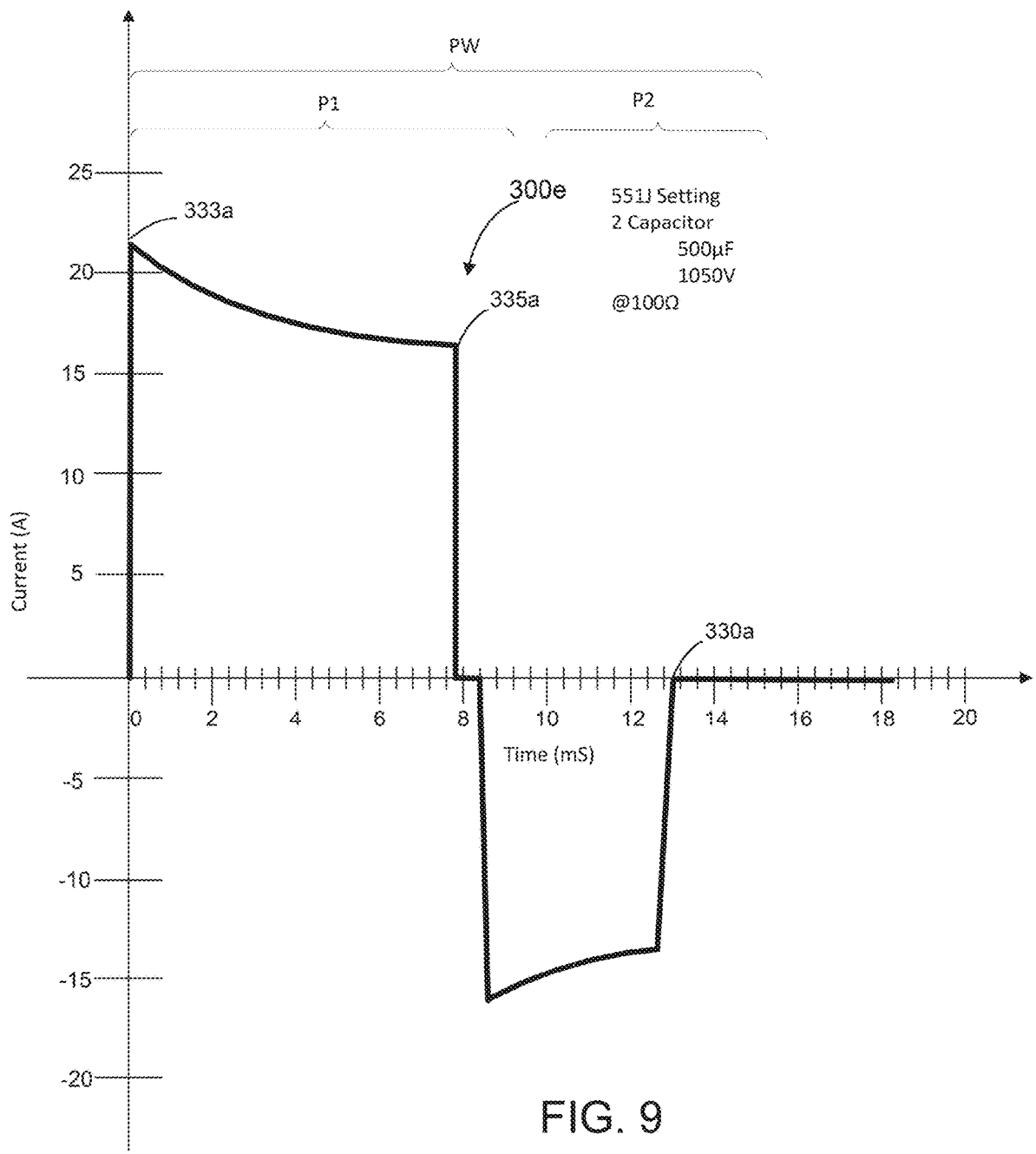
FIG. 9 is a schematic diagram of an embodiment of a waveform for a patient-worn medical device treating a patient having a transthoracic impedance of 100 ohms.

The biphasic exponential waveform 300e of FIG. 9 corresponds to values in FIG. 4B for a patient-worn arrhythmia monitoring and treatment device 100 having two capacitors (e.g. a number of capacitors 302b of two) and an delivered energy 325b of 360 J for a patient having an impedance 320b of 100 Ohms. The capacitors have a voltage 310b of 1050V. The capacitors are charged to a stored energy 310b of 551 J, and the patient-worn arrhythmia monitoring and treatment device 100 delivers a therapeutic pulse over a total pulse width Pw, or duration 330b, of 13.2 ms. The biphasic exponential waveform 300e is split across a first pulse segment P1 that starts at a peak current 333b of 21 A and truncates at a minimum current 335b of 16.1 A and a second pulse segment P2 that truncates at 6.6 ms with the delivery of 360 J. The first pulse segment P1 and second pulse segment P2 of the biphasic exponential waveform 300e have an average current 337b of 18.6 A.

Figure 10:
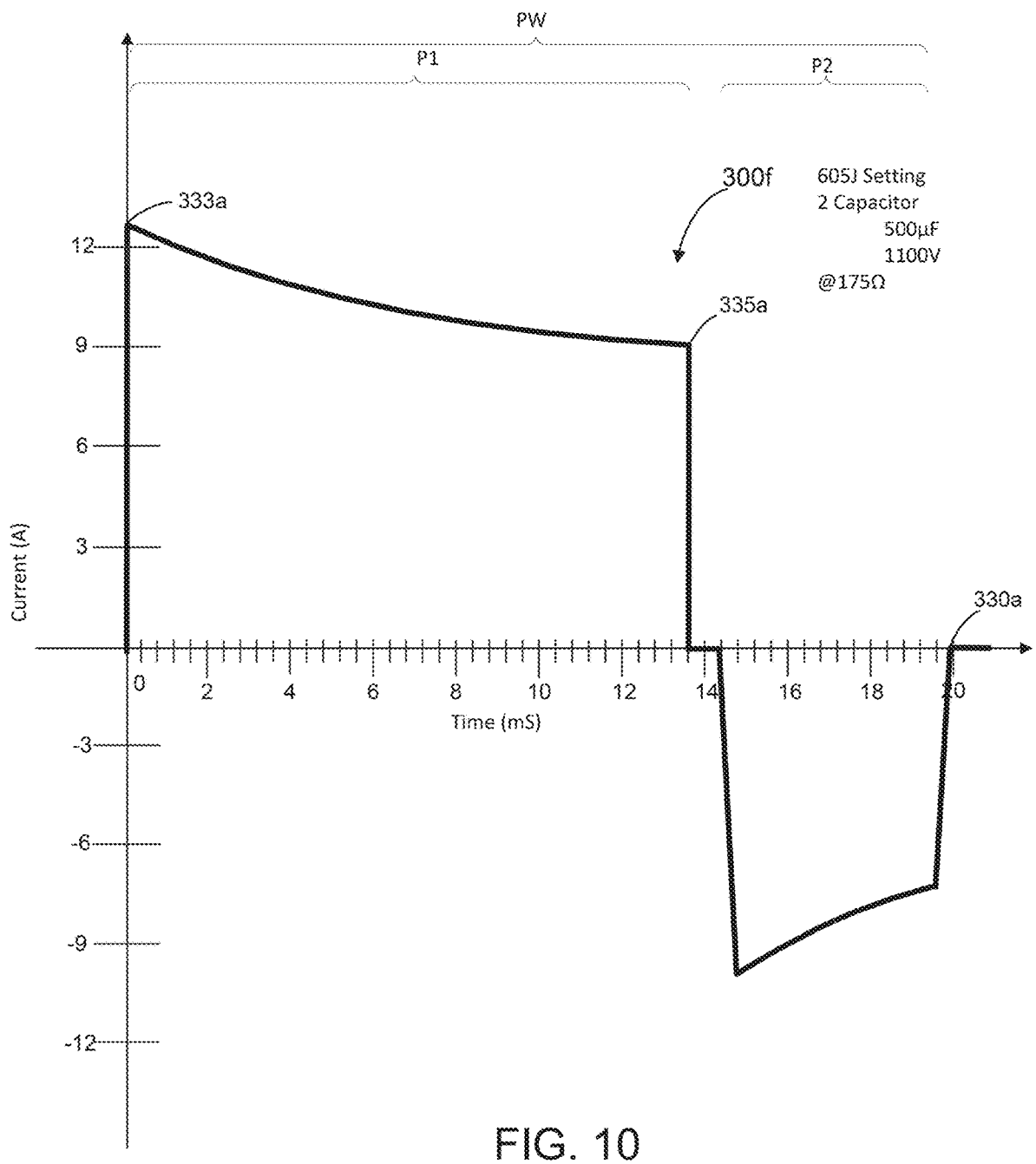
FIG. 10 is a schematic diagram of an embodiment of a waveform for a patient-worn medical device treating a patient having a transthoracic impedance of 175 ohms.

The biphasic exponential waveform 300f of FIG. 10 corresponds to values in FIG. 4B for a patient-worn arrhythmia monitoring and treatment device 100 having two capacitors (e.g. a number of capacitors 302b of two) and an delivered energy 325b of 360 J for a patient having an impedance 320a of 175 Ohms. The capacitors have a voltage 310b of 1100V. The capacitors are charged to a stored energy 310b of 605 J, and the patient-worn arrhythmia monitoring and treatment device 100 delivers a therapeutic pulse over a total pulse width Pw, or duration 330b, of 19.8 ms. The biphasic exponential waveform 300f is split across a first pulse segment P1 that starts at a peak current 333b of 12.6 A and truncates at a minimum current 335b of 10 A and a second pulse segment P2 that truncates at 19.8 ms with the delivery of 360 J. The first pulse segment P1 and second pulse segment P2 of the biphasic exponential waveform 300f have an average current 337b of 11.3 A.

Returning to the tabulated values of FIGS. 4A-4D, each capacitor 403a-403d has a capacitance C of 500 microfarad. In some implementations, the processor 218 of the controller 120 of the patient-worn arrhythmia monitoring and treatment device 100 selectively places a voltage across a subset of the capacitors 403 (e.g., fewer capacitors than the capacitor quantity 302) when charging them in parallel. If one of these capacitors 403a-403d were to fail, the controller 120 of the patient-worn arrhythmia monitoring and treatment device 100 would identify the failure during a diagnostic self-check, for example, and select a subset of the remaining functioning capacitors 403 with which to deliver a therapeutic pulse of within 15 percent of 360 J to the body of the patient. Because the implementations of FIGS. 4A-4D all include capacitors 403a-403d having an identical capacitance 305a-305d, the processor 318 is configured to calculate, for a selected subset of capacitors 403a-403d, the charge voltage 310e-310h required to achieve a stored energy 315e-315 sufficient for applying within 15 percent of 360 J of energy 325e-325h to the body of the patient regardless of patient transthoracic impedance values 320e-320h.

For example, in a configuration of a capacitor quantity 302d of four, as shown in FIG. 4D, each capacitor has a 500 microfarad capacitance 305d, and in a configuration of a capacitor quantity 302, 302c of three, as shown in FIG. 4C, each capacitor has a 500 microfarad capacitance 305c. If one of the four capacitors 403a-403d in the implementation of FIG. 4D fails, the controller 120 selects the remaining three of the capacitors and charges them to a stored energy 315, 315c in accordance with the values in FIG. 4C, which vary according to patient transthoracic impedance value 320c. The patient-worn arrhythmia monitoring and treatment device 100 therefore still provides a therapeutic treatment of within 15 percent of 360 J to the body of the patient regardless of patient transthoracic impedance TTI 320 and regardless of whether some or all of the capacitors 403a-403d are available and functioning.

In some implementations, as depicted in the tables of FIGS. 11A and 11B, the patient-worn arrhythmia monitoring and treatment device 100 includes a plurality of capacitors 403e,403f delivering within 15 percent of 360 J to 480 J of energy 325e, 325f for patients having a transthoracic impedance (TTI) value 320e, 320f of 25 ohms to 200 ohms. In the examples of FIGS. 11A and 11B, the delivered energy 325e, 325f is greater than 360 J for all impedances ranging from 25 ohms to 200 ohms. Like the examples of FIGS. 4A through 4D, the implementations of FIGS. 11A and 11B include a plurality of capacitors 4403e, 403f and each capacitor has the same capacitance value 305e, 305f in all configurations. For example, the implementation of the patient-worn arrhythmia monitoring and treatment device 100 of 11 A includes a capacitor quantity 302e of three capacitors having a capacitance value 305e of 250 microfarads. The implementation of the patient-worn arrhythmia monitoring and treatment device 100 of 11B includes a capacitor quantity 302f of four capacitors having a capacitance value 305f of 250 microfarads.

In one example, if one of these capacitors 403 were to fail, the controller 120 of the patient-worn arrhythmia monitoring and treatment device 100 would identify the failure during a diagnostic self-check, for example, and select a subset of the remaining functioning capacitors 403 with which to deliver a therapeutic pulse greater than 360 J to the body of the patient. In another example, if one of these capacitors 403 were to fail, the controller 120 of the patient-worn arrhythmia monitoring and treatment device 100 would identify the failure during a diagnostic self-check, for example, and select a subset of the remaining functioning capacitors 403 with which to deliver a therapeutic pulse of within 15 percent of 360 J to 480 J to the body of the patient. In these examples, the processor, such as processor 218 of FIG. 2, selects a subset of three capacitors with which to provide a therapeutic pulse of delivered energy 325 of at least 360 or of within 15 percent of 360 J to 480 J, as shown in the table of FIG. 11A. As shown in FIG. 11A, if the controller 120 determines that one or more of the capacitors are functioning improperly, the processor 218 identifies a subset of capacitors from the capacitor quantity 302, 302e, that are properly functioning and calculates, based on patient impedance 320, the voltage to apply across the subset of capacitors to deliver greater than 360 J of energy or within 15 percent of 360 J to 480 J.

Additionally, the implementations of FIGS. 11A and 11B incorporate the design considerations of completing the therapeutic pulse with a time interval 330e, 330f ranging from about 4 milliseconds to 22 milliseconds while keeping the minimum current 335e, 335f above 4 A across all impedance values 320e, 320f.

Figure 22:
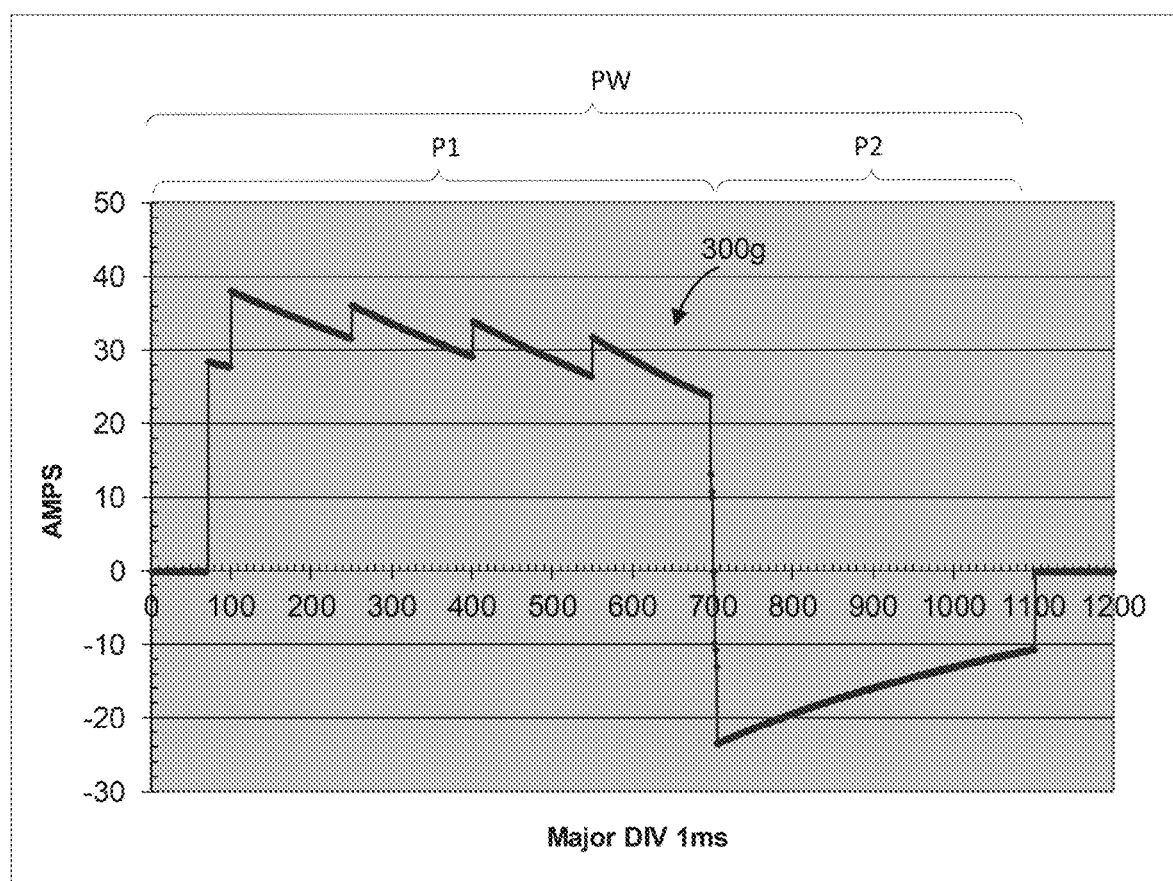
FIG. 22 is a schematic diagram of an example waveform in accordance with embodiments of the patient-worn medical device.
Figure 23:
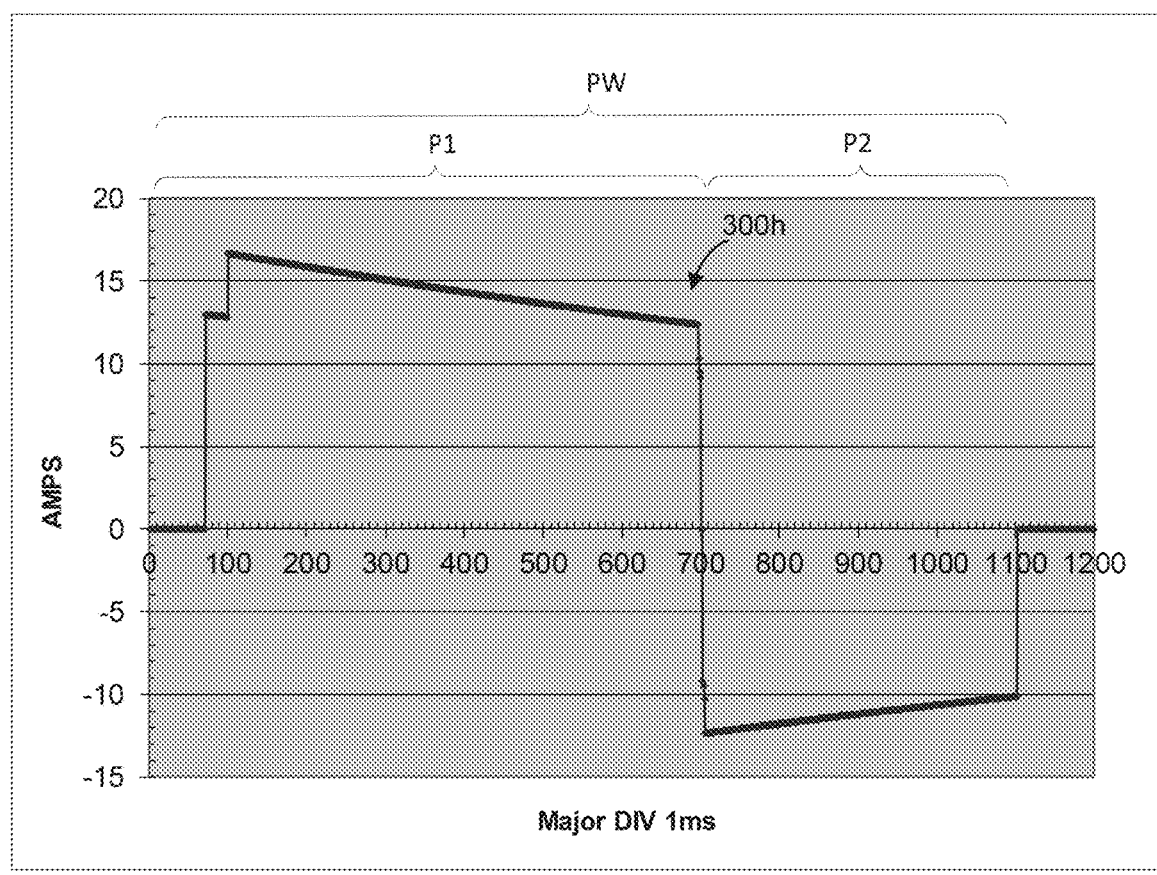
FIG. 23 is a schematic diagram of another example waveform in accordance with embodiments of the patient-worn medical device.

FIGS. 22 and 23 depict alternate embodiments of example rectilinear biphasic waveforms 300g, 300h delivering 360 J of energy across a range of transthoracic impedances. In implementations, patient-worn arrhythmia monitoring and treatment device 100 delivers within 15 percent of 360 J of energy into a patient body 102 over a biphasic pulse of a predetermined fixed duration. For example, a predetermined fixed duration of a first phase P1 is set to around 6 ms, and a predetermined fixed duration of a second phase P2 is set to around 4 ms, for a total duration of around 10 ms. The peak current decreases as the patient impedance increases and the voltage across the capacitors increases as patient impedance increases. The initial stored energy in the one or more capacitors increases with increasing patient impedance. In some implementations, TTI is known in advance and in other implementations, TTI is not known prior to delivering a pulse of energy. In the latter implementations, the device 100 includes circuitry for measuring parameters and calculating impedance directly or effectively during the delivery of the energy pulse. For example, the device 100 can monitor the rate of current delivered to the body of the patient and the voltage across the body of the patient and adjust the energy delivery settings accordingly to ensure that within 15 percent of 360 J of energy is delivered to the patient over the duration 330 of the pulse. For example, in one embodiment, for a patient having a TTI of 50 ohms, a 100 microfarad capacitor having a 3128 voltage rating is set to store 489 J of energy and delivers into a patient within 15 percent of 360 J in a rectilinear biphasic pulse lasting 10 seconds. In another embodiment, for a patient having a TTI of 200 ohms, a 100 microfarad capacitor having a 3172 voltage rating is set to store 568.5 J of energy and delivers into a patient within 15 percent of 360 J in a biphasic, rectilinear pulse lasing 10 seconds. In these embodiments of fixed duration pulses, the therapy delivery circuit 202 may include one or more feedback loops for maintaining peak current levels throughout the duration of the first pulse segment P1 and the second pulse segment P2 so that the therapy device 100 delivers within 15 percent of 360 J of energy to a patient having a transthoracic impedance in the range of about 20 to 200 ohms.

Example Patient-Worn Garments

In embodiments, the patient-worn arrhythmia monitoring and treatment device 100 further includes a garment configured to be worn about the torso of the patient wherein at least one of the pair of therapy electrodes and the at least one pair of sensing electrodes are supported by the garment, like the garments described in U.S. Publication No. 2017/0143977, titled "GARMENTS FOR WEARABLE MEDICAL DEVICES," published on May 25, 2017, which is hereby incorporated herein by reference in its entirety. In implementations, the garment may be a belt, a sash, a vest, a holster, a shirt, a wrap-around garment, a one-shoulder garment configured to be worn about one shoulder and wrap around an upper torso of the patient or some combination of fitted garments for distributing components comfortably about the torso while aligning the sensing and therapy electrodes with clinically preferred positions for successful cardiac monitoring and treatment. For example, the garment may include a vest worn about an upper torso of the patient and a separate belt that is detachable from the vest. In this example, the sensing electrodes 112, 222 and/or therapy electrodes 114, 220 may be integrated into the vest and the various modules (e.g., modules such as the energy storage 402, therapy delivery circuit 202, processor 218, and network interface 206 described above with regard to FIG. 2) may be integrated into the belt. The belt may be detachable from the vest by, for example, a buckle, a hook-and-loop fastener, and/or a snap. In addition, one or more pieces of the garment may be designed to be inexpensive and/or disposable. For example, the vest portion of the garment may be disposable while the belt (including the various modules) may be laundered and redeployed to a new patient with a new garment.

Figure 12A:
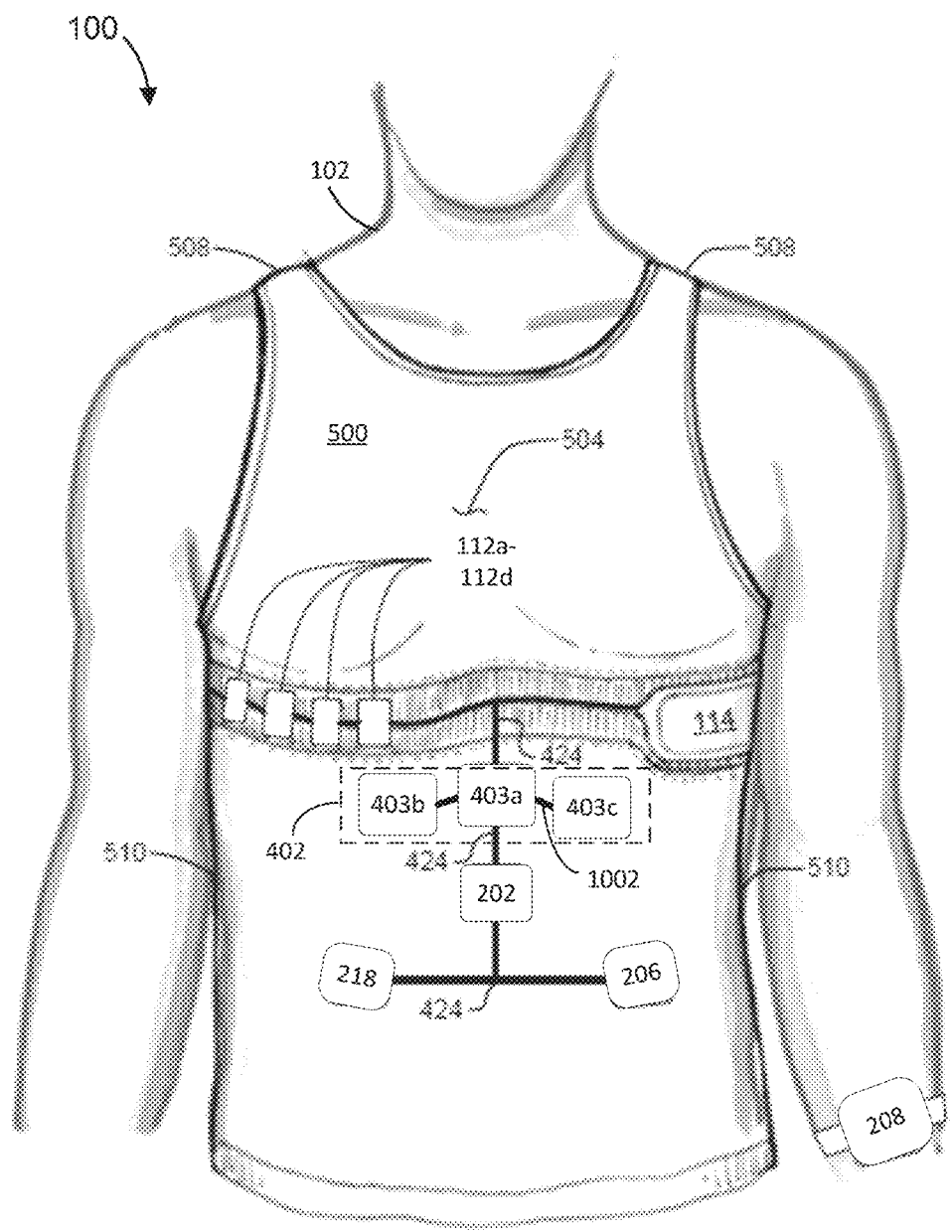
FIGS. 12A-B depict embodiments of a patient-worn medical device.
Figure 12B:
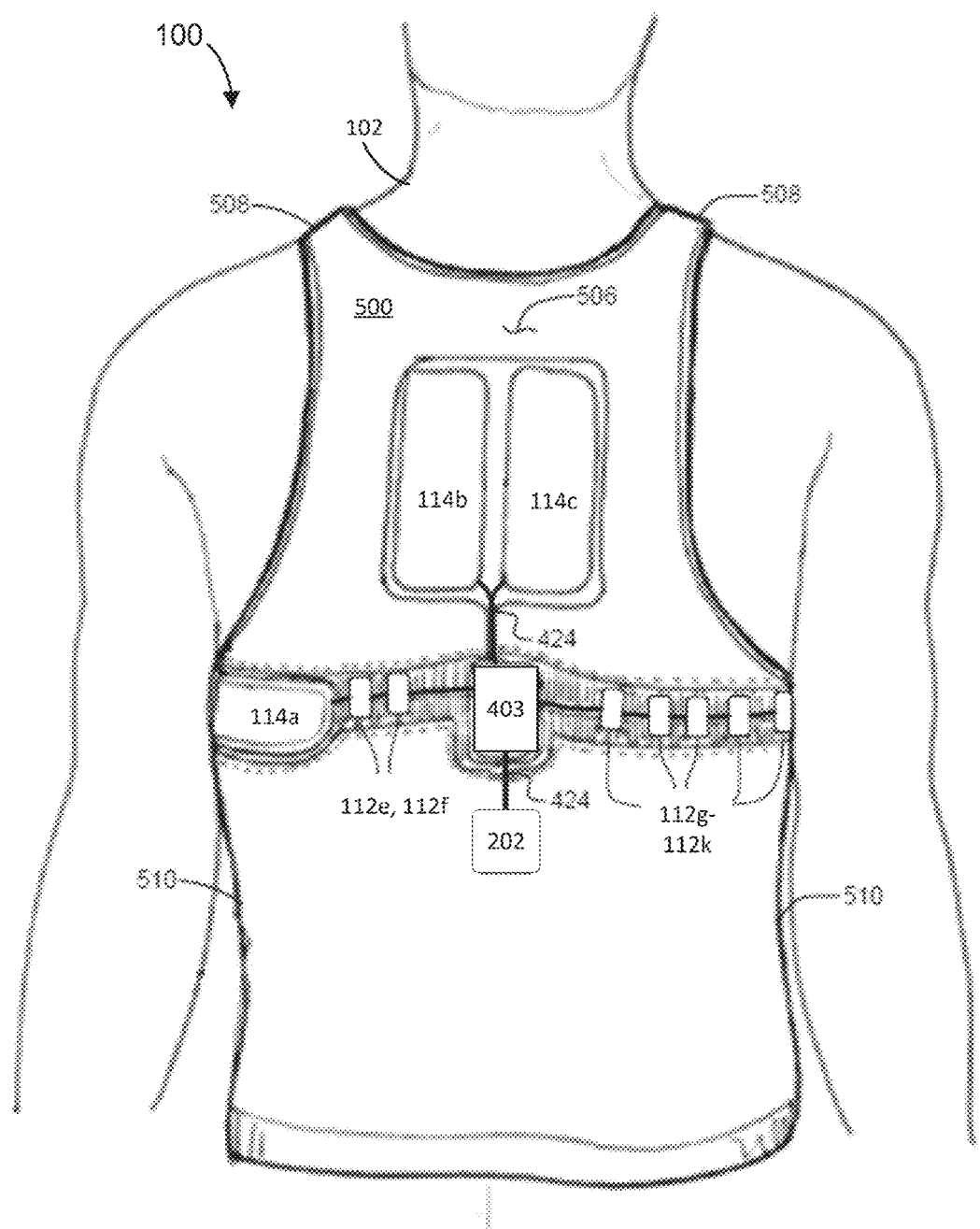

As depicted in the example garment 500 of FIGS. 12A and 12B, in implementations, the at least one pair of therapy electrodes 114, 114a, 114b and the at least one pair of sensing electrodes 112, 112a, 112b are integrated with the garment 500. In embodiments, the at least one pair of therapy electrodes 114, 114a, 114b and the at least one pair of sensing electrodes 112, 112a, 112b are manufactured as an integral component of the garment, formed of the weave and weft of the fabric. In implementations, the at least one pair of therapy electrodes 114, 114a, 114b and the at least one pair of sensing electrodes 112, 112a, 112b are supported between layers of the garment. In implementations, the at least one pair of therapy electrodes 114, 114a, 114b and the at least one pair of sensing electrodes 112, 112a, 112b are formed partially or wholly of the weave and weft of the garment, including or spanning portions of conductive fabric forming one or more panels or swaths of the garment.

In implementations, the garment 500 of the patient-worn arrhythmia monitoring and treatment device 100 includes a source of electrical energy storing and providing at least 360 J of energy to the therapy delivery circuit 202 and the source of electrical energy 402 and the therapy delivery circuit 202 are supported by the garment 500. The source of electrical energy 402 is one or more capacitors 403, 403a-403d distributed about and integrated into the garment 500, as described in detail below with regard to embodiments.

Figure 13:
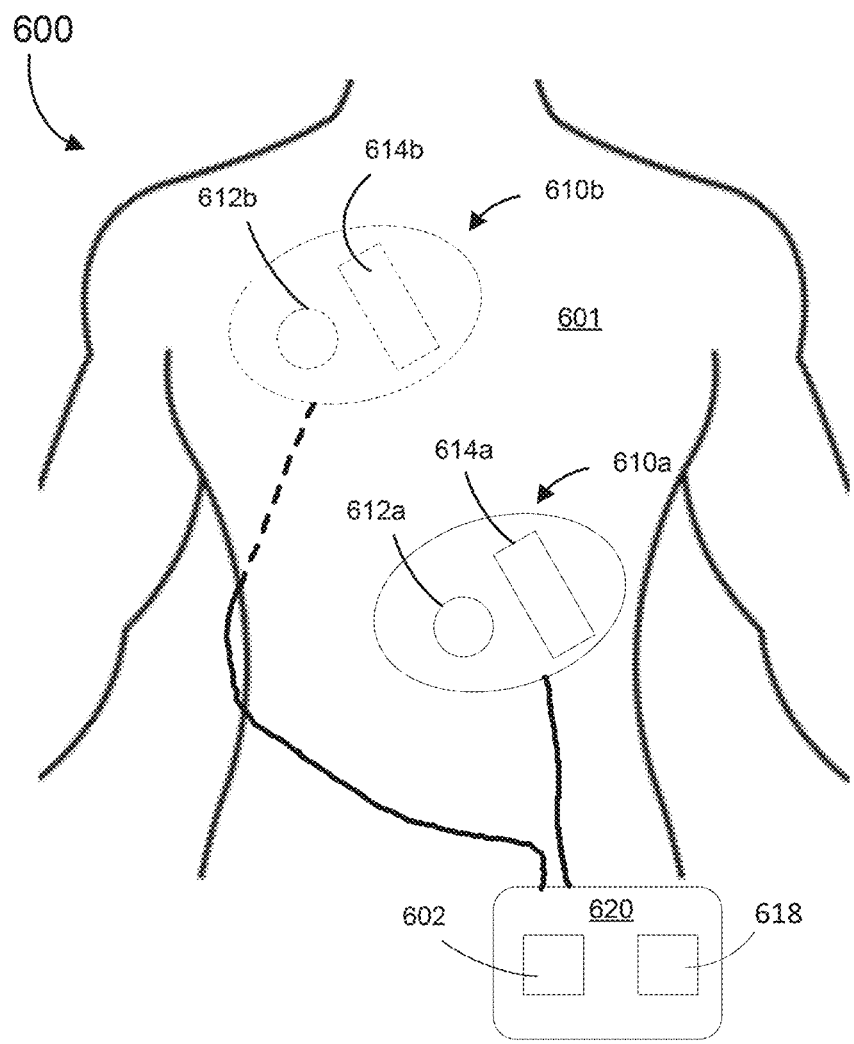
FIG. 13 depicts an embodiment of a patient-worn medical device.

Turning now to FIG. 13, in implementations, The patient-worn arrhythmia monitoring and treatment device 600 includes a patch 610, 610a, 610b. At least one of the pair of therapy electrodes 614, 614a, 614b and at least one sensing electrode 612, 612a, 612b of the at least one pair of sensing electrodes 612, 612a, 612b are disposed on a patch 610, 610a, 610b configured to be adhesively coupled to a body 601 of the patient. The patch 610, 610a, 610b is designed for short-term wear, to prevent discomfort associated with adhesives and/or the breakdown of tissue beneath the adhesive patch. Short-term wear includes periods of less than an hour, less than one day, less than a week, and less than two weeks. Short-term wear includes, for example, durations up to and including but no longer than 14 days. In implementations, the patient-worn arrhythmia monitoring and treatment device 600 includes a pair of patches 610, 610a, 610b and each patch 610, 610a, 610 has integrated therein or thereon one therapy electrode 614, 614a, 614b of the pair of therapy electrodes and one sensing electrode 612, 612a, 612b of the at least one pair of sensing electrodes. In implementations, one of the pair of patches 610, 610a, 610b is placed on the back of the body 601 of the patient above the heart and one of the pair of patches is placed on the front of the body 601 of the patient below the heart. The pair of patches 610, 610a, 610b are in wired connection with a controller 620 including a processor 618 and a therapy delivery circuit 602. In implementations, the controller 620 is configured to be worn on a belt or a holster on the body 601 of the patient. In other implementations, the controller 620 is configured to be placed near the patient, such as on a bedside table. For example, in a hospital setting, a bed-bound patient may wear the pair of patches 610, 610a, 610b, and the controller 620 attached to the patches may be adjacent the bed for continuous monitoring and treatment of any detected, treatable arrhythmias.

As described above with reference to FIGS. 12A and 12B, in implementations, the patient-worn arrhythmia monitoring and treatment device 100 includes a garment 500 configured to be worn about the torso of the patient. The patient-worn arrhythmia monitoring and treatment device 100 includes at least a pair of therapy electrodes 114, 114a, 114b, 114c, and at least one pair of sensing electrodes 112, 112a-112g configured to monitor at least one ECG signal of the patient, and a therapy delivery circuit 202 coupled to the pair of therapy electrodes 114, 114a, 114b, 114c configured to deliver one or more therapeutic pulses to the patient through the therapy electrodes 114, 114a, 114b, 114c. The patient-worn arrhythmia monitoring and treatment device 100 includes an energy storage module 402 including a plurality of capacitors 403, 403a-403d, operably connected to the therapy delivery circuit 202 and distributed about and integrated into the garment 500. The plurality of capacitors 403, 403a-403d are configured to store energy for at least one therapeutic pulse and store, for example, energy for up to five therapeutic pulses.

As described above with reference to FIG. 2, in implementations, the therapy delivery circuit 202 is included in a medical device controller 120. FIG. 2 illustrates a sample component-level view of the medical device controller 120. As shown in the embodiment of FIG. 2, the medical device controller 120 includes a therapy delivery circuit 202 including a polarity switching component such as an H-bridge 228, a data storage 204, a network interface 206, a user interface 208, at least one battery 210, a sensor interface 212, an alarm manager 214, and least one processor 218.

The processor 218 is coupled to the therapy delivery circuit 202 and configured to analyze the at least one ECG signal of the patient and detect one or more treatable arrhythmias based on the at least one ECG signal. On detecting a treatable arrhythmia, such as for example ventricular fibrillation or ventricular tachycardia, the controller 120 causes the therapy delivery circuit 202 to deliver one or more therapeutic pulses of energy to the patient. In implementations, the one or more therapeutic pulses are formed as biphasic waveforms delivering within 15 percent of 360 J of energy to the body 102 of the patient for a patient body having a transthoracic impedance in a range of about 20 ohms to 200 ohms.

In implementations, the medical device controller 120 relies on sensor information to detect transthoracic impedance of the patient body 102 and automatically selects the energy level to a value capable of delivering into the patient body 102 within 15 percent of 360 J of energy. The patient-worn arrhythmia monitoring and treatment device 100 discharges at the selected energy level to delivery within 15 percent of 360 J to 480 J of energy into the body 102 of the patient. In implementations, the selected energy level ranges from about 300 J to 575 J. In implementations, the delivered energy does not vary from 360 J of energy by more than 15 percent at any selected energy level. In implementations, the delivered energy is no less than 85 percent of 360 J. In implementations, the delivered energy level ranges from about 360 J to 414 J. In implementations, the delivered energy level ranges from about 306 J to 414 J.

Turing back now to the implementations of FIGS. 12A and 12B, the at least one of the pair of therapy electrodes 114, 114a-114c and the at least one pair of sensing electrodes 112, 112a-112d are supported by the garment 500, and the garment 500 is configured to be worn continuously by the patient for an extended period of time. In other configurations (not shown) either the at least one of the pair of therapy electrodes 114, 114a-114c or the at least one pair of sensing electrodes 112, 112a-112d are supported by the garment 500, and the garment is configured to be worn continuously by the patient for an extended period of time. As described previously, in implementations, continuously is constantly or substantially constantly. In implementations, wearing the garment continuously means the patient wears the garment at all times except during short periods of maintenance, such as removing the garment for laundering or during short periods of activity such as showering. In some implementations, the garment is waterproof and continuous wear includes constant, uninterrupted durations of wear. In implementations, an extended period of time for continuous wear is, for example, a prescribed duration of one day, one week, two weeks, more than two weeks, a month, two months, six months, or a year.

In implementations, the garment 500 may be a belt, a sash, a vest, a holster, a shirt, a wrap-around garment, a one-shoulder garment configured to be worn about one shoulder and wrap around an upper torso of the patient or some combination of fitted garments for distributing components comfortably about the torso while aligning the sensing and therapy electrodes with clinically preferred positions for successful cardiac monitoring and treatment.

Any of the garments described herein may include multiple parts. For example, the garment may include a vest worn about an upper torso of the patient and a separate belt that is detachable from the vest. In this example, the sensing electrodes 112, 222 and/or therapy electrodes 114, 220 may be integrated into the vest and the various modules (e.g. energy storage module 402, therapy delivery circuit 202, processor 218, and network interface 206 described above) may be integrated into the belt. The belt may be detachable from the vest by, for example, a buckle, a hook-and-loop fastener, and/or a snap. In addition, one or more pieces of the garment may be designed to be inexpensive and/or disposable. For example, the vest portion of the garment may be disposable while the belt (including the various modules) may be laundered and redeployed to a new patient with a new garment.

The implementations of FIGS. 12A and 12B depict the set of modules described with regard to the embodiment of FIG. 2 distributed about the garment 500. The garment 500 includes a front portion 504 and a rear portion 506 that cover both an upper portion of the torso and a lower portion of the torso of the patient. As shown in FIG. 12A, the garment 500 includes shoulder portions 508 and side portions 510 that connect the front portion 504 to the rear portion 506 of the garment 110. The side portions 510 may extend from under the arms to near the waist line (e.g., to the bottom of the torso) in a similar fashion to a vest or a T-shirt. The shoulder portions 508 may be narrow strips of fabric constructed in a similar fashion to shoulder portions of vests. For example, the garment 500 may be comprised of stretchable, anti-microbial, breathable, and/or moisture-wicking fabric.

In some implementations, the ECG sensing electrodes 112a-112k (collectively referred to as sensing electrodes 112) can be disposed at various predetermined locations including different axial positions around the body of the patient as shown and described in, for example, FIGS. 1A-F of U.S. Pat. No. 8,706,215, titled "WEARABLE AMBULATORY MEDICAL DEVICE WITH MULTIPLE SENSING ELECTRODES," issued on Apr. 22, 2014 (hereinafter the "'215 patent"), which is hereby incorporated herein by reference in its entirety. In some examples, the sensor interface module 212 may include a multiplexer to control which ECG sensing electrode pairings are being monitored. For example, the sensor interface module 212 may identify one or more optimal pairings (e.g., the pairings with the best signal quality) and control a state of the multiplexer so as to receive ECG signals from the identified pairing(s) of sensing electrodes 112. It is appreciated that the sensing electrodes 112 may be multiplexed manually. For example, the garment may include multiple predetermined locations to receive ECG sensing electrodes 112 and a pairing may be selected by only connecting ECG sensing electrodes 112 at a subset of the predetermined locations.

The modules (e.g. energy storage module 402, therapy delivery circuit 202, processor 218, and network interface 206) of the controller 120 are distributed about the garment 500 so as to evenly distribute the weight of the medical device on the left shoulder and the right shoulder of the patient. As illustrated in FIG. 12A, the user interface module 208 is implemented as a computer-enabled watch. It is appreciated that other implementations of the user interface module 208 may be employed. For example, the user interface may be permanently disposed with or removably attached to the garment 500 and accessible by the patient.

The link between the network interface 206 and the user interface module 208 may be a wireless link while the link between the network interface 206 and the processor 218 may be a wired link (e.g., wired by a cable). Further, the wired links (if any) between the modules (e.g. energy storage module 402, therapy delivery circuit 202, processor 218, and network interface 206) may include wires having different wire gauges. For example, the link 424 coupling the energy storage module 402 to the therapy electrode 114 may support 2,500 volts and a 20,000 volt ESD while the link 424 between the operations module 406 and the communications module 408 may have a lower voltage and ESD rating.

In some examples, one or more of the links 424 may be integrated into the garment 500. In some examples, one or more of the links 124 may be disposed between two layers of fabric of the garment. For example, the links 424 may be constructed from conductive thread, wires, cables, and/or fiber optical cables integrated into the garment 500. In these examples, the garment 500 is configured to receive each of the modules and operably couple the modules to the links 424 integrated into the garment when the modules are attached to the garment 500. In these examples, a user (e.g., a patient, physician, or caregiver) can configure the wearable medical device 100 for monitoring or treatment based on the modules that are removably coupled to the garment 500. For example, the wearable medical device 100 may be configured as a wearable monitoring device by not installing the treatment modules. In this example, the treatment functionality of the wearable medical device may be restored by attaching the appropriate treatment modules to the garment.

As depicted in the example garment 500 of FIGS. 12A and 12B, in implementations, the at least one pair of therapy electrodes 114, 114a, 114b (collectively referred to as therapy electrodes 114) and the at least one pair of sensing electrodes 112 are integrated into the garment. In embodiments, the at least one pair of therapy electrodes 114 and the at least one pair of sensing electrodes 112 are manufactured as an integral component of the garment 500, formed of the weave and weft of the fabric. In implementations, the at least one pair of therapy electrodes 114 and the at least one pair of sensing electrodes 112 are supported between layers of the garment 500. In implementations, the at least one pair of therapy electrodes 114 and the at least one pair of sensing electrodes 112 are formed partially or wholly of the weave and weft of the garment 500, including or spanning portions of conductive fabric forming one or more panels or swaths of the garment 500.

Figure 14A:
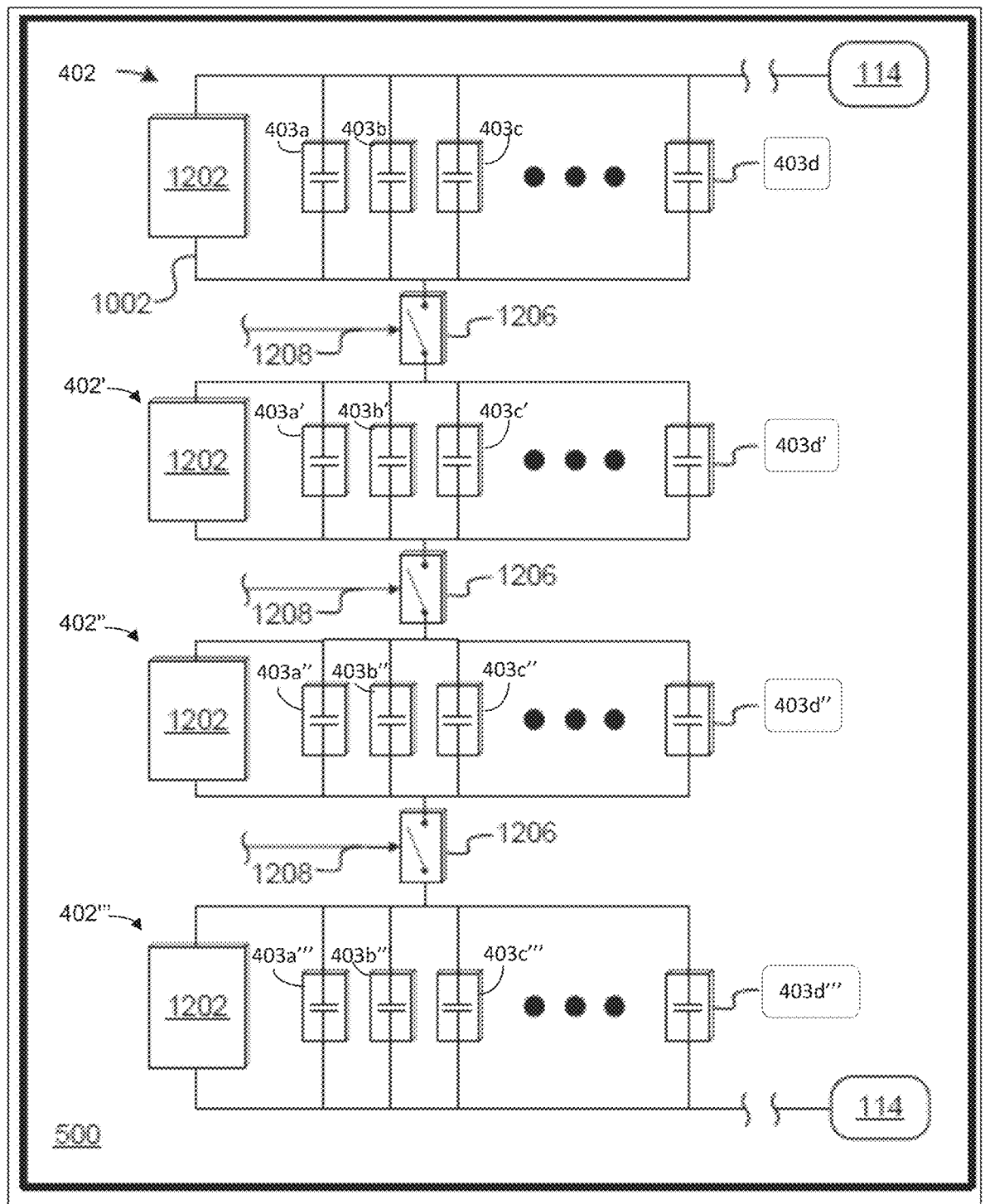
FIGS. 14A-B depict embodiments of schematics of energy storage modules of a patient-worn medical device.

In some examples, the plurality of capacitors 403 are integrated into the garment 500. For example, as illustrated in FIGS. 12A and 14A the charge capacity of energy storage module 402 may be divided over a network of small capacitors 403a-d (collectively referred to as capacitors 403) that are each integrated into separate regions of the garment 500 at various locations and coupled by conductive threading 1002 or wiring. In some implementations, the garment 500 removably couples to a rechargeable battery for powering the plurality of capacitors 403. In implementations, such as that of FIG. 12A, the plurality of capacitors 403 may be integrated into various locations so as to evenly distribute the weight of the energy storage module 402. In other implementations, such as that of FIG. 12B, the plurality of capacitors 403 may be nested in a stacked configuration. For example, the plurality of capacitors 403 may be flat, film-type capacitors nested within a frame (not shown) integrated into the garment 500.

In examples, the energy storage module 402 can be a capacitor bank including a plurality of capacitors 403 (e.g., capacitors 403a-d of FIG. 3). Energy storage is distributed over a plurality of relatively smaller capacitors 403 rather than one relatively larger capacitor having an energy storage capacity equal to that of the plurality of relatively smaller capacitors 403. The garment 500 advantageously carries an evenly distributed weight of the plurality of capacitors 403 rather than a localized weight of one relatively larger capacitor. This improves comfort during a long-term prescribed duration of wear. For example, the plurality of capacitors 403 may be flat-packed film capacitors each with a maximum thickness of between 1 mm and 40 mm, a capacitance under 250 microfarads, and a breakdown voltage rating between 1300 and 2500 volts. Thereby, the capacitors 403 may be integrated into or attached to the garment 500 with a low profile and even weight distribution. This configuration prevents interfering with the mobility of the patient. It is appreciated that one or more batteries 210 may be similarly divided into a plurality of cells and integrated in an evenly spread weight distribution into the garment 500.

Referring to FIG. 14A, a plurality of capacitors 403a-403d (collectively referred to as capacitors 403) may be organized into a plurality of capacitor banks (e.g., 4 capacitor banks 402, 402', 402'', 402''', collectively referred to as capacitor banks 402) each coupled to a charger 1202. For example, one or more of the capacitors 403 of a capacitor banks 402 may be removably coupled to a charger 1202. The capacitor banks 402 may be coupled to each other by one or more switches 1206 that control the connection between the capacitor banks 402 based on a control signal 1208 from, for example, the therapy delivery circuit 202. Thereby, each of the capacitor banks 402 may be charged in parallel by a charger 1202 by opening the switch(es) 1206 and discharged in series with one another by closing the switch(es) 1206. It is appreciated that the number of capacitor banks 402 employed and/or the particular number of capacitors 403 in each bank 402 can be altered based on particular implementations. Further, a single charger 1202 may be employed to charge multiple capacitor banks. For example, the four chargers 1202 illustrated in FIG. 14A may be replaced by a single charger connected to all four of the capacitor banks 402.

Figure 14B:
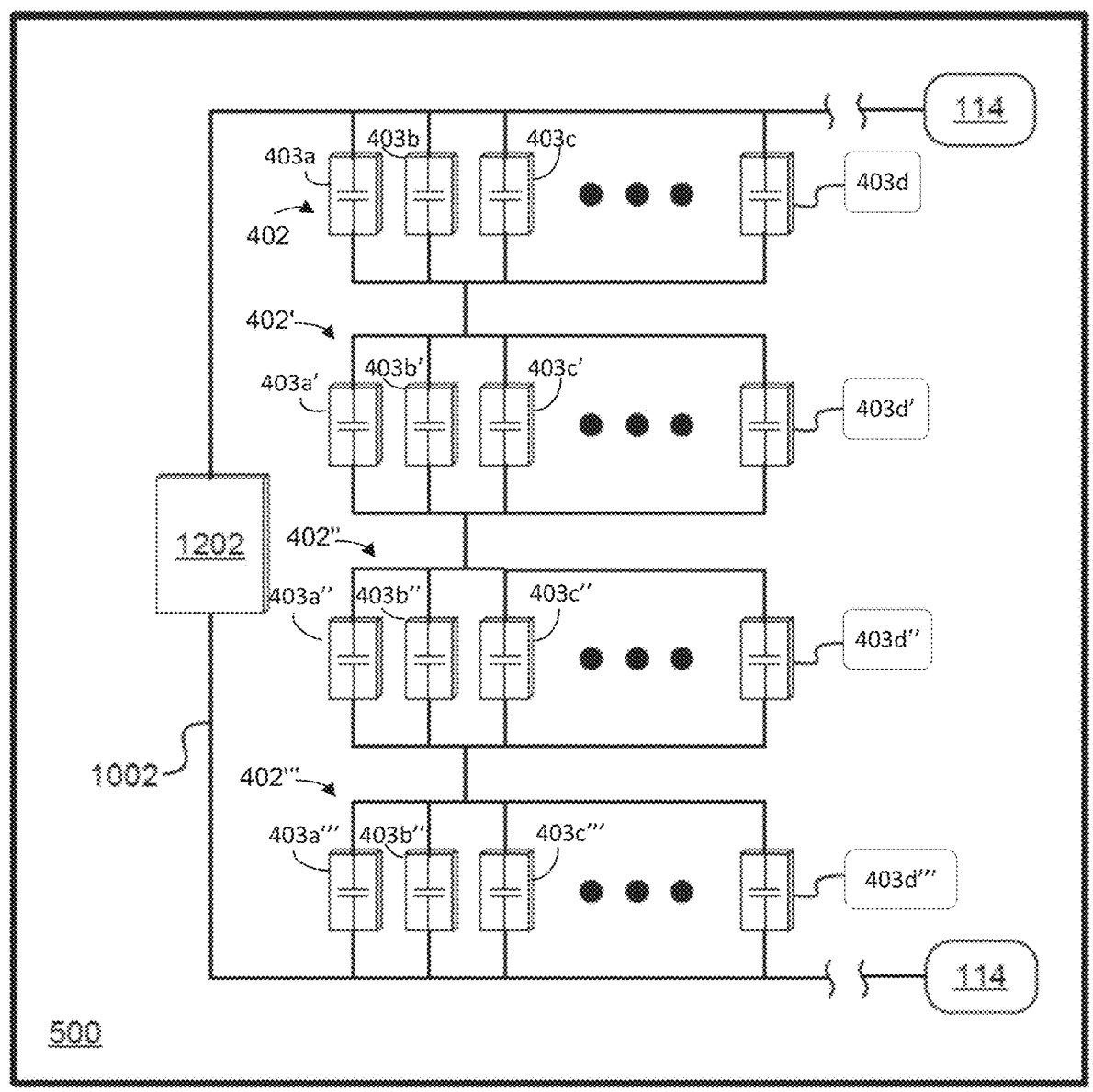

In some implementations, each capacitor bank 402 may have a total capacitance rating (e.g., 204 microfarads) that is divided up among the plurality of capacitors 403 connected in parallel. The total capacitance of the capacitor bank 402 is equal to the sum of the capacitance of each of the plurality of capacitors 403 in the bank. Thereby, a target total capacitance rating may be achieved by matching the sum total of the capacitances of the plurality of capacitors 403 in the bank to the target. For example, the capacitor bank 402 may be designed to have a capacitance of 650 μF and the capacitor bank may be constructed from 100 capacitors each with a capacitance of 6.5 μF (6.5 μF*100=650 It is appreciated that other capacitor configurations may be employed including, for example, 130 capacitors each with a capacitance of 5 μF (5 μF*130=650 μF). Although FIGS. 14A and 14B illustrate four capacitor banks 402 each including a plurality of capacitors 403 where each capacitor bank 402 may have a total capacitance of about 204 microfarads, it is to be appreciated that other examples may include capacitor banks having different capacitances or capacitor banks having only a single capacitor each. For example, in one implementation a wearable arrhythmia monitoring and treatment device 100 may include four capacitors 403 each with a capacitance of about 500 microfarads.

Referring to FIG. 14B, the capacitors may be organized in a plurality of banks 402 that are coupled in series without the switch 1206. In these implementations, the capacitor banks may be charged in series by a charger 1202. Both charging and discharging the capacitor banks in a series configuration may omit one or more components (e.g., the switch(es) 1206), but may require a higher charging voltage to store the same amount of energy relative to the parallel charging configuration illustrated in FIG. 14A.

Figure 15A:
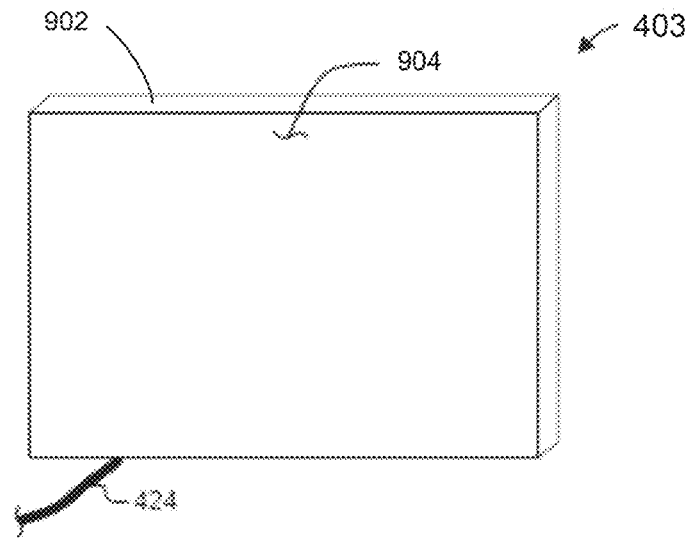
FIGS. 15A-B depict embodiments of an energy storage module of a patient-worn medical device.
Figure 15B:
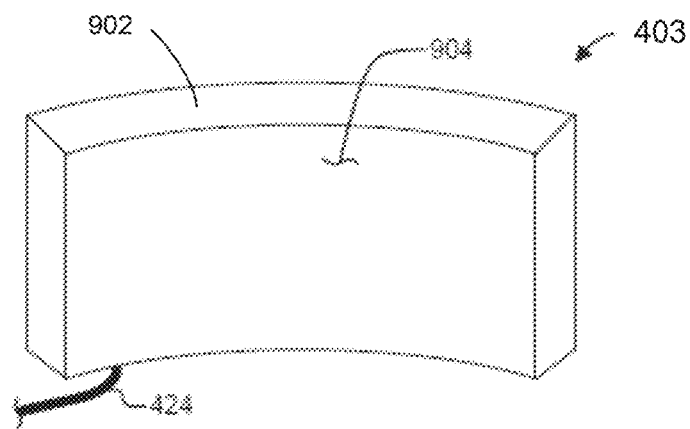

It is appreciated that the each capacitor of the plurality of capacitors 403 may be constructed in a variety of form factors. For example, as shown in FIG. 15A, each capacitor of the plurality of capacitors 403 may be constructed as a capacitor module comprising a capacitor (e.g., a ceramic capacitor) encapsulated in a rigid enclosure 902 that is integrated into the garment. In implementations, the rigid enclosure is contoured to conform to the curvature of the torso of the patient thereby resulting in a comfortable, mated fit when worn. For example, as shown in FIG. 15B, the enclosure 902 may be constructed from a rigid plastic including, for example, acrylonitrile butadiene styrene (ABS) plastic with a contoured surface 904 that may conforms to the silhouette of a patient. For example, the contoured surface 904 can be configured to conform with a curvature of a portion of the patient's torso, such as lower portion of the torso, an upper anterior portion of the torso, upper posterior portion of the torso, one or more lateral portions of the torso. The particular shape of the contoured surface 904 may be pre-configured or uniquely designed for the patient. For example, various body size measurements may be obtained from the patient and a uniquely tailored enclosure 902 may be 3D printed from, for example, any suitable thermoplastic (e.g., ABS plastic).

The capacitors 403 may also be custom-made capacitors created by packing a dielectric between two conductive plates and attaching conductive thread or wiring to the conducting plates. In some implementations, each capacitor of the plurality of capacitors 403 may be small capacitors that are directly integrated into the garment and coupled by conductive thread or wiring. In some examples, the plurality of capacitors 403 may be integrated into other components of the wearable medical device 100. For example, the wearable medical device may include one or more flat or contoured surfaces including, for example, a back-side of a gel deployment pack and/or a back-side of a therapy electrode 114. In these examples, a capacitor 403 may be integrated into these flat or contoured surfaces by placing a dielectric between two conductors.

In implementations, each capacitor of the plurality of capacitors 403 may be a small film capacitor with a maximum thickness of between 1 mm and 40 mm, a capacitance under 700 microfarads, and a breakdown voltage rating between 500 and 2500 volts. Thereby, the plurality of capacitors 403 may be easily integrated into the garment 500 without interfering with the mobility of the patient. In some examples, at least one capacitor of the plurality of capacitors 403 is a film capacitor manufactured of tightly wound dielectric layers that are compressed and molded to match the silhouette of a patient. By shaping one or more of the plurality of capacitors 403 to accommodate on or more contoured regions of a patient's body 102, the capacitors may be integrated into separate regions of the garment to distribute weight evenly and to areas of least discomfort and to minimize bulkiness associated with round or stacked capacitors.

In implementations, the contoured plurality of capacitors 403 are permanently affixed to the garment 500 and sandwiched between two pieces of fabric. In some examples, the contoured plurality of capacitors 403 are waterproof and/or water-resistant and covered in a waterproof coating (e.g., an epoxy coating). Thereby, the garment 500 may be washed or worn in shower without damaging the electrical components that are permanently disposed into the garment 500.

The plurality of capacitors 403 of the patient-worn monitoring and treatment device 100 provide energy for one or more therapeutic pulses of delivered high energy of within 15 percent of 360 J of energy. In some implementations, the one or more therapeutic pulses are biphasic exponential defibrillation pulses each having a first pulse segment and a second pulse segment. As described above with regard to FIGS. 4 through 10 and FIGS. 22 and 23, the therapy delivery circuit 202 can include, or be operably connected to, circuitry components that are configured to generate and provide the therapeutic shock. The circuitry components can include, for example, resistors, one or more capacitors, relays and/or switches, an electrical bridge such as an H-bridge 228 (e.g., including a plurality of insulated gate bipolar transistors or IGBTs that deliver and truncate a therapy pulse), voltage and/or current measuring components, and other similar circuitry components arranged and connected such that the circuitry components work in concert with the therapy delivery circuit and under control of one or more processors (e.g., processor 218) to provide, for example, one or more pacing or defibrillation therapeutic pulses.

As shown in the embodiment to FIG. 3, the H-bridge 228 includes an energy storage module 402 including four capacitors 403a, 403b, 403c, 403d charged in parallel at a preparation phase 227a and discharged in series at a treatment phase 227b. During the treatment phase 227b, the H-bridge 228 applies a therapeutic pulse that causes current to flow through the body 102 of the patient in desired directions for desired durations. The H-bridge 228 includes H-bridge switches 229a, 229b, 229c, 229d opened and closed selectively by a switching transistor such as insulated gate bipolar transistors (IGBTs), silicon carbide field effect transistors (SiC FETs), metal-oxide semiconductor field effect transistors (MOSFETS), silicon-controlled rectifiers (SCRs), or other high current switching devices. Switching a pair of transistors to a closed position, for example switches 229a and 229c, enables current to flow in a first direction for first pulse segment P1. Opening switches 229a and 229c and closing witches 229b and 229d enables current to flow through the body of the patient in a second pulse segment P2 directionally opposite the flow of the first pulse segment P1.

As depicted in the implementations of FIGS. 4 through 9, and FIGS. 13 and 14, the therapeutic pulses formed as biphasic pulses 300, 300a-300h include a first pulse segment P1 and a second pulse segment P2. The controller applies a selected amount of electrical energy to the patient body 102 during the first pulse segment P1 and the remaining amount of the selected amount of electrical energy is applied to the patient during the second pulse segment P2. In implementations, the H-bridge 228 produces the first pulse segment P1 and the second pulse segment P2 by initiating the delivery of energy into the patient body 102 at the start of the first pulse segment P1, reversing polarity of current flow at the start of the second pulse segment P2, and truncating the energy delivery at the completion of the second pulse segment P2 when the energy delivered to the body 102 of the patient is substantially equal to 360 J. For example, the energy pulse is truncated when the energy delivered into the body 102 of the patient is within 15 percent of 360 J for all transthoracic impedance values.

Example Treatment Methods

In implementations, the patient-worn arrhythmia monitoring and treatment device 100 further includes a patient notification output. In response to detecting one or more treatable arrhythmias, the controller is configured to prompt the patient for a response by issuing the patient notification output, which may be an audible output, tactile output, visual output, or some combination of any and all of these types of notification outputs. In the absence of a response to the notification output from the patient, the controller is configured to cause the therapy delivery circuit to deliver the one or more therapeutic pulses to the patient.

Figure 16:
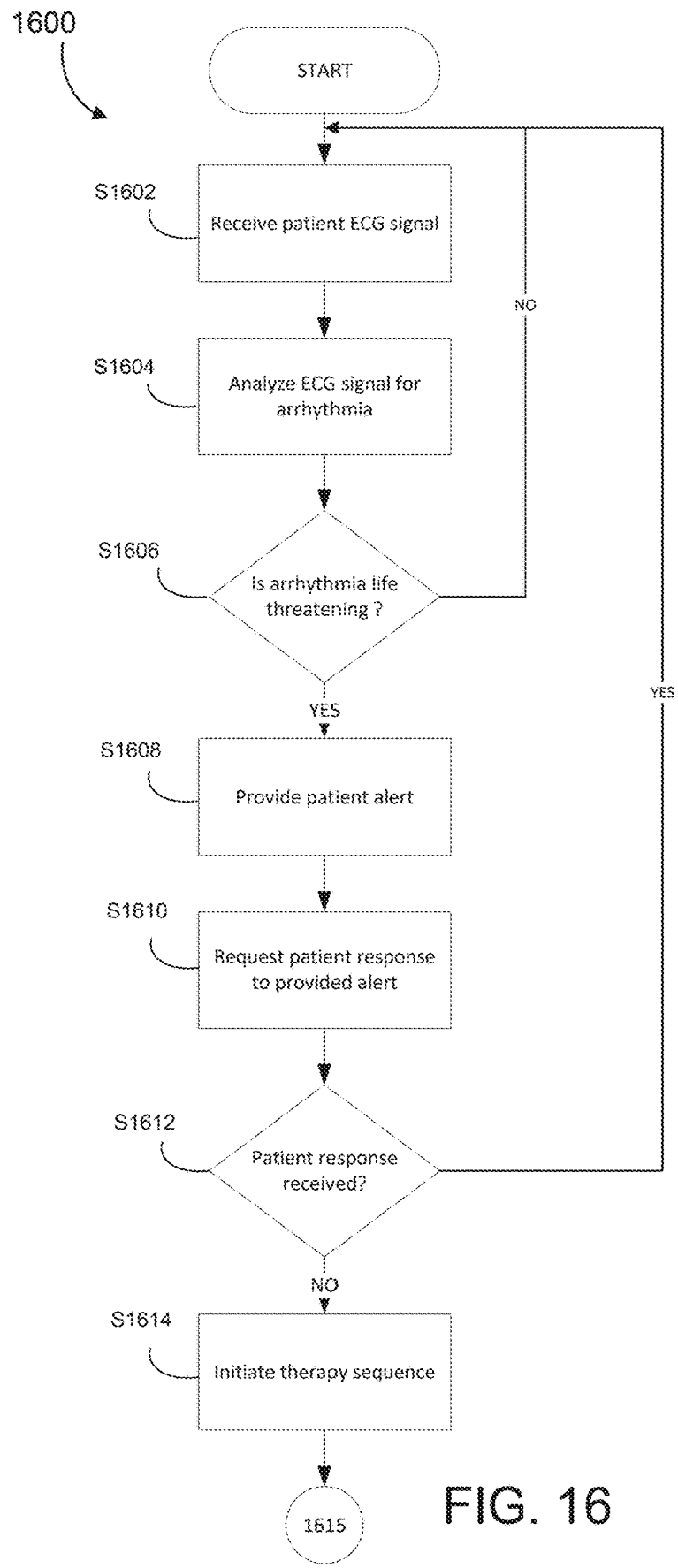
FIG. 16 is a flow diagram illustrating an embodiment of a medical device control process.

FIG. 16 depicts an example of a process 1600 for determining whether to initiate a therapy sequence and apply a therapeutic pulse to the body of a patient. In implementations, the controller, such as one of the controllers 120, 620 of the embodiments of FIGS. 1 and 13, receives S1602 a patient ECG signal from the pair or therapy electrodes and analyzes S1604 the ECG signal for arrhythmia. The controller determines S1606 whether the arrhythmia is life threatening and requires treatment. If the arrhythmia is not life threatening, the controller can cause a portion of the ECG signal to be stored in memory for later analysis and continue to monitor the patient ECG signal. If the arrhythmia is life threatening, the controller provides S1608 a patient notification output and requests S1610 a patient response to the provided notification output. The response may be, for example, pressing one or more buttons in a particular sequence or for a particular duration. The controller determines S1612 whether the patient response was received. If the patient responds to the notification output, the controller is notified that the patient is conscious and returns to a monitoring mode. If the patient is unconscious and unable to respond to the provided alert, the controller initiates S1614 the therapy sequence 1700.

Figure 17:
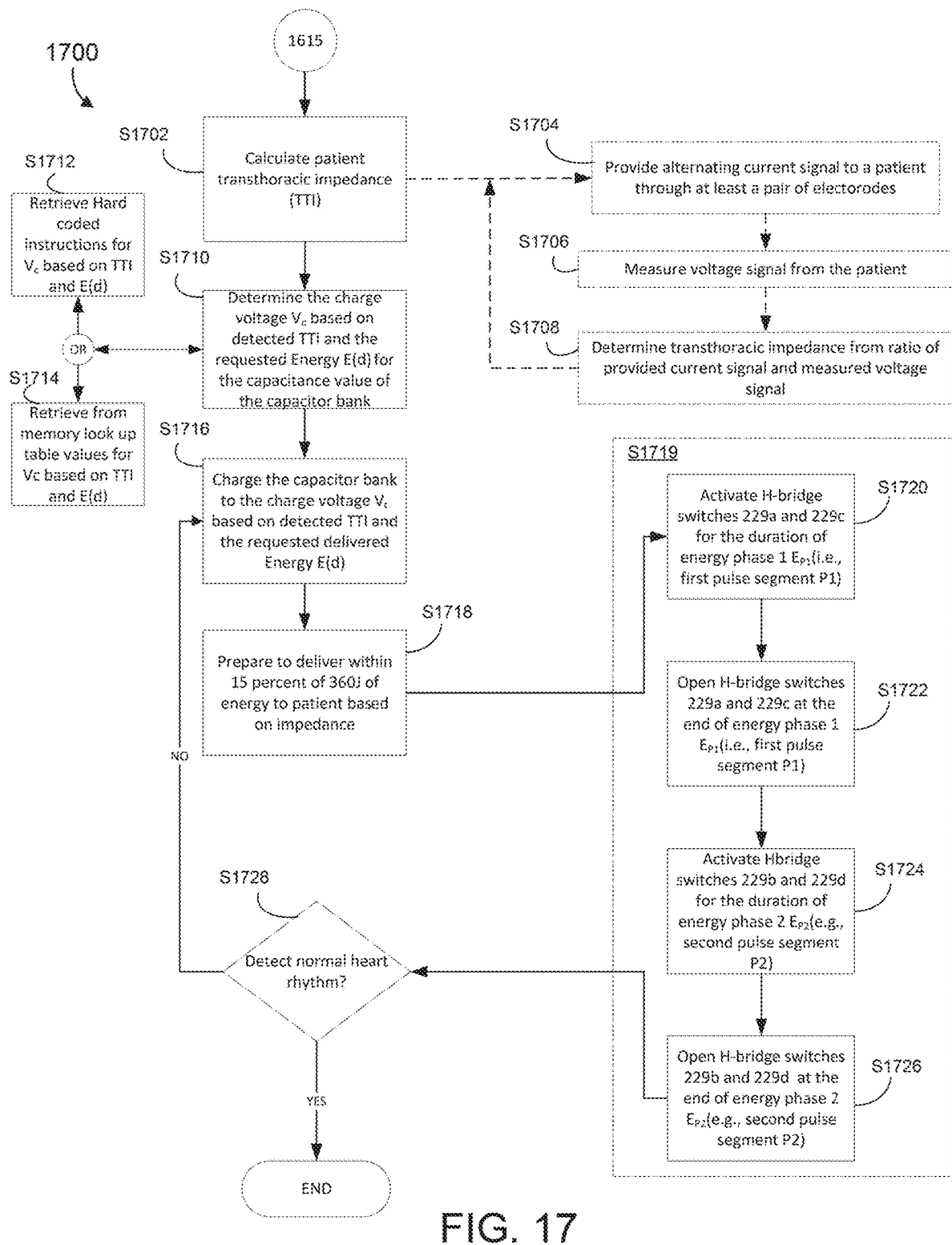
FIG. 17 is a flow diagram illustrating an embodiment of a medical device control process.

In one embodiment exemplified in FIG. 17, at the start of the therapy sequence 1700, the controller calculates S1702 patient impedance (also referred to herein as "TTI"). One or more techniques for detecting TTI may be employed. In one embodiment, shown in dashed line in FIG. 7, the controller provides S1704 an alternating current signal to the patient through at least a pair of electrodes and measures S1706 the voltage signal from the patient. The controller then determines S1708 TTI from the ratio of provided current signal and measured voltage signal. In other embodiments, the controller may calculate patient impedance using, for example, bridge circuits, (e.g., a Wien Bridge, Wheatstone bridge, Maxwell bridge, etc.) that can determine impedance values by comparing measured values to known impedance values. By connecting an unknown impedance to one arm of a bridge, the other arms of the bridge can be adjusted (e.g., nulling the bridge) to reveal the unknown impedance. Using a Wien bridge, capacitance values may be measured in terms of resistance and frequency. Bridge variations may also be implemented dependent upon the frequency range of the signals used in the TTI measurements, for example, transformer ratio arm bridges, Berberian-Cole Bridges, and auto-balance bridges may be used to determine unknown impedance for particular ranges.

Once the controller calculates S1702 the patient TTI, the controller determines S1710 the charge voltage 310 (Vc) based on the calculated TTI. In one embodiment, the controller retrieves S1714 from memory look up table values for the charge voltage Vc based on the TTI and the delivered energy E(d) to be delivered to the patient. These look up table values are, for example, values such as those in the tables of FIGS. 4A through 4D for a delivered energy 325 of within 15 percent of 360 J and those in the tables of FIGS. 11A and 11B for delivering at least 360 J or for delivering within 15 percent of 300 J to 480 J. In embodiments, the patient transthoracic impedance values function as a look up key for the controller. In the tables of FIGS. 4A through 4D, for example, the look up key is the impedance value 320a-320d and the therapy sequence relies on the controller calculating S1702 TTI 320 for determining S1710 the charge voltage Vc 310 associated with the patient impedance 320a-320d in a look up table corresponding to a number of capacitors 302a-302d in the device 100. In embodiments, the number of capacitors 302 is predetermined and pre-programmed in to the controller. In other embodiments, described later with regard to FIG. 18, the number of capacitors 302 may vary and the controller determines the number of capacitors 302 available for charging.

In another embodiment, the controller retrieves S1712 hard coded instructions for determining the charge voltage Vc based on the calculated TTI 320 and the delivered energy E(d). For example, hard coded instructions may include one or more IF, THEN, ELSE IF instructions for a patient. The following inset text is example pseudocode for such hard-coded instructions:

---

...
C = 500 uF; // code snippet assumes that device is equipped with 500 uF capacitor
N = 4; // code snippet assumes four capacitors
Tmax = 22 ms // Maximum predetermined time period of pulse duration
Irheo = 4 // amps; minimum peak current (rheobase current)
Ed = 360 // Joules – Energy set to be delivered to the patient
INPUT R // Patient impedance (TTI)
IF R = 50;
    THEN Vc = 650
    Deliver (Ed); // Deliver within 15% of Ed
ELSE IF R = 75;
    THEN Vc = 650
    Deliver (Ed); // Deliver within 15% of Ed
ELSE IF R = 125;
    THEN Vc = 700
    Deliver (Ed); // Deliver within 15% of Ed
ELSE IF R = 150;
    THEN Vc = 700
    Deliver (Ed); // Deliver within 15% of Ed
ELSE IF R = 175;
    THEN Vc = 800
    Deliver (Ed); // Deliver within 15% of Ed
ELSE IF R = 200;
    THEN Vc = 800
    Deliver (Ed); // Deliver within 15% of Ed $$Es = \frac{1}{2} * CVc^2 * N$$

$$T = \frac{-\ln\left(1 - \frac{Ed}{Es}\right)RC}{2}$$

Ipeak = N *(Vc/R)

$$Imin = Ipeak * e^{-\left(\frac{T}{RC}\right)}$$

Iavg = (Ipeak +Imin)/2
...

---

Once the controller determines S1710 the charge voltage Vc, the controller charges S1716 the energy storage module 402, such as one or more of a plurality of capacitors 403a-403d, to the determined charge voltage Vc based on the requested delivered energy E(d). The requested, or targeted, delivered energy E(d) may be the desired quantity of energy delivered to the body of the patient, such as an energy of within 15 percent of 360 J. The controller then prepares S1718 to deliver energy to the patient based on the calculated TTI. In one embodiment, the controller prepares S1718 to deliver 360 J of energy to the patient. The controller delivers S1719 a therapeutic pulse to the body of the patient by controlling the energy delivery in accordance with a biphasic truncated exponential pulse using, for example, an H-Bridge. In the embodiment of the therapy sequence 1700 of FIG. 17, the controller activates S1720 two of four H-bridge switches, such as switches 229a and 229c of FIG. 3, for the duration of a first energy phase (e.g., first pulse segment P1) and then opens S1722 the activated H-bridge switches at the end of the first energy phase. The controller activates S1724 two other of the four H-bridge switches, such as switches 229b and 229d for the duration of the second energy phase (e.g., second pulse segment P2) and then opens S1726 the two other H-Bridge switches at the end of the second energy phase.

In implementations, the therapy delivery circuit delivers within 15 percent of 360 J. In implementations, the delivered energy is no less than 85 percent of 360 J. In implementations, the delivered energy level ranges from about 360 J to 414 J. In implementations, the delivered energy level ranges from about 306 J to 414 J. In other implementations, the therapy delivery circuit delivers at least 360 J of energy. In still yet other implementations, the therapy delivery circuit delivers within 15 percent of 300 J to 480 J.

The controller then verifies whether the patient-worn arrhythmia monitoring and treatment device 100 detects S1728 a normal heart rhythm. If a normal heart rhythm is achieved, the therapy sequence 1700 ends. If no normal heart rhythm is detected, the therapy sequence 1700 returns to charging S1716 the one or more capacitors to the charge voltage Vc based on the detected TTI and the requested, or targeted, delivered energy E(d) and delivers S1719 another therapeutic pulse. In implementations, the patient-worn arrhythmia monitoring and treatment device 100 delivers up to 5 therapeutic pulses. In implementations, the patient-worn arrhythmia monitoring and treatment device 100 delivers up to a selected one of the following treatment limits: 1 therapeutic pulse, 2 therapeutic pulses, and 3 therapeutic pulses. In some implementations, patient-worn arrhythmia monitoring and treatment device 100 delivers a first shock within 15 percent of 360 J of energy and increases energy delivery between 1-15 percent in successive shocks (e.g, 1 percent, 3 percent, 5 percent, 7 percent, 8 percent, 9 percent, and 10 percent)

As described above with regard to FIG. 17, in implementations, the charge voltage Vc is determined based on the transthoracic impedance (TTI) of the body of the patient. In embodiments, the TTI is calculated for a particular patient, and the charge voltage Vc for a therapy sequence is predetermined. In other implementations, the patient-worn arrhythmia monitoring and treatment device actively determines the TTI and adjusts the charge voltage Vc required to deliver a requested, or targeted, quantity of energy, for example, within 15 percent of 360 J of energy. In some embodiments, the charge voltage Vc is determined based on the calculated TTI, the requested, or targeted, delivered energy E(d), and the number of available capacitors for implementations of the device 100 having a plurality of capacitors. In some implementations, a user inputs into the device 100 a request for a delivered quantity energy and in other implementations, the device 100 is programmed to deliver a set, or targeted, value of energy for any patient transthoracic impedance with a range of about 20 ohms to 200 ohms.

Figure 18:
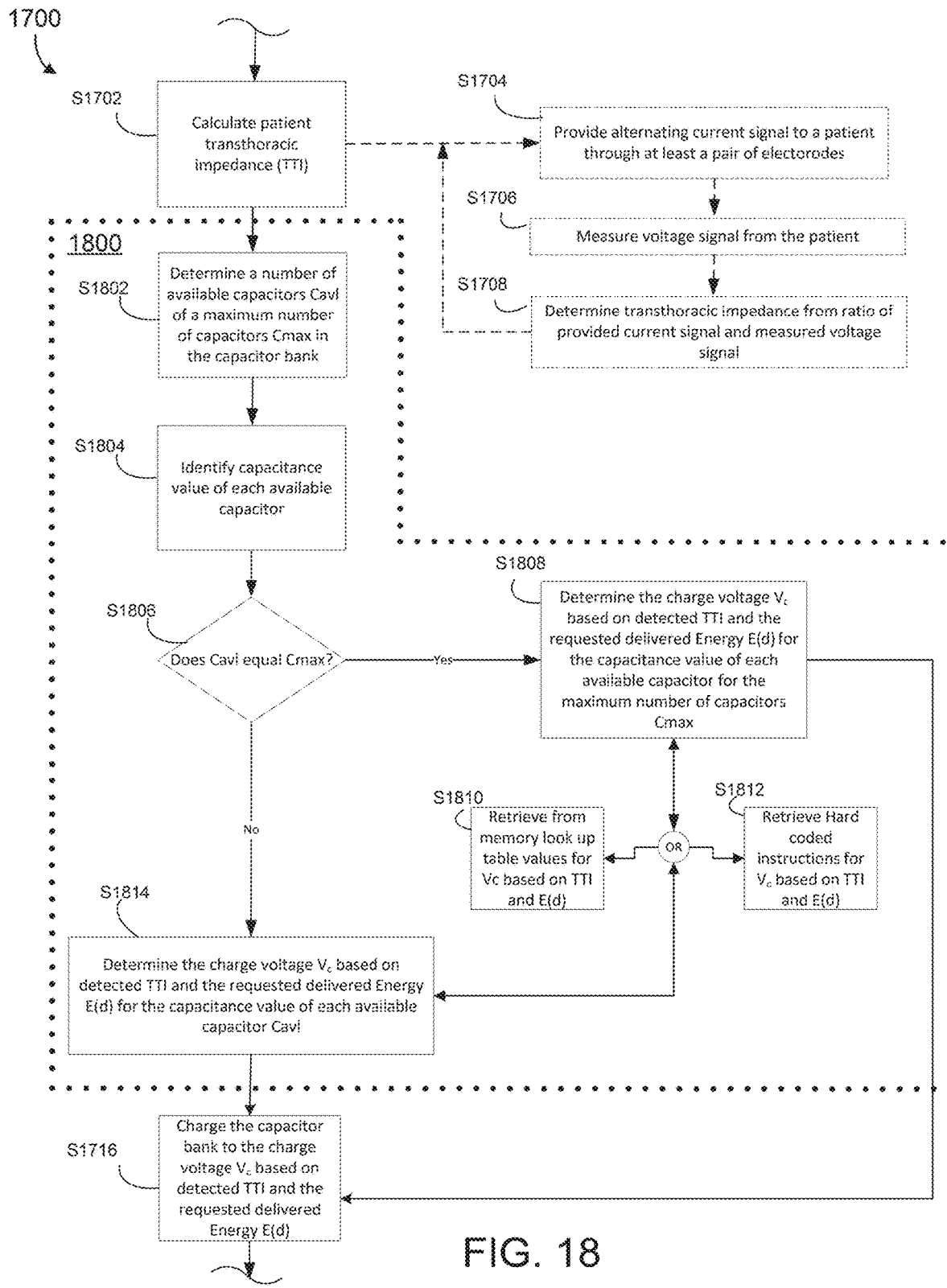
FIG. 18 is a flow diagram illustrating a portion of an embodiment of a medical device control process.

As described above with regard to FIGS. 4A through 4D and FIGS. 11A and 11D, in some implementations, the patient-worn arrhythmia monitoring and treatment device 100 includes a plurality of capacitors 403 each having an identical capacitance value such that if one or more of the plurality of capacitors is unavailable for holding a charge, the available one or more of the capacitors 403 are charged to a corresponding voltage 310 for providing the requested, or targeted, delivered energy 325. In one implementation of the therapy sequence 1700 of FIGS. 17 and 18, the controller, such as the controller 120, 620 of FIGS. 2 and 13, charges one or more of a plurality of capacitors 403 to a charge voltage Vc 310. FIG. 18 provides a charge sequence 1800 for embodiments of the therapy sequence 1700 accounting for the unavailability of one or more of a plurality of capacitors 403.

In order to determine a charge voltage, the controller determines S1802 a number of available capacitors (Cavl) of a maximum number of capacitors (Cmax) of the plurality of capacitors 403. The controller identifies S1804 the capacitance value 305 of each available capacitor 403 and also determines S1806 whether the available number of capacitors (Cavl) equals the maximum number of capacitors (Cmax). If the available number of capacitors (Cavl) equals the maximum number of capacitors (Cmax), the controller determines S1808 the charge voltage Vc based on calculated transthoracic impedance (TTI) and the requested, or targeted, delivered energy E(d) 325 in accordance with the capacitance value 305 of each available capacitor 403 for the maximum number of capacitors (Cmax) in the plurality of capacitors 403.

As described above with regard to the implementation of FIG. 17, in one embodiment, the controller retrieves S1810 from memory look up table values for Vc based on the TTI and the delivered energy E(d) to be delivered to the patient. These look up table values, are for example, values such as those in the tables of FIGS. 4A through 4D for delivered energy 325 of within 15 percent of 360 J and those in the tables of FIGS. 11A and 11B for delivering at least 360 J or for delivering within 15 percent of 300 J to 480 J. In the embodiment of FIGS. 4A through 4D, for example, the device 100 includes one, two, three, or four capacitors 403 and in all embodiments, each capacitor 4030 has a capacitance 305 of 500 microfarads. The charge voltage 310 is determined according to the number of capacitors 302, the targeted, or requested, delivered energy 325, and the patient impedance value 320. In another embodiment, the controller retrieves S1812 hard coded instructions for determining the charge voltage 310 based on the detected TTI 320 and the targeted delivered energy 325. For example, hard coded instructions may include the following IF, THEN instruction for a patient with a transthoracic impedance 320 of 50 ohms: IF the delivered energy E(d) is 360 J and R is 50 ohms, and a number N of 500 microfarad capacitors is one (N=1), THEN set the charge voltage Vc to 1800V.

If the available number of capacitors (Cavl) does not equal the maximum number of capacitors (Cmax), then the controller determines S1814 the charge voltage 310 based on calculated TTI 320 and the requested, or targeted, delivered energy 325 for the capacitance value of each available capacitor. These look up table values, are for example, values such as those in the tables of FIGS. 4A through 4D for delivered energy 325 of within 15 percent of 360 J and those in the tables of FIGS. 11A and 11B for delivering at least 360 J or for delivering within 15 percent of 300 J to 480 J. In one implementation, the controller retrieves S1810 from memory look up table values for charge voltage 310 based on the calculated TTI 320 and the delivered energy 325 to be delivered to the patient.

In the embodiments of FIGS. 4A through 4D, for example, the patient-worn arrhythmia monitoring and treatment device 100 includes one, two, three, or four capacitors 403 and in all embodiments, each capacitor 403 has a capacitance of 500 microfarads. The charge voltage Vc, or V, is determined according to the number of capacitors available Cavl (represented as the capacitor quantity 302 and "N" in FIGS. 4A through 4D), the targeted, or requested, delivered energy E(d) 325, and the patient impedance 320. If, for example, a device 100 includes four 500 uF capacitors 403 but only three are available for charging, the controller looks up a charge voltage 310 of 900V for a patient having an impedance of 50 ohms. In another embodiment, the controller retrieves S1812 hard coded instructions for determining the charge voltage Vc 310 based on the calculated TTI 320 and the requested, or targeted, delivered energy 325. For the example of only three out of four capacitors being available for charging, hard coded instructions may include the following IF, THEN instruction for a patient with a TTI 320 of 50 ohms: IF the delivered energy E(d) is 360 J and R is 50 ohms, and a number N of 500 microfarad capacitors available is three (N=3), THEN set the charge voltage Vc to 900V.

Figure 19:
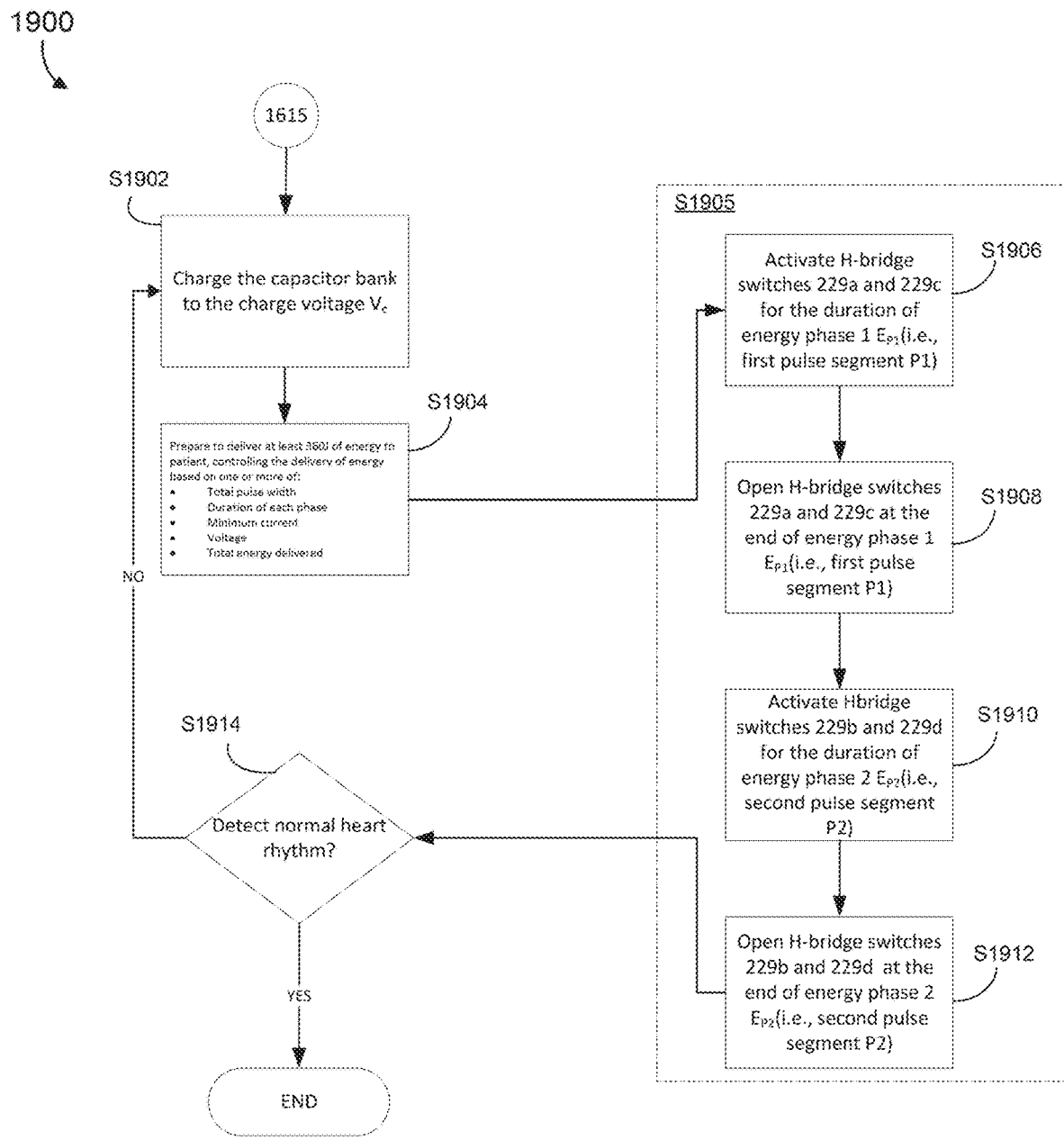
FIG. 19 is a flow diagram illustrating an embodiment of a medical device control process.

The embodiments of FIGS. 17 and 18 include the controller first calculating S1702 patient transthoracic impedance (TTI) and then determining a charge voltage 310 of the capacitor 403 based on the calculated TTI. In some embodiments, the patient-worn arrhythmia monitoring and treatment device 100 executes a therapy sequence 1900 delivering within 15 percent of 360 J of energy or at least 360 J of energy to the body of a patient without first calculating TTI 320 for the patient. In such embodiments, the controller, such as the controllers 120, 620 of FIGS. 2 and 13, of the device 100 executes the therapy sequence 1900 by controlling the delivery of energy based on one or more treatment parameters. As shown in FIG. 19, the controller charges S1902 one or more capacitors 403, or the capacitor bank, to a charge voltage Vc 310 sufficient for delivering at least 360 J of energy into the body of a patient. The controller prepares to deliver S1904 at least 360 J of energy to a patient while controlling the delivery of energy based on adjusting one or more of total pulse width (e.g., T in FIGS. 21A and 21B and Pw in FIGS. 22 and 23), the duration of each phase (e.g, P1 and P2 of FIGS. 22 and 23), minimum current 335, voltage 310 and total energy delivered 325. The controller delivers S1905 energy in to the body of the patient by controlling energy using, for example, an H-Bridge. In the embodiment to the therapy sequence 1900 of FIG. 19, the controller activates S1906 two of four H-bridge switches, such as switches 229a and 229c of FIG. 3, for the duration of a first energy phase (e.g., first pulse segment P1) and then opens S1908 the activated H-bridge switches at the end of the first energy phase. The controller activates S1910 two other of the four H-bridge switches, such as switches 229b and 229d for the duration of the second energy phase (e.g., second pulse segment P2) and then opens S1912 the two other H-Bridge switches at the end of the second energy phase.

The controller then verifies whether the patient-worn arrhythmia monitoring and treatment device 100 detects S1914 a normal heart rhythm. If a normal heart rhythm is achieved, the therapy sequence 1900 ends. If no normal heart rhythm is detected, the therapy sequence 1900 returns to charging S1902 the one or more capacitors 403 to the charge voltage Vc 310 based on the calculated TTI 320 and the requested, or targeted, delivered energy E(d) 325 and delivers S1905 another therapeutic pulse. In implementations, the patient-worn arrhythmia monitoring and treatment device 100 delivers up to 5 therapeutic pulses. In implementations, the patient-worn arrhythmia monitoring and treatment device 100 delivers up to a selected one of the following treatment limits: 1 therapeutic pulse, 2 therapeutic pulses, and 3 therapeutic pulses. In some implementations, patient-worn arrhythmia monitoring and treatment device 100 delivers a first shock within 15 percent of 360 J of energy and increases energy delivery between 1-15 percent in successive shocks (e.g., 1 percent, 3 percent, 5 percent, 7 percent, 8 percent, 9 percent, and 10 percent)

FIG. 20A depicts an example schematic of a boost converter circuit 2000 of a patient-worn arrhythmia monitoring and treatment device 100 that delivers, in implementations, at least 360 J of energy to the body of a patient without initially calculating the patient's TTI. For example, the circuit 2000 is configured to deliver within 15 percent of 360 J to 480 J to such patients. Example circuits for delivering energy into a body of a patient having an unknown impedance are described in, for example, U.S. Pat. No. 9,289,617 entitled "METHOD AND APPARATUS FOR APPLYING RECTILINEAR BIPHASIC POWER WAVEFORM TO A LOAD," the content of which is incorporated herein by reference.

The example circuit 2000 includes a storage capacitor 2002, an inductor 2004, a switch 2006, a microcontroller 2008 for controlling the switch and therefore track the flow of energy (e.g., by tracking voltage and current delivered to the patient over the pulse duration). The circuit 2000 also includes a diode 2010, a ripple-filtering capacitor 2009, and an ammeter 2012 for determining the current delivered to the patient 2016. An H-Bridge 2014 couples with the boost converter 2010 for delivering, for example, at least 360 J of energy into the patient 2016 without initially calculating the patient's TTI 320, with positive, negative, or alternating polarities determined by the prescribed conduction states of the bridge arms. The tabulated values of FIG. 20B represent example voltages 2506 for a stored energy E(s) of 450 J for a range of capacitances 2502 from 150 microfarads to 650 microfarads for the circuit 2000 to deliver into the body of a patient 2016, for example, at least 360 J. By storing an energy E(s) greater than an delivered energy E(d) delivered into the body of the patient, the capacitor 2002 is able to provide sufficient current to achieve the desired therapeutic quantity of delivered energy E(d).

The microcontroller 2008 of the boost converter circuit 2000 controls the switch 2006 to incrementally deliver current to the H-Bridge over dynamically-regulated durations such that the delivered energy E(d) is at or within a range of the desired therapeutic quantity of energy for a monitored voltage across the body of the patient 2016. Energy can be calculated being equal to voltage multiplied by current multiplied by the duration of the pulse. For example, a pulse duration may be pre-set to around 10 ms. Accordingly, over the duration of the pulse, and a measured voltage across a patient 2016, current is constantly monitored by the ammeter 2012 and regulated by the microcontroller 2008 opening and closing the switch 2006. This controls the flow of current so that the resultant delivered energy E(d) delivered into the body of the patient is, in examples, within 15 percent of 360 J or, for example, at least 360 J. The boost converter circuit 200 controls and regulates the delivery of a constant current, resulting in a constant power level delivered to the patient during the delivery of a desired energy impulse without first calculating the patient transthoracic impedance (TTI).

In some implementations, such as those of FIGS. 21A and 21B, the patient-worn arrhythmia monitoring and treatment device 100, such as that of FIGS. 1-3 and 13, delivers 360 J of energy into the body of a patient having a transthoracic impedance 320 in the range of about 25-150 ohms without first calculating patient impedance TTI. In some embodiments, the patient-worn arrhythmia monitoring and treatment device 100 delivers energy into the body of the patient for a maximum time duration 330 of 25 ms such that for patients having an impedance 320 ranging from about 175-200 ohms, the device 100 delivers energy into the body of the patient in a biphasic waveform, for example a rectilinear biphasic waveform, and truncates the second pulse phase P2 at a time of 25 ms.

In the implementation of FIG. 21A, the patient-worn arrhythmia monitoring and treatment device 100 has a number of capacitors 302g of one and a charge voltage 310g of 2100V for all patient impedance values 320g. The patient-worn arrhythmia monitoring and treatment device 100 provides a delivered energy E(d) 325g of 360 J within about 25 seconds to all patients having an impedance in a range of about 25 to 150 ohms. For patients having an impedance 320g of about 175 ohms, the patient-worn arrhythmia monitoring and treatment device 100 provides a delivered energy 325g in a range of about 250 to 360 J and truncates the treatment pulse at a maximum duration of about 25 ms. For patients having an impedance 320g of about 200 ohms, the patient-worn arrhythmia monitoring and treatment device 100 provides a delivered energy 325g in a range of about 175 to 360 J and truncates the treatment pulse at a maximum duration 330g of about 25 ms. As with the implementations described above with regard to FIGS. 4A through 4D, the implementations of FIGS. 21A and 21B all maintain current at or above a minimum current 335 of 4 A.

In the implementation of FIG. 21B, the patient-worn arrhythmia monitoring and treatment device 100 has a number of capacitors 302h of two and a charge voltage 310h of 2100V for all patient impedance values 320h. The device 100 provides a delivered energy 325h of 360 J within about 25 seconds to all patients having an impedance 320h in a range of about 25 to 125 ohms. For patients having an impedance 320h of about 155 ohms, the device 100 provides a delivered energy 325h in a range of about 250 to 360 J and truncates the treatment pulse at a maximum duration of about 25 ms. For patients having an impedance 320h of about 175 ohms, the device 100 provides a delivered energy 325h in a range of about 175 to 360 J and truncates the treatment pulse at a maximum duration 330h of about 25 ms. For patients having an impedance 320h of about 200 ohms, the device 100 provides a delivered energy 325h in a range of about 175 to 360 J and truncates the treatment pulse at a maximum duration 330h of about 25 ms. As with the implementations described above with regard to FIGS. 4A through 4D, the implementations of FIGS. 21A and 21B all maintain current at or above a minimum current 335 of 4 A.

In some embodiments, such as those of FIGS. 21A and 21B, the patient-worn arrhythmia monitoring and treatment device 100 truncates a treatment pulse at a maximum duration 330g, 330h. In other implementations, the patient-worn arrhythmia monitoring and treatment device 100 truncates a treatment pulse once the delivered energy 325g, 325h reaches a threshold value, such as 360 J. In some embodiments, the device 100 truncates a treatment pulse once either the duration of treatment 330 reaches a threshold time, such as about 20-25 ms (e.g. 20 ms, 22 ms, 23 ms, 25 ms) or a threshold for delivered energy 325, such as within 15 percent of 360 J (e.g. 306 J, 325 J, 343 J, 352 J, 378 J, 391 J, 405 J, 410 J, 414 J).

In implementations in accordance with the example values of FIGS. 21A and 21B, the patient-worn arrhythmia monitoring and treatment device 100 delivers up to 5 therapeutic pulses. In implementations in accordance with the example values of FIGS. 21A and 21B, the patient-worn arrhythmia monitoring and treatment device 100 delivers up to a selected one of the following treatment limits: 1 therapeutic pulse, 2 therapeutic pulses, and 3 therapeutic pulses. In some implementations in accordance with the example values of FIGS. 21A and 21B, patient-worn arrhythmia monitoring and treatment device 100 delivers a first shock within 15 percent of 360 J of energy and increases energy delivery between 1-15 percent in successive shocks (e.g, 1 percent, 3 percent, 5 percent, 7 percent, 8 percent, 9 percent, and 10 percent)

As described earlier, FIGS. 22 and 23 depict embodiments of rectilinear biphasic waveforms 300g, 300h delivering 360 J of energy across a range of transthoracic impedances 320. In implementations, the device 100 delivers within 15 percent of 360 J of energy into a patient body 102 over a biphasic pulse of fixed duration ranging from about 10-12 ms. The peak current 333 decreases as the patient impedance 320 increases and the charge voltage 310 across the capacitors 403 increases as patient impedance 320 increases. The initial stored energy 315 in the one or more capacitors 403 increases with increasing patient impedance 320. For example, in one embodiment, for a patient having a TTI 320 of 50 ohms, a 100 microfarad capacitor having a 3128 voltage rating is set to store 489 J of energy and delivers into a patient within 15 percent of 360 J in a rectilinear biphasic pulse lasting 10 seconds. In another embodiment, for a patient having a TTI 320 of 200 ohms, a 100 microfarad capacitor having a 3172 voltage rating is set to store 568.5 J of energy and delivers into a patient within 15 percent of 360 J in a biphasic, rectilinear pulse lasing 10 seconds. In these embodiments of fixed duration pulses, the therapy delivery circuit 202 may include one or more feedback loops for maintaining the value (or band of values) of the peak current 333 throughout the duration of the first pulse segment P1 and the second pulse segment P2 so that the therapy device 100 delivers within 15 percent of 360 J of energy to a patient having a transthoracic impedance in the range of about 20 to 200 ohms.

In some implementations, the patient-worn arrhythmia monitoring and treatment device 100 delivers a treatment pulse of delivered energy E(d) 325 in accordance with the biphasic waveforms 300g, 300h of FIGS. 22 and 23 by first calculating patient transthoracic impedance 320 and looking up a charge voltage Vc 310 value in a look up table based on impedance 320. In other embodiments, the device 100 delivers a treatment pulse of delivered energy E(d) 325 in accordance with the biphasic waveforms 300g, 300h of FIGS. 22 and 23 without first calculating patient transthoracic impedance 320g, 320h. As described with regard to FIGS. 21A and 21B, the patient-worn arrhythmia monitoring and treatment device 100 truncates a treatment pulse at a maximum duration 330. In other implementations, the patient-worn arrhythmia monitoring and treatment device 100 truncates a treatment pulse once the delivered energy E(d) 325 reaches a threshold value, such as 360 J. In some embodiments, the patient-worn arrhythmia monitoring and treatment device 100 truncates a treatment pulse once either the duration of treatment reaches a threshold time, such as 10 ms, or a threshold for delivered energy E(d) 325, such as within 15 percent of 360 J (e.g. 306 J, 325 J, 343 J, 352 J, 378 J, 391 J, 405 J, 410 J, 414 J).

In implementations, the patient-worn arrhythmia monitoring and treatment device 100 delivers up to 5 therapeutic pulses in accordance with the example biphasic waveforms of FIGS. 22 and 23. In the implementations of the biphasic waveforms of FIGS. 22 and 23, the patient-worn arrhythmia monitoring and treatment device 100 delivers up to a selected one of the following treatment limits: 1 therapeutic pulse, 2 therapeutic pulses, and 3 therapeutic pulses. In some implementations, patient-worn arrhythmia monitoring and treatment device 100 delivers a first shock within 15 percent of 360 J of energy and increases energy delivery between 1-15 percent in successive shocks (e.g, 1 percent, 3 percent, 5 percent, 7 percent, 8 percent, 9 percent, and 10 percent)

OTHER CONSIDERATIONS

Although the subject matter contained herein has been described in detail for the purpose of illustration, it is to be understood that such detail is solely for that purpose and that the present disclosure is not limited to the disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

Other examples are within the scope and spirit of the description and claims. Additionally, certain functions described above can be implemented using software, hardware, firmware, hardwiring, or combinations of any of these. Features implementing functions can also be physically located at various positions, including being distributed such that portions of functions are implemented at different physical locations.

What is claimed is:

1. A patient-worn arrhythmia monitoring and treatment device, comprising:
   a pair of therapy electrodes configured to be worn continuously by a patient for an extended period of time ranging between around 7 days to 3 months;
   at least one pair of sensing electrodes disposed proximate to skin of the patient and configured to continually sense at least one ECG signal of the patient over the extended period of time;
   a therapy delivery circuit coupled to the pair of therapy electrodes and configured to deliver one or more therapeutic pulses to the patient through the pair of therapy electrodes; and
   a controller coupled to the therapy delivery circuit and configured to
     analyze the at least one ECG signal of the patient and detect one or more treatable arrhythmias based on the at least one ECG signal,
     cause delivery of conductive gel to a treatment site of the patient's skin on detecting the one or more treatable arrhythmias and receiving no patient response to a prompt, and
     cause the therapy delivery circuit to deliver the one or more therapeutic pulses to the patient within around one second to one minute of the delivery of conductive gel, at least one of the one or more therapeutic pulses being formed as a biphasic waveform delivering within 15 percent of 360 J of energy to a body of the patient for a patient body having a transthoracic impedance in a range from about 20 to about 200 ohms.

2. The patient-worn arrhythmia monitoring and treatment device of claim 1, further comprising selectable energy levels, wherein the delivered one or more therapeutic pulses does not vary from 360 J of energy by more than 15 percent at any selected energy level.

3. The patient-worn arrhythmia monitoring and treatment device of claim 1, further comprising selectable energy levels, wherein the delivered one or more therapeutic pulses is no less than 85 percent of 360 J at any selected energy level.

4. The patient-worn arrhythmia monitoring and treatment device of claim 1, further comprising selectable energy levels, wherein the delivered energy ranges from about 360 J to 414 J at any selected energy level.

5. The patient-worn arrhythmia monitoring and treatment device of claim 1, wherein the controller is further configured to detect the transthoracic impedance of the body of the patient and determine a charge voltage for delivering the one or more therapeutic pulses within 15 percent of 360 J.

6. The patient-worn arrhythmia monitoring and treatment device of claim 5, the controller is further configured to determine the charge voltage based on a look up table associating the charge voltage with the detected transthoracic impedance.

7. The patient-worn arrhythmia monitoring and treatment device of claim 5, the controller is further configured to determine the charge voltage based on one or more hard coded instructions associating the charge voltage with the detected transthoracic impedance.

8. The patient-worn arrhythmia monitoring and treatment device of claim 1, further comprising a boost converter circuit configured to deliver the one or more therapeutic pulses within 15 percent of 360 J regardless of transthoracic impedance of the body of the patient.

9. The patient-worn arrhythmia monitoring and treatment device of claim 1, wherein the one or more treatable arrhythmias comprise at least one of a ventricular fibrillation and a ventricular tachycardia.

10. The patient-worn arrhythmia monitoring and treatment device of claim 1, further comprising a source of electrical energy storing and providing at least 360 J of energy to the therapy delivery circuit, wherein the biphasic waveform comprises a biphasic truncated exponential pulse.

11. The patient-worn arrhythmia monitoring and treatment device of claim 10, wherein the biphasic truncated exponential pulse has a first pulse segment and a second pulse segment and a selected amount of the provided energy is applied to the patient during the first pulse segment and a remaining amount of the provided energy is applied to the patient during the second pulse segment.

12. The patient-worn arrhythmia monitoring and treatment device of claim 11, wherein the therapy delivery circuit further comprises an H-bridge to produce the first pulse segment and the second pulse segment of the biphasic truncated exponential pulse.

13. The patient-worn arrhythmia monitoring and treatment device of claim 11, wherein the therapy delivery circuit is configured to truncate the provided energy being delivered to the body of a patient when the provided energy delivered to the body of the patient is substantially equal to 360 J.

14. The patient-worn arrhythmia monitoring and treatment device of claim 1, wherein the biphasic waveform comprises a rectilinear biphasic waveform.

15. The patient-worn arrhythmia monitoring and treatment device of claim 1, further comprising a pulse voltage monitor, a pulse current monitor, and a timer for measuring a pulse voltage and a pulse current over a predetermined time period.

16. The patient-worn arrhythmia monitoring and treatment device of claim 1, further comprising a garment configured to be worn about a torso of the patient for the extended period of time.

17. The patient-worn arrhythmia monitoring and treatment device of claim 16, wherein at least one of the pair of therapy electrodes and the at least one pair of sensing electrodes are supported by the garment.

18. The patient-worn arrhythmia monitoring and treatment device of claim 16, wherein at least one of the pair of therapy electrodes and the at least one pair of sensing electrodes are integrated with the garment.

19. The patient-worn arrhythmia monitoring and treatment device of claim 16, further comprising a source of electrical energy storing and providing at least 360 J of energy to the therapy delivery circuit and wherein the source of electrical energy and the therapy delivery circuit are supported by the garment.

20. The patient-worn arrhythmia monitoring and treatment device of claim 19, wherein the source of electrical energy comprises a plurality of capacitors and wherein the plurality of capacitors are distributed about and integrated into the garment.

21. The patient-worn arrhythmia monitoring and treatment device of claim 1, wherein at least one of the pair of therapy electrodes and at least one sensing electrode of the at least one pair of sensing electrodes are disposed on a patch configured to be adhesively coupled to a torso of the patient for a term of not more than 14 days.

22. The patient-worn arrhythmia monitoring and treatment device of claim 1, wherein the pair of therapy electrodes and the at least one pair of sensing electrodes are disposed on a pair of patches configured to be adhesively coupled to a torso of the patient, and wherein each of the pair of patches comprises one therapy electrode of the pair of therapy electrodes and at least one sensing electrode of the at least one pair of sensing electrodes.

23. The patient-worn arrhythmia monitoring and treatment device of claim 1, further comprising gel deployment circuitry for reducing an impedance between each therapy electrode of the pair of therapy electrodes and the patient's skin.

24. A patient-worn arrhythmia monitoring and treatment device, comprising:
a garment configured to be worn about a torso of a patient;
a pair of therapy electrodes configured to be worn continuously by the patient for an extended period of time ranging between around 7 days to 3 months;
at least one pair of sensing electrodes configured to monitor at least one ECG signal of the patient;
a therapy delivery circuit coupled to the pair of therapy electrodes and configured to deliver one or more therapeutic pulses to the patient through the therapy electrodes;
a plurality of capacitors operably connected to the therapy delivery circuit and integrated into the garment, the plurality of capacitors being configured to store energy for at least one therapeutic pulse; and
a controller coupled to the therapy delivery circuit and configured to
analyze the at least one ECG signal of the patient and detect one or more treatable arrhythmias based on the at least one ECG signal,
cause delivery of conductive gel to a treatment site of the patient's skin on detecting the one or more treatable arrhythmias and receiving no patient response to a prompt, and
cause the therapy delivery circuit to deliver the one or more therapeutic pulses to the patient within around one second to one minute of the delivery of conductive gel, at least one of the one or more therapeutic pulses being formed as a biphasic waveform delivering within 15 percent of 360 J of energy to a body of the patient for a patient body having a transthoracic impedance in a range from about 20 to about 200 ohms.

25. The patient-worn arrhythmia monitoring and treatment device of claim 24, wherein the plurality of integrated capacitors are distributed about the garment.

26. The patient-worn arrhythmia monitoring and treatment device of claim 24, wherein the pair of therapy electrodes and the at least one pair of sensing electrodes are supported by the garment and wherein the garment is configured to be worn continuously by the patient for the extended period of time.

27. The patient-worn arrhythmia monitoring and treatment device of claim 24, wherein the pair of therapy electrodes or the at least one pair of sensing electrodes are supported by the garment and wherein the garment is configured to be worn continuously by the patient for the extended period of time.

28. The patient-worn arrhythmia monitoring and treatment device of claim 24, wherein the plurality of capacitors are integrated into separate regions of the garment.

29. The patient-worn arrhythmia monitoring and treatment device of claim 24, wherein the plurality of capacitors are nested in a stacked configuration.

30. The patient-worn arrhythmia monitoring and treatment device of claim 24, further comprises a rechargeable battery configured to be removably coupled to the plurality of capacitors.

31. The patient-worn arrhythmia monitoring and treatment device of claim 24, further comprising a rechargeable battery for powering the plurality of capacitors, and wherein the garment removably couples to the rechargeable battery.

32. The patient-worn arrhythmia monitoring and treatment device of claim 24, wherein at least one of the plurality of capacitors is contoured to conform to a silhouette of the patient.

33. The patient-worn arrhythmia monitoring and treatment device of claim 32, wherein at least one of the plurality of capacitors has a thickness of between 1 mm and 40 mm.

34. The patient-worn arrhythmia monitoring and treatment device of claim 24, wherein the biphasic waveform comprises a biphasic truncated exponential pulse and wherein the biphasic truncated exponential pulse has a first pulse segment and a second pulse segment.

35. The patient-worn arrhythmia monitoring and treatment device of claim 34, further comprising an H-bridge to produce the first pulse segment and the second pulse segment of the biphasic truncated exponential pulse, wherein a first portion of electrical energy stored in the plurality of capacitors is applied to the patient in the first pulse segment and a second amount of electrical energy stored in the plurality of capacitors is applied to the patient during the second pulse segment.

36. The patient-worn arrhythmia monitoring and treatment device of claim 24, further comprising a patient notification signal, wherein, in response to detecting the one or more treatable arrhythmias, the controller is configured to prompt the patient to respond to indicate that the patient is conscious.

37. The patient-worn arrhythmia monitoring and treatment device of claim 36, wherein, in an absence of a response from the patient indicating that the patient is conscious, the controller is configured to cause the therapy delivery circuit to deliver the one or more therapeutic pulses to the patient.

38. The patient-worn arrhythmia monitoring and treatment device of claim 24, wherein the plurality of capacitors comprises at least 2 capacitors.

39. The patient-worn arrhythmia monitoring and treatment device of claim 38, wherein the controller is further configured to select a subset of the plurality of capacitors and deliver the one or more therapeutic pulses to the patient using the subset.

40. The patient-worn arrhythmia monitoring and treatment device of claim 24, wherein the plurality of capacitors comprises 4 capacitors.

41. A patient-worn arrhythmia monitoring and treatment device, comprising:
- a garment configured to be worn about a torso of a patient;
- a pair of therapy electrodes configured to be worn continuously by the patient for an extended period of time ranging between around 7 days to 3 months;
- at least one pair of sensing electrodes configured to monitor at least one ECG signal of the patient;
- a therapy delivery circuit coupled to the pair of therapy electrodes and configured to deliver one or more therapeutic pulses to the patient through the therapy electrodes;
- a plurality of capacitors operably connected to the therapy delivery circuit and distributed about and integrated into the garment, the plurality of capacitors being configured to store energy for at least one therapeutic pulse; and
- a controller coupled to the therapy delivery circuit and configured to
  - analyze the at least one ECG signal of the patient and detect one or more treatable arrhythmias based on the at least one ECG signal,
  - cause delivery of conductive gel to a treatment site of the patient's skin on detecting the one or more treatable arrhythmias and receiving no patient response to a prompt, and
  - cause the therapy delivery circuit to deliver the one or more therapeutic pulses to the patient within around one second to one minute of the delivery of conductive gel, at least one of the one or more therapeutic pulses being formed as a biphasic waveform delivering 360 J to 575 J of energy to a body of the patient for a patient body having a transthoracic impedance in a range from about 20 to about 200 ohms.

* * * * *